United States Patent [19]
Yu

[11] Patent Number: 5,817,752
[45] Date of Patent: Oct. 6, 1998

[54] CYCLIC POLYPEPTIDES COMPRISING A THIOETHER LINKAGE AND METHODS FOR THEIR PREPARATION

[75] Inventor: Lin Yu, San Diego, Calif.

[73] Assignee: La Jolla Pharmaceutical Company, San Diego, Calif.

[21] Appl. No.: 748,021

[22] Filed: Nov. 12, 1996

Related U.S. Application Data

[63] Continuation of Ser. No. 660,739, Jun. 6, 1996.

[51] Int. Cl.$^6$ .............................. A61K 38/12; C07K 7/00
[52] U.S. Cl. ................................. 530/317; 514/9; 514/11; 530/333; 530/336
[58] Field of Search ................................ 530/317; 514/9, 514/11

[56] References Cited

U.S. PATENT DOCUMENTS 5,268,454  12/1993  Barstad et al. ....................... 424/193.1

FOREIGN PATENT DOCUMENTS 2 282 813  4/1995  United Kingdom.
2 282 815  4/1995  United Kingdom.

OTHER PUBLICATIONS

Appel et al, "Notiz über ein bequemes verfahren zur darstellung von dichlorphosphoranen" *Chem. Ber.* (1977) 110:2382–2384. A partial English translation is enclosed.
Appel et al., "Reaktionen im zweikomponentensystem triphenylphospin/tetrachlormethan" *Chem. Ber.* (1976) 109:58–70. An English abstract is included on p. 58 of this document.
Balaram, "The design and construction of synthetic protein mimics" *Pure & Appl Chem.* (1992) 64:1061–1066.
Blondelle et al., "Novel antimicrobial compounds identified using synthetic combinatorial library technology" *Trends in Biotechnology* (1996) 14:60–65.
Burgess et al., "Comparison of the effects of (2S,3S)–2,3–methanomethionine, (2R,3R)–2,3–methanomethionine, and (2R,3R)–2,3 methanophenylalanine on the conformations of small peptides" *J. Am. Chem. Soc.* (1995) 117:3808–3819.
Cheung et al., "Chloroalanyl and propargylglycyl dipeptides. Suicide substrate containing antibacterials" *J. Med. Chem.* (1983) 26:1733–1741.
Cheung et al., "Chloroalanyl antibiotic peptides: Antagonism of their antimicrobial effects by L–alanine and L–alanyl peptides in gram–negative bacteria" *J. Med. Chem.* (1986) 29:2060–2068.
Coutts et al., "Pharmacological intervention in antibody mediated disease" *Lupus* (1996) 5:158–159.
Dintzis, "Rational design of conjugate vaccines" *Pediatric Res.* (1992) 32:376–385.
Ellman, "Tissue sulfhydryl groups" *Arch. Biochem. Biophys.* (1959) 82:70–77.

Fields et al., "Solid phase peptide synthesis utilizing 9–fluorenylmethoxycarbonyl amino acids" *Int. J. Pept. Protein Res.* (1990) 35:161–214.
Fischer, "Application of t–butyldimethylsily ethers of serine, threonine and tyrosine and peptide synthesis" *Tetrahedron Lett.* (1992) 49:7605–7608.
Fukase et al., "Synthetic study on peptide antibiotic nisin. II. The synthesis of Ring B" *Bull. Chem. Soc. Jpn.* (1985) 59:2505–2508.
Hinds et al., "Synthesis, conformational properties, and antibody recognition of peptides containing β–turn mimetics based on α–alkylproline derivatives" *J. Med. Chem.* (1991) 34:1777–1789.
Hruby et al., "Design of novel synthetic peptides including cyclic conformationally and topgraphically constrained analogs" *Methods in Molecular Biology* (1994) 35:201–240.
Hruby et al., "Emerging approaches in the molecular design of receptor–selective peptide ligands: conformational, topographical and dynamic considerations" *Biochem. J.* (1990) 268:249–262.
Jack et al., "Unique peptide modifications involved in the biosynthesis of lantibiotics" *Trend in Biotechnology* (1995) 13:269–278.
Jones et al., "Conjugates of double–stranded oligonucleotides with poly(ethylene glycol) and keyhold limpet hemocyanin: A model for treating systemic lupus erythematosus" *Bioconjugate. Chem.* (1994) 5:390–399.
Jones et al., "Immunospecific reduction of antioligonucleotide antibody–forming cells with a tetrakis–ogigonucleotide conjugate (LJP 394), a therapeutic candidate for the treatment of lupus nephritis" *J. Med. Chem.* (1995) 38:2138–2144.

(List continued on next page.)

*Primary Examiner*—Cecilia J. Tsang
*Assistant Examiner*—S. G. Marshall
*Attorney, Agent, or Firm*—Morrison & Foerster LLP

[57] ABSTRACT

This invention relates generally to cyclic polypeptides comprising a thioether linkage and methods for their preparation. More particularly, this invention relates to halogenated polypeptides having at least one haloalanine-like amino acid, and methods for their preparation which involve converting the hydroxyl group (i.e., —OH) of a serine-like amino acid to a halo group (i.e., —X where X is Cl, Br, or I) with the aid of a phosphorus-based halogenation reagent such as a triphenylphosphine dihalide (i.e., $(C_6H_5)_3PX_2$, wherein X is Cl, Br, or I), a triphenylphosphite dihalide (i.e., $(C_6H_5O)_3PX_2$, wherein X is Cl, Br, or I), or a mixture of triphenylphosphine or triphenylphosphite with a halohydrocarbon (i.e., "halo-conversion"). This invention also relates to cyclic polypeptides having at least one polypeptide loop comprising a thioether linkage, and methods for their preparation which employ halogenated polypeptides and which involve intramolecular alkylation of the thiol group of a cysteine-like amino acid by the halo group of a haloalanine-like amino acid under suitable basic conditions to form a thioether linkage (i.e., "cyclization").

23 Claims, 9 Drawing Sheets

OTHER PUBLICATIONS

Jost et al., "Amino acids and peptides. LXXIV. Derivatives of L–cystathionine suitable for peptide synthesis" *Collect. Czech. Chem. Commun.* (1967) 32:2485–2490.

Cavelier–Frontin et al. "New diastereoselective synthesis of protected meso–lanthionine with discrimination of the chiral centers" *Tetrahedron Asymmetry* (1992) 3:85–94. Jung, "Lantibiotics–ribosomally synthesized biologically active polypeptides containing sulfide bridges and α,β–didehydroamino acids" *Angew. Chem. Int. Ed. Engl.* (1991) 30:1051–1192.

Kaiser et al., "Color test for detection of free terminal amino groups in the solid–phase synthesis of peptides" *Anal. Biochem.* (1970) 34:595–598.

Kataoka et al., "The utility of side–chain cyclization in determining the receptor–bound conformation of peptides: Cyclic tripeptides and angiotensin II" *Biopolymers* (1992) 32:1519–1533.

Katz et al., "Structure–based design of high affinity streptavidin binding cyclic peptide ligands containing thioether cross–links" *J. Am. Chem. Soc.* (1995) 117:8541–8547.

Lebl et al., "Synthesis of cyclic peptides by solid phase methodology" *Tetrahedron Lett.* (1984) 25:2067–2068.

Liu et al., "New procedures for preparation and isolation of conjugates of proteins and a synthetic copolymer of D–amino acids and immunochemical characterization of such conjugates" *Biochemistry* (1979) 18:690–697.

Mayer et al., "An alternative solid–phase approach to $C_1$–oxytocin" *Tetrahedron Lett.* (1995) 36:7387–7390.

Mosberg et al., "Dithioether–containing cyclic peptides" *J. Am. Chem. Soc.* (1985).

Osapay et al., "New application of peptide cyclization on an oxime resin (the PCOR method): Preparation of lanthionine peptides" *J. Chem. Soc. Chem. Commun.* (1993):1599–1600.

Polinsky et al., "Synthesis and conformational properties of the lantionine–bridged opioid peptide [D–Ala$_L$², Ala$_L$⁵]enkephalin as determined by NMR and computer simulations" *J. Med. Chem.* (1992) 35:4185–4194.

Probert et al., "Lanthionines for solid phase synthesis" *Tetrahedron Lett.* (1996) 37:1101–1104.

Safar et al., "The carba–modification of cystine–containing peptides: Synthesis of selectively protected cystathionines and their incorporation in the oxytocin molecule" *Peptides: Chemistry, Structure and Biology* (Hodges, R.S. and Smith, J. A. Eds.) Escom, Leiden, The Netherlands, (1994) 119–120.

Sahl et al., "Biosynthesis and biological activities of lantibiotics with unique post–translational modificaions" *Eur. J. Biochem.* (1995) 230:827–853.

Shao et al., "A facile synthesis of orthogonally protected stereoisomeric lanthionines by regioselective ring opening of serine β–lactone derivatives" *J. Org. Chem.* (1995) 60:2956–2957.

Stewart et al., *Solid Phase Peptide Synthesis,* 2nd., Pierce Chemical Co.: Rockford, IL., (1984), p. 82.

Tam, "Synthesis and applications of branched peptides in immunological methods and vaccines" *Peptides: Synthesis, Structures, and Applications* (Gutte ed.) Academic Press, San Diego, (1995) 455–500.

Tam, "Synthetic peptide vaccine design: Synthesis and properties of a high–density multiple antigenic peptide systems" *Proc. Natl. Acad. Sci. USA* (1988) 85:5409–5413.

Toniolo et al., "Structures of peptides from α–amino acids methylated at the α–carbon" *Biopolymers* (1993) 33:1061–1072.

Toniolo, "Conformationally restricted peptides through short–range cyclizations" *Int. J. Peptide Protein Res.* (1990) 35:287–300.

Wünsch et al., "1–(tert–butylthio)–1.2–hydrazinedicarboxylic acid derivatives. New reagents for the introduction of the S–tert–butylthio group into cysteine and cysteine derivatives" *Hoppe-–Seyler's Z. Physiol. Chem.* (1982), 363:1461–1464.

R' = H or TBDMS

⇩ Halogenation

X = Cl, Br, or I

⇩ Cyclization

CYCLIC POLYPEPTIDES COMPRISING A THIOETHER LINKAGE AND METHODS FOR THEIR PREPARATION

This application is a continuation of application Ser. No. 08/660,739 filed Jun. 6, 1996.

TECHNICAL FIELD

This invention relates generally to cyclic polypeptides comprising a thioether linkage and methods for their preparation. More particularly, this invention relates to halogenated polypeptides having at least one haloalanine-like amino acid, and methods for their preparation which involve converting the hydroxyl group (i.e., —OH) of a serine-like amino acid to a halo group (i.e., —X where X is Cl, Br, or I) with the aid of a phosphorus-based halogenation reagent such as a triphenylphosphine dihalide (i.e., $(C_6H_5)_3PX_2$, wherein X is Cl, Br, or I), a triphenylphosphite dihalide (i.e., $(C_6H_5)_3PX_2$, wherein X is Cl, Br, or I), or a mixture of triphenylphosphine or triphenylphosphite with a halohydrocarbon (i.e., "halo-conversion"). This invention also relates to cyclic polypeptides having at least one polypeptide loop comprising a thioether linkage, and methods for their preparation which employ halogenated polypeptides and which involve intramolecular alkylation of the thiol group of a cysteine-like amino acid by the halo group of a haloalanine-like amino acid under suitable basic conditions to form a thioether linkage (i.e., "cyclization").

DESCRIPTION OF THE RELATED ART

Throughout this application, various publications, patents, and published patent applications are referred to by an identifying citation. The disclosures of the publications, patents, and published patent specifications referenced in this application are hereby incorporated by reference into the present disclosure to more fully describe the state of the art to which this invention pertains.

A thioether linkage has been widely utilized as a stable disulfide surrogate to replace the native disulfide bridges of bioactive cyclic peptides, such as hormones, neurotransmitters and neuromodulators, to prolong their biological activities (Lebl and Hruby, *Tetrahedron Lett.* (1984) 25:2067–2068; Polinsky et al., *J. Med. Chem.* (1992) 35:4185–4194; Mayer et al., *Tetrahedron Lett.* (1995) 36:7387–7390). The thioether linkage has also been used to prepare cyclic analogs of normally acyclic polypeptides to restrict their conformational mobility and thus to increase their biological activity and stability against biodegradation (Mosberg et al., *J. Am. Chem. Soc.* (1985) 107:2986–2987; Hruby et al., *Biochem. J.* (1990) 268:249–262; Kataoka et al., *Biopolymers* (1992) 32:1519–1533; Hruby and Bonner, *Methods in Molecular Biology* (1994) 35:201–240).

Additionally, thioether linked cyclic peptides have also been found in nature, especially in a family of polycyclic peptide antibiotics, lantibiotics, including nisin, an important food preservative, epidermin, a therapeutic agent against acne, as well as enzyme inhibitors and immunologically active peptides (Jung, G. *Angew. Chem. Int. Ed. Engl.* (1991) 30:1051–1192; Jack, R. W. and Sahl, H. G. *Trend in Biotechnology* (1995) 13:269–278; Sahl, H. G., Jack, R. W., and Bierbaum, G. *Eur. J. Biochem.* (1995) 230:827–853). Prominent structural features of all lantibiotics are intrachain sulfide bridges formed by thioether diaminodicarboxylic acids, lanthionines.

The conventional approach for the synthesis of thioether-linked cyclic peptides utilizes thioether diamino acids lanthionines (e.g., $H_2NCH(COOH)CH_2SCH_2CH(COOH)NH_2$) and cystathionines (e.g., $H_2NCH(COOH)CH_2SCH_2CH_2CH(COOH)NH_2$) as building blocks. The peptide cyclization is accomplished through the formation of an amide bond (Lebl and Hruby, *Tetrahedron Lett.* (1984) 25:2067–2068; Osapay and Goodman, *J. Chem. Soc. Chem. Commun.* (1993):1599–1600; Safar et al., in Peptides: Chemistry, Structure and Biology (Hodges, R. S. and Smith, J. A., Eds.) Escom, Leiden, The Netherlands, (1994) 119–120). This approach requires tedious and extensive synthesis of orthogonally protected lanthionine and cystathionine derivatives (Jost and Rudinger, *Collect. Czech. Chem. Commun.* (1967) 32:2485–2490; Cavelier-Frontin et al. *Tetrahedron Asymmetry* (1992) 3:85–94; Shao et al., *J. Org. Chem.* (1995) 60:2956–2957; Probert et al., *Tetrahedron Lett.* (1996) 37:1101–1104). Recently, Rolinsky and co-workers have reported a synthetic approach which featured an intramolecular Michael addition of the thiol group of a cysteine residue to an activated olefin to yield a lanthionine-containing peptide (Polinsky et al., *J. Med. Chem.* (1992) 35:4185–4194). However, this approach often yields two diastereomeric products due to the lack of stereospecificity of Michael addition reaction (Probert et al., *Tetrahedron Lett.* (1996) 37:1101–1104). Mayer and co-workers have described a route which relies upon an intramolecular substitution reaction of bromo group by the thiol group of cysteine residue to provide a cystathionine-containing peptide (Mayer et al., *Tetrahedron Lett.* (1995) 36:7387–7390). This approach is limited by the low coupling efficiency of the bromo amino acid in the peptide synthesis due to the competing intramolecular cyclization reaction. The thioether bridge can also be formed through reversible sulfur extrusion with tris(dialkyamino)phosphine (i.e., $P(NR_2)_3$) from the disulfide peptides in moderate yields (Fukase et al., *Bull. Chem. Soc. Jpn.* (1985) 59:2505–2508).

The present invention provides a general method for the halogenation of polypeptides. The present invention also provides a general method for the use of halogenated polypeptides in the formation of cyclic polypeptides comprising a thioether linkage. This synthetic method circumvents some of the limitations of earlier approaches and provides a robust method for the synthesis of thioether cyclic peptides.

This synthetic method may be used to build thioether constrained cyclic peptide libraries to develop novel enzyme inhibitors, and agonists and antagonists of bioactive molecules (Katz et al., *J. Am. Chem. Soc.* (1995) 117:8541–8547). More particularly, the lanthionine-containing library may be used to develop novel antimicrobial agents to combat antibiotic-resistant bacteria (Jung, *Angew. Chem. Int. Ed. Engl.* (1991) 30:1051–1192; Blondelle and Houghten, *Trends in Biotechnology* (1996) 14:60–65). The total synthesis of lantibiotics could also be greatly facilitated by the synthetic methods of the present invention.

The methods of the present invention may also be used to prepare conformationally restrained antigenic polypeptides. The cyclic thioether antigens can be used to conjugate with immunogenic protein carriers or annular antigen scaffolds or to build multiple antigen peptides (MAP) (Dintzis, *Pediatric Res.* (1992) 32:356–376; Tam, *Proc. Natl. Acad. Sci. USA.* (1988) 85:5409–5413; Cunningham et al., United Kingdom patent GB 2 282 813 (1995)). The peptide conjugates and multiple antigen peptides, which contain both a neutralizing B-cell epitope and a T-cell epitope, have been used as immunogens to effectively elicit vaccines against various infectious diseases such as influenza, hepatitis B, and acquired immune deficiency syndrome (AIDS) (Tam, in *Peptides: Synthesis, Structures, and Applications* (Gutte ed.) Academic Press, San Diego, (1995) 455–500; Cunningham et al., United Kingdom patent GB 2 282 815 (1995)).

In addition, the thioether cyclic antigens can be conjugated with multivalent non-immunogenic platforms (Liu et al., *Biochemistry* (1979) 18:690–697; Jones et al., *Bioconjugate. Chem.* (1994) 5:390–399; Jones et al.,*J. Med. Chem.* (1995) 38:2138–2144). These peptide conjugates contain only B-cell epitopes and could be used as toleragens for treatment of antibody-mediated autoimmune diseases such as systematic lupus nephritis, anti-phospholipid antibody mediated thromboses, myasthenia gravis, Graves' disease and Rh hemolytic disease of newborns (Barstard and Iverson, U.S. Pat. No. 5,268,454 (1993); Coutts et al., *Lupus* (1996)5:158–159).

One class of the cyclic polypeptides of the present invention, specifically, those with thioether-containing polypeptide loops of nine or fewer amino acids, or disulfide mimetics, bind to anticardiolipin antibody. These thioether cyclic polypeptides were derived from their parent disulfide cyclic antiphospholipid epitopes whose primary sequences were obtained from phage display library screening (Victoria and Marquis, U.S. patent application Ser. No. 08/482,651). Conjugates of these cyclic polypeptides may be used to suppress antiphospholipid antibodies to treat diseases such as recurrent stroke and recurrent fetal loss.

In addition to their applications in the synthesis of thioether cyclic peptides, halopolypeptides are useful in the development of therapeutic agents such as enzyme inhibitors (Cheung et al., *J. Med. Chem.* (1983) 26:1733–1741; Cheung et al., *J. Med. Chem.* (1986) 29:2060–2068) or diagnostic reagents.

SUMMARY OF THE INVENTION

One aspect of the present invention pertains to cyclic polypeptides having at least one polypeptide loop, said loop comprising a thioether linkage, said cyclic polypeptide represented by the formula (SEQ ID NO:1):

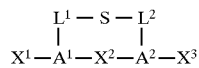

wherein S is a sulfur atom; $L^1$ and $L^2$ are independently divalent hydrocarbyl moieties of 1 to 10 carbon atoms; $A^1$ and $A^2$ are independently alpha amino acid fragments; $X^1$ is represented by the formula $J^N$—$(AA)_p$—; $X^2$ is represented by the formula —$(AA)_q$—; $X^3$ is represented by the formula —$(AA)_r$—$J^C$; wherein AA denotes an amino acid which may be in a protected form; $J^N$ is an N-terminal group; $J^C$ is a C-terminal group; and p, q, and r are independently whole numbers from 0 to 50. In a preferred embodiment, the cyclic polypeptide is represented by the formula (SEQ ID NO:1):

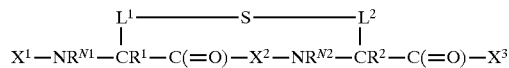

wherein S is a sulfur atom; C is a carbon atom; N is a nitrogen atom; O is an oxygen atom; $L^1$ and $L^2$ are independently divalent hydrocarbyl moieties of 1 to 10 carbon atoms; $R^1$ and $R^2$ are independently —H or an alkyl group having 1 to 6 carbon atoms; $R^1$ and $R^2$ are attached to carbon atoms, C, which independently have chirality R or S; $R^{N1}$ and $R^{N2}$ are independently —H or an alkyl group having 1 to 6 carbon atoms; $X^1$ is represented by the formula $J^N$— $(AA)_p$—; $X^2$ is represented by the formula —$(AA)_q$—; $X^3$ is represented by the formula —$(AA)_r$—$J^C$ wherein AA denotes an amino acid which may be in a protected form; $J^N$ is an N-terminal group; $J^C$ is a C-terminal group; and p, q, and r are independently whole numbers from 0 to 50. In another preferred embodiment, $L^1$ and $L^2$ are independently divalent alkyl moieties having from 1 to 6 carbon atoms, and more preferably independently selected from the group consisting of —$CH_2$—, —$CH_2CH_2$—, and —$CH_2CH_2CH_2$—. In another preferred embodiment, p, q, and r are independently whole numbers from 0 to 10. In another preferred embodiment, $R^1$ and $R^2$ are independently —H or —$CH_3$. In another preferred embodiment, $R^{N1}$ and $R^{N2}$ are independently —H or —$CH_3$.

Another aspect of the present invention pertains to halogenated polypeptides having at least one haloalanine-like amino acid, said halogenated polypeptide represented by the formula:

wherein $AA^H$ is a haloalanine-like amino acid; $Y^1$ is represented by the formula $J^N$—$(AA)_j$—; $Y^2$ is represented by the formula —$(AA)_k$—$J^C$ wherein AA denotes an amino acid which may be in a protected form; $J^N$ is an N-terminal group; $J^C$ is a C-terminal group; and j and k are independently whole numbers from 0 to 50, with the proviso that j+k is not zero. In a preferred embodiment, the halogenated polypeptide is represented by the formula:

wherein C is a carbon atom; N is a nitrogen atom; O is an oxygen atom; $R^H$ is a halogen-containing alkyl group comprising a halo group selected from the group consisting of —Cl, —Br, and —I; and an alkyl moiety of 1 to 10 carbon atoms; $R^B$ is —H or an alkyl group having 1 to 6 carbon atoms; $R^H$ and $R^B$ are attached to carbon atom, C, which has chirality R or S; $R^N$ is —H or an alkyl group having 1 to 6 carbon atoms; $Y^1$ is represented by the formula $J^N$—$(AA)_j$—; $Y^2$ is represented by the formula —$(AA)_k$—$J^C$; wherein AA denotes an amino acid which may be in a protected form; $J^N$ is an N-terminal group; $J^C$ is a C-terminal group; and j and k are independently whole numbers from 0 to 50, with the proviso that j+k is not zero. In another preferred embodiment, $R^H$ is a halogen-containing alkyl group represented by the formula —$(CH_2)_z X$ where z is a natural number from 1 to 10 and X is Cl, Br, or I; more preferably selected from the group consisting of —$CH_2Cl$, —$CH_2Br$, —$CH_2CH_2Cl$, and —$CH_2CH_2Br$. In another preferred embodiment, j and k are independently whole numbers from 0 to 10. In another preferred embodiment, $R^B$ is —H or —$CH_3$. In another preferred embodiment, $R^N$ is —H or —$CH_3$.

Yet another aspect of the present invention pertains to methods for the preparation of a cyclic polypeptide, said cyclic polypeptide having at least one polypeptide loop, said loop comprising a thioether linkage; from a reactant polypeptide, said reactant polypeptide having at least one cysteine-like amino acid, said cysteine-like amino acid having a thiol group, and at least one serine-like amino acid, said serine-like amino acid having an hydroxyl group; said method comprising the steps of: (a) converting said hydroxyl group of said serine-like amino acid to a halo group with the aid of a phosphorus-based halogenation reagent to yield a haloalanine-like amino acid, and thus form a halogenated polypeptide; and (b) intramolecularly reacting said halo group of said haloalanine-like amino acid of said halogenated polypeptide with said thiol group of said cysteine-like amino acid of said halogenated polypeptide under basic conditions to form said thioether linkage. In a preferred embodiment, said phosphorus-based halogenation reagent comprises a reagent selected from the group consisting of triphenylphosphine dihalide, triphenylphosphite dihalide, mixtures of triphenylphosphine and a halohydrocarbon compound, and mixtures of triphenylphosphite and a halohydrocarbon compound. In another preferred embodiment, said basic conditions are provided by the addition of sodium carbonate. In another preferred embodiment, said reactant polypeptide is provided in a dissolved form. In another preferred embodiment, said reactant polypeptide is provided in a supported form; said conversion step (a) is performed using said supported reactant polypeptide; said halogenated polypeptide produced in step (a) is cleaved from its support to yield a dissolved halogenated polypeptide, prior to carrying out step (b); and said reaction step (b) is performed using said dissolved halogenated polypeptide. In a preferred embodiment, said reactant polypeptide is provided in a supported form; said conversion step (a) is performed using said supported reactant polypeptide to yield a supported halogenated polypeptide; and said reaction step (b) is performed using said supported halogenated polypeptide.

Still another aspect of the present invention pertains to methods for the preparation of a halogenated polypeptide, said halogenated polypeptide having at least one haloalanine-like amino acid, said haloalanine-like amino acid having a halo group —X wherein X is Cl, Br, or I; from a reactant polypeptide, said reactant polypeptide having at least one serine-like amino acid, said serine-like amino acid having an hydroxyl group; said method comprising the step: (a) converting said hydroxyl group of said serine-like amino acid to a halo group with the aid of a phosphorus-based halogenation reagent to yield a haloalanine-like amino acid. In a preferred embodiment, said phosphorus-based halogenation reagent comprises a reagent selected from the group consisting of triphenylphosphine dihalide, triphenylphosphite dihalide, mixtures of triphenylphosphine and a halohydrocarbon compound, and mixtures of triphenylphosphite and a halohydrocarbon compound. In another preferred embodiment, a molar excess of said phosphorus-based halogenation reagent, in relation to said reactant polypeptide, is employed. In another preferred embodiment, said hydroxyl group of said serine-like amino acid is in a protected form; more preferably in a protected form as a tert-butyldimethylsilyl ether group. In another preferred embodiment, said reactant polypeptide is in a dissolved form. In another preferred embodiment, said reactant polypeptide is in a supported form.

As will become apparent, preferred features and characteristics of one aspect of the invention are applicable to any other aspect of the invention.

DESCRIPTION OF THE PREFERRED EMBODIMENTS

A. Cyclic Polypeptides

Figure 1:
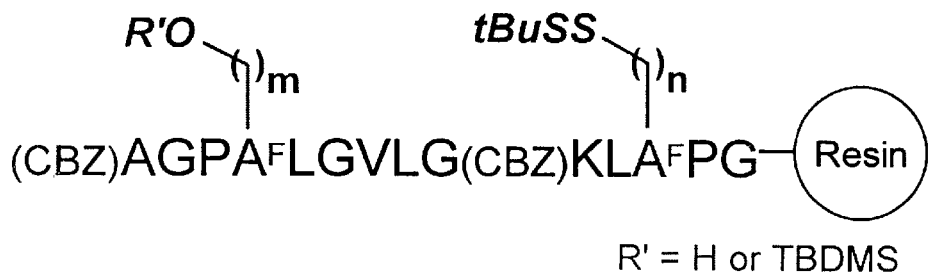
FIG. 1 illustrates a general synthetic strategy for a cyclic thioether polypeptide (SEQ ID NO:3).
Figure 1:
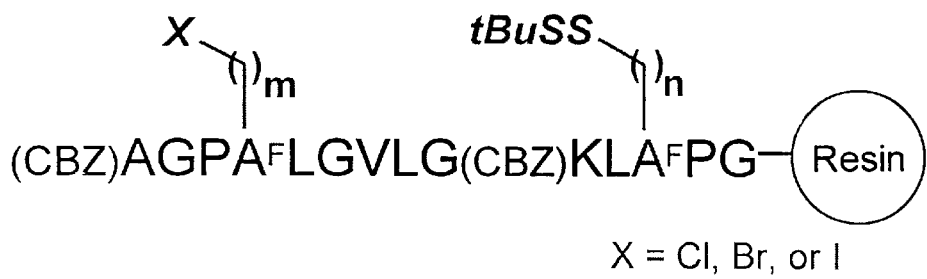
Figure 1:
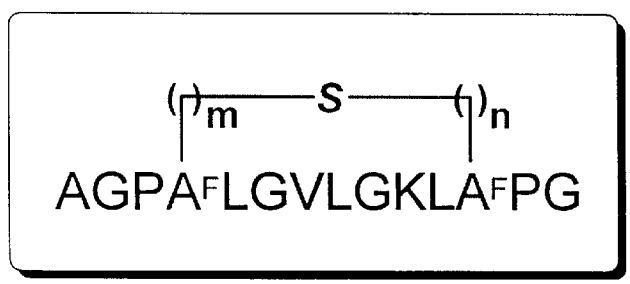
Figure 1:
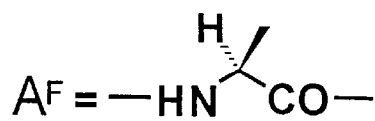

The present invention pertains to cyclic polypeptides having at least one polypeptide loop, wherein the polypeptide loop comprises a thioether linkage.

The term "polypeptide" is used herein in the conventional sense to refer to a polymer of amino acids. The repeating units of a polypeptide are derived from amino acids and are chemically linked via an amide linkage (i.e., a peptide linkage; —C(=O)NR$^N$—, where R$^N$ is a nitrogen substituent, often —H). Polypeptides may be linear, branched, or cyclic, as determined by the chain of contiguous atoms (i.e., the polypeptide backbone) which contains the peptide linkage atoms. The term "linear polypeptide" is used herein in the conventional sense to refer to a polypeptide in which the polypeptide backbone is linear. The term "branched polypeptide" is used herein in the conventional sense to refer to a polypeptide in which the polypeptide backbone comprises at least one polypeptide branch. The term "cyclic polypeptide" is used herein in the conventional sense to refer to a polypeptide in which the polypeptide backbone comprises at least one polypeptide loop.

The term "thioether linkage" is used herein in the conventional sense to refer to a chemical linkage between two hydrocarbyl groups which involves a single sulfur atom and is often denoted R—S—R.

Many of the cyclic polypeptides of the present invention may conveniently be represented by the following formulae (SEQ ID NO:1):

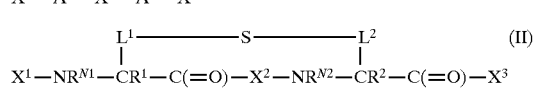

In the above formula (1), $A^1$ and $A^2$ denote amino acid fragments (often designated herein as $A^F$) to which both the thioether linkage (i.e., —L$^1$—S—L$^2$—) and the peptide fragment (i.e., —X$^2$—) are attached, thus forming a polypeptide loop. The amino acid fragments, $A^1$ and $A^2$, together with their associated linker moieties, L$^1$ and L$^2$, respectively, represent amino acid residues.

In the above formulae (I) and (II), L$^1$ and L$^2$ denote linker moieties and S denotes a sulfur atom joining the two linker moieties, thus forming a thioether linkage (i.e., L$^1$—S—L$^2$). The linker moieties L$^1$ and L$^2$ are independently divalent hydrocarbyl moieties. The term "hydrocarbyl moiety" is used herein in the conventional sense to refer to chemical moieties consisting of hydrogen (i.e., H) and carbon (i.e., C).

More preferably, the linker moieties $L^1$ and $L^2$ are independently divalent hydrocarbyl moieties having from 1 to 10 carbon atoms; still more preferably linear, cyclic, or branched divalent alkyl moieties having from 1 to 10 carbon atoms. Preferred linker moieties $L^1$ and $L^2$ are divalent alkyl moieties having from 1 to 6 carbon atoms, including, for example, —$CH_2$— (i.e., methylene), —$CH_2CH_2$— (i.e., ethylene), and —$CH_2CH_2CH_2$— (i.e., n-propylene). For convenience, the thioether linkage —$CH_2$—S—$CH_2$— is denoted herein as MMTE (i.e., methylene-methylene-thioether); the thioether linkage —$CH_2CH_2$—S—$CH_2$— is denoted herein as EMTE (i.e., ethylene-methylene-thioether); the thioether linkage —$CH_2$—S—$CH_2CH_2$— is denoted herein as METE (i.e., methylene-ethylene-thioether); and the thioether linkage —$CH_2CH_2$—S—$CH_2CH_2$— is denoted herein as EETE (i.e., ethylene-ethylene-thioether).

In the above formula (II), C, N and O denote carbon, nitrogen, and oxygen atoms, respectively, and $R^1$ and $R^2$ denote substituents which are independently —H or an organic substituent. In a preferred embodiment, $R^1$ and $R^2$ are independently —H or an alkyl group having 1 to 6 carbon atoms. In another preferred embodiment, $R^1$ and $R^2$ are independently —H or —$CH_3$. In still another preferred embodiment, both $R^1$ and $R^2$ are —H. The chiralities at these two carbons (i.e., denoted C with $R^1$ and $R^2$ substituents, respectively) are independently R or S.

In the above formula (II), $R^{N1}$ and $R^{N2}$ denote nitrogen substituents which may independently be —H or an organic substituent. Examples of organic substituents include those found in $N^\alpha$-alkyl alpha amino acids, such as alkyl groups having 1 to 6 carbon atoms, including for example, —$CH_3$. Other examples of organic substituents include those found in cyclic alpha amino acids, such as, for example, proline (i.e., Pro), tetrahydroisoquinolinecarboxylic acid (i.e., Tic) and tetrahydrocarbolinecarboxylic acid (i.e., Tca), as described below.

In some embodiments, one or more of the substituents $R^1$, $L^1$, and $R^{N1}$ may together form a single multivalent substituent. Similarly, one or more of the substituents $R^2$, $L^2$, and $R^{N2}$ may together form a single multivalent substituent. Thus, linker moieties may be multiply attached to the polypeptide. For example, when the amino acid $A^1$ (or $A^2$) is derived from an amino acid such as 4-mercaptoproline, the substituents $L^1$ and $R^{N1}$ together form a single trivalent substituent (i.e., —$CH_2CH$(—)$CH_2$—) which links the alpha carbon atom, the amino nitrogen atom, and the thioether sulfur atom. In another example, when the amino acid $A^1$ (or $A^2$) is derived from an amino acid such as 1-amino-3-mercapto-1-cyclopentane carboxylic acid (i.e., an analog of cyclic leucine, $Ac_5c$), the substituents $L^1$ and $R^1$ together form a single trivalent substituent (e.g.,—$CH_2CH$(—)$CH_2CH_2$—) which links the alpha carbon atom (twice) and the thioether sulfur atom.

In the above formula (I), $X^1$, $X^2$, $X^3$ are peptide fragments which may be represented by the formulae $J^N$—$(AA)_p$—, —$(AA)_q$—, and —$(AA)_r$—$J^C$, respectively, wherein AA denotes an amino acid; $J^N$ is an N-terminal group; $J^C$ is a C-terminal group; and p, q and r are independently whole numbers, preferably from 0 to about 50, more preferably from 0 to about 20, yet more preferably from 0 to about 10. The polypeptide fragments —$(AA)_p$—, —$(AA)_q$—, and —$(AA)_r$—, when present (i.e., when p, q, and/or r are non-zero), may independently be linear, branched, or cyclic, but preferably are linear. In a preferred embodiment, q is 7 or less and the polypeptide loop consists of nine or fewer amino acid residues. In a preferred embodiment, the amino acids, AA, are alpha amino acids. The amino acids, AA, may be in a protected form or an unprotected form.

The N-terminal group, $J^N$, identified above may be —H or a suitable terminal group. Examples of N-terminal groups, $J^N$, include —H (yielding a free amino group); carboxy groups (i.e., —C(=O)OR, yielding a carbamate group); and carbonyl groups (i.e., —C(=O)R; yielding an acyl amino group). Examples of carboxy groups include —Fmoc (i.e., 9-fluorenylmethyloxycarbonyl), —Boc (i.e., tert-butoxycarbonyl, —C(=O)OC($CH_3$)$_3$), —CBZ (i.e., benzyloxycarbonyl, —C(=O)O$CH_2C_6H_5$), and —2-Cl—CBZ (i.e., 2-chlorobenzyloxycarbonyl, —C(=O)O$CH_2C_6H_4Cl$). Examples of carbonyl groups include alkyl carbonyls of 1 to 10 carbon atoms, such as, acetyl (i.e., —C(=O)$CH_3$).

The C-terminal group, $J^C$, identified above may be —H or a suitable terminal group. Examples of C-terminal groups, $J^N$, include hydroxyl (i.e., —OH; yielding a free carboxylic acid group); alkoxy groups (i.e., —OR; yielding an ester group); amino groups (i.e., —$NH_2$, NHR, $NR_2$; yielding an amide group); and hydrazino groups (e.g., —$NHNH_2$; yielding a hydrazide group). Examples of alkoxy groups include alkoxy groups of 1 to 10 carbon atoms, such as methoxy (i.e., —$OCH_3$), ethoxy (i.e., —$OCH_2CH_3$), cyclohexyloxy (i.e., —OcHx; —$OC_6H_{11}$), tert-butoxy (i.e., —OC($CH_3$)$_3$); and benzyloxy (i.e., —$OCH_2C_6H_5$). Examples of amino groups include primary alkyl amino groups (i.e., —NHR; yielding a secondary amide group) and secondary alkyl amino groups (i.e., —$NR_2$; yielding a tertiary amide group) where R may independently be an alkyl group of 1 to 10 carbon atoms, such as methyl (i.e., —$CH_3$) and ethyl (i.e., —$CH_2CH_3$).

The term "amino acid" is used herein in the conventional sense to refer to an organic chemical species comprising at least one amino group (i.e., —$NH_2$ or —$NR^NH$) and at least one carboxylic acid group (i.e., —COOH). In some cases, an amino group may be a substituted amino group (i.e., —$NR^NH$, where $R^N$ is a nitrogen substituent), for example, as in the case of proline. For convenience, amino acids are often denoted herein as AA, or as H—AA—OH, where the initial —H is part of an amino group, and the final —OH is part of a carboxylic acid group. Amino acids may often be conveniently further classified according to their structure, for example, as alpha-amino acids, beta-amino acids, and the like.

The term "alpha amino acid" is used herein the conventional sense to refer to amino acids in which at least one carboxylic acid group (i.e., —COOH) and at least one amino group (i.e., —$NH_2$ or —$NR^NH$) are directly attached to a single carbon atom (designated the alpha carbon) and may be conveniently denoted $HNR^N$—$CR^AR^B$—COOH wherein $R^N$, $R^A$ and $R^B$ are substituents. Two or more of the substituents $R^N$, $R^A$ and $R^B$ may together form a single multivalent substituent. For example, in the cyclic alpha-amino acid proline, $R^N$ and $R^A$ together form the single divalent substituent —$CH_2CH_2CH_2$—, and $R^B$ is —H.

If the substituents $R^A$ and $R^B$ are different, the alpha carbon will be chiral (i.e., R or S), and the alpha-amino acid will be optically active. For example, glycine, for which $R^A$ and $R^B$ are both —H, is not optically active, whereas alanine, for which $R^A$ is —$CH_3$ and $R^B$ is —H, is optically active and may be in d- or l-forms, denoted d-alanine or l-alanine, respectively. The alpha carbon of d-alanine is in the R configuration whereas the alpha carbon of l-alanine is in the S configuration.

Of the wide variety of alpha-amino acids known, only about twenty are naturally occurring. Naturally occurring alpha-amino acids are often denoted HNR$^N$—CHR—COOH (since R$^B$ is —H) where R$^N$ denotes a nitrogen substituent and R denotes an amino acid substituent (often referred to as an amino acid sidechain). The nitrogen substituent R$^N$ is —H for all naturally occurring alpha amino acids, with the exception of proline (where R$^N$ and R together form the divalent substituent —CH$_2$CH$_2$CH$_2$—). Except for glycine, all of these twenty naturally occurring alpha-amino acids are optically active and are in the l-form. Examples of amino acid substituents include those substituents found in the twenty naturally occurring alpha-amino acids, such as, for example, —H (for glycine), —CH$_3$ (for alanine), —CH$_2$OH (for serine), —CH(CH$_3$)OH (for threonine), —CH$_2$SH (for cysteine), and —CH$_2$C$_6$H$_5$ (for phenylalanine). Other examples of amino acid substituents include those which are structurally similar to those substituents found in the naturally occurring amino acids, such as, for example, —CH$_2$CH$_2$OH (for homoserine) and —CH$_2$CH$_2$SH (for homocysteine).

For convenience, the naturally occurring amino acids are often represented by a three-letter code or a one-letter code. For example, cysteine is often abbreviated as H—Cys—OH, or H—C—OH, and serine is often abbreviated as H—Ser—OH or H—S—OH wherein the —H group is part of the amino group (i.e., —NH$_2$ or —NR$^N$H) and the —OH group is part of the carboxylic acid group (i.e., —COOH). Often the —H and —OH groups are omitted for the sake of simplicity, as in, for example Cys, C; and Ser, S. Three-letter and one-letter codes for the twenty naturally occurring acids are well established in the art, and the same convention is used herein. As used herein, the corresponding "one-letter code" for homoserine is Hs and the corresponding "one-letter code" for homocysteine is Hc.

In addition to an alpha carboxylic acid group (i.e., —COOH) and an alpha amino group (i.e., —NH$_2$ or —NR$^N$H), many amino acids have additional functional groups. Lysine, for which the amino acid substituent, R, is —(CH$_2$)$_4$NH$_2$, has an additional amino group (i.e., —NH$_2$). Aspartic acid and glutamic acid, for which the amino acid substituents, R, are —CH$_2$COOH and —(CH$_2$)$_2$COOH, respectively, each have an additional carboxylic acid group (i.e., —COOH). Serine, for which the amino acid substituent, R, is —CH$_2$OH, has an additional primary hydroxyl group (i.e., —OH). Threonine, for which the amino acid substituent, R, is —CH(CH$_3$)OH, has an additional secondary hydroxyl group (i.e., —OH). Cysteine, for which the amino acid substituent, R, is —CH$_2$SH, has an additional thiol group (i.e., —SH). Other amino acids have other additional functional groups, including, for example, thioether groups (e.g., in methionine), phenol groups (e.g., in tyrosine), amide groups (e.g., in glutamine), and heterocylic groups (e.g., in histidine).

In addition to the twenty naturally occurring amino acids, several other classes of alpha amino acids are also known. Examples of these other classes include d-amino acids, N$^a$-alkyl amino acids, alpha-alkyl amino acids, cyclic amino acids, chimeric amino acids, and miscellaneous amino acids. These non-natural amino acids have been widely used to modify bioactive polypeptides to enhance resistance to proteolytic degradation and/or to impart conformational constraints to improve biological activity (Hruby et al., *Biochem. J.* (1990) 268:249–262; Hruby and Bonner, *Methods in Molecular Biology* (1994) 35:201–240). The most common N$^a$-alkyl amino acids are the N$^a$-methyl amino acids, such as, N$^a$-methyl glycine (i.e., N$^a$MeGly), N$^a$-methyl alanine (i.e., N$^a$MeAla), and N$^a$-methyl lysine (i.e., N$^a$MeLys). Examples of alpha-alkyl amino acids include alpha-aminoisobutyric acid (i.e., Aib), diethylglycine (i.e., Deg), diphenylglycine (i.e., Dpg), alpha-methyl proline (i.e., (αMe)Pro), and alpha-methyl valine (i.e., (αMe)Val) (Balaram, *Pure & Appl. Chem.* (1992) 64:1061–1066; Toniolo et al., *Biopolymers* (1993) 33:1061–1072; Hinds et al., *J. Med. Chem.* (1991) 34:1777–1789). Examples of cyclic amino acids include 1-amino-1-cyclopropane carboxylic acid (i.e., Ac$_3$c), 1-amino-1-cyclopentane carboxylic acid (i.e., cyclic leucine, Ac$_5$c), aminoindane carboxylic acid (i.e., Ind), tetrahydroisoquinolinecarboxylic acid (i.e., Tic) and tetrahydrocarbolinecarboxylic acid (i.e., Tca) (Toniolo, C., *Int. J. Peptide Protein Res.* (1990) 35:287–300; Burgess, K., Ho, K. K., and Pal, B. *J. Am. Chem. Soc.* (1995) 117:3808–3819). Examples of chimeric amino acids include penicillamine (i.e., Pen), combination of cysteine with valine, and 4-mercaptoproline (i.e., Mpt), combination of proline and homocysteine. Example of miscellaneous alpha-amino acids include ornithine (i.e., Orn), 2-naphthylalanine (i.e., 2-Nal), phenylglycine (i.e., Phg), t-butylglycine (i.e., tBug), cyclohexylalanine (i.e., Cha), and alpha-amino-2-thiophenepropionic acid (i.e., Thi). In addition to alpha-amino acids, others such as beta amino acids, can also be used in the present invention. Examples of these other amino acids include 2-aminobenzoic acid (i.e., Abz), β-aminopropanoic acid (i.e., β-Apr), γ-aminobutyric acid (i.e., γ-Abu), and 6-aminohexanoic acid (i.e., ε-Ahx).

In the synthesis and manipulation of amino acid-containing species (e.g., polypeptides), it is often necessary to "protect" certain functional groups (such as alpha-amino groups, alpha-carboxylic acid groups, and side-chain functional groups) of amino acids. A wide variety of protecting groups and strategies are known in the art. For example, an alpha-amino group (i.e., —NH$_2$) may be protected with a 9-fluorenylmethyloxycarbonyl group (i.e., Fmoc; as —NHFmoc), a tert-butoxycarbonyl group (i.e., —C(=O)OC(CH$_3$)$_3$, Boc; as —NHBoc), or a benzyloxycarbonyl group (i.e., —C(=O)OCH$_2$C$_6$H$_5$, CBZ; as —NHCBZ). The guanidino group of arginine (i.e., —NHC(=NH)NH$_2$) may be protected with a 2,2,5,7,8-pentamethylchroman-6-sulfonyl group (i.e., Pmc; as —NHC(=NH)—NH—Pmc), a 4-methoxy-2,3,6-trimethylbenzenesulfonyl group (i.e., Mtr; as —NHC(=NH)—NH—Mtr), or a mesitylene-2-sulfonyl group (i.e., Mts; as —NHC(=NH)—NH—Mts). The carboxamide groups of asparagine and glutamine (i.e., —CONH$_2$) may be protected with a trityl group (i.e., —C(C$_6$H$_5$)$_3$, Tr; as —CONHTr). The side chain carboxylic acid groups of aspartic and glutamic acid may be protected with a t-butyl group (i.e., —C(CH$_3$)$_3$, tBu; as —COOtBu) or a cyclohexyl group (i.e., —C$_6$H$_{11}$, cHx; as —COOcHx). Additionally, carboxylic acid groups, such as terminal carboxylic acid groups, may be protected with a methyl group (i.e., —CH$_3$, as —COOCH$_3$), an ethyl group (i.e., —CH$_2$CH$_3$, as —COOCH$_2$CH$_3$), or a benzyl group (i.e., —CH$_2$C$_6$H$_5$, as —COOCH$_2$C$_6$H$_5$). The thiol group of cysteine (i.e., —SH) may be protected with a t-butylthio group (i.e., —SC(CH$_3$)$_3$, tBuS; as —SStBu) or a trityl group (i.e., —C(C$_6$H$_5$)$_3$, Tr; as —STr). The imidazole group of histidine may be protected with a trityl group (i.e., —C(C$_6$H$_5$)$_3$, Tr). The epsilon-amino group of lysine (i.e., NH$_2$) may be protected with a tert-butoxycarbonyl group (i.e., —C(=O)OC(CH$_3$)$_3$, Boc as —NHBoc), a benzyloxycarbonyl group (i.e., —C(=O)OCH$_2$C$_6$H$_5$, CBZ; as —NHCBZ), or a 2-chlorobenzyloxycarbonyl group (i.e., —C(=O)OCH$_2$C$_6$H$_4$Cl, 2-Cl—CBZ; as —NH—2-Cl—CBZ). The hydroxyl groups of homoserine, serine and threonine (i.e., —OH) may be protected with a t-butyl group (i.e., —C(CH$_3$)$_3$, tBu; as —OtBu), a trityl group (i.e., —C(C$_6$H$_5$)$_3$, Tr; as —OTr), or a t-butyldimethylsilyl group (i.e., —Si(CH$_3$)$_2$(C(CH$_3$)$_3$), TBDMS; as —OTBDMS). The indole nitrogen of tryptophan may be protected with a trityl group (i.e., —C(C$_6$H$_5$)$_3$, Tr). The hydroxyl group of tyrosine (i.e., —OH) may be protected with a trityl group (i.e., —C(C$_6$H$_5$)$_3$, Tr; as —OTr).

The peptide linkage (i.e., —C(=O)—NRN—) of a polypeptide may conveniently be considered to be the chemical linkage formed by reacting a carboxylic acid group (i.e., —COOH) of one amino acid with an amino group (i.e., —NR$^N$H) of another amino acid. In this way, a polypeptide (e.g., a "2-mer") of the two amino acids serine and cysteine (wherein the carboxylic acid group of serine and the amino group of cysteine have formed a peptide linkage) may conveniently be represented as H—Ser—Cys—OH or H—S—C—OH, or, more simply, as Ser—Cys, S—C, or SC. The amino acid moieties of a polypeptide are often referred to as amino acid residues.

Examples of preferred cyclic polypeptides of the present invention include those represented by formula (II) above which are thioether analogs of the disulfide polypeptide AGPCLGVLGKLCPG (denoted 3G3 (SEQ ID NO:2)) and wherein:

$X^1$ is Ala-Gly-Pro- (i.e., AGP— and p is 3); $X^2$ is -Leu-Gly-Val-Leu-Gly-Lys-Leu- (i.e., —LGVLGKL— and q is 7); $X^3$ is -Pro-Gly (i.e., —PG and r is 2); $L^1$ is —CH$_2$—; $L^2$ is —CH$_2$—; $R^1$ is —H; and $R^2$ is —H (denoted herein as compound 3G3-MMTE (SEQ ID NO:3)). The chirality of the carbon with substituent $R^1$ is mixed in d- and l-forms. The chirality of the carbon with the substituent $R^2$ is in the l-form.

$X^1$ is Ala-Gly-Pro- (i.e., AGP— and p is 3); $X^2$ is -Leu-Gly-Val-Leu-Gly-Lys-Leu- (i.e., —LGVLGKL— and q is 7); $X^3$ is -Pro-Gly (i.e., —PG and r is 2); $L^1$ is —CH$_2$CH$_2$—; $L^2$ is —CH$_2$—; $R^1$ is —H; and $R^2$ is —H (denoted herein as compound 3G3-EMTE (SEQ ID NO:4)). The chiralities of the carbons with substituents $R^1$ and $R^2$ are in the l-form.

$X^1$ is Ala-Gly-Pro- (i.e., AGP— and p is 3); $X^2$ is -Leu-Gly-Val-Leu-Gly-Lys-Leu- (i.e., —LGVLGKL— and q is 7); $X^3$ is -Pro-Gly (i.e., —PG and r is 2); $L^1$ is —CH$_2$—; $L^2$ is —CH$_2$CH$_2$—; $R^1$ is —H; and $R^2$ is —H (denoted herein as compound 3G3-METE (SEQ ID NO:5)). The chiralities of the carbons with substituents $R^1$ and $R^2$ are in the l-form.

$X^1$ is Ala-Gly-Pro- (i.e., AGP— and p is 3); $X^2$ is -Leu-Gly-Val-Leu-Gly-Lys-Leu- (i.e., —LGVLGKL— and q is 7); $X^3$ is -Pro-Gly (i.e., —PG and r is 2); $L^1$ is —CH$_2$CH$_2$—; $L^2$ is —CH$_2$CH$_2$—; $R^1$ is —H; and $R^2$ is —H (denoted herein as compound 3G3-EETE (SEQ ID NO:6)). The chiralities of the carbons with substituents $R^1$ and $R^2$ are in the l-form.

Examples of preferred cyclic polypeptides of the present invention include those represented by formula (II) above which are thioether analogs of the disulfide polypeptide GPCLGVLGKLCPG (denoted 2G3 (SEQ ID NO:7)) and wherein:

$X^1$ is Gly-Pro- (i.e., GP— and p is 2); $X^2$ is -Leu-Gly-Val-Leu-Gly-Lys-Leu- (i.e., —LGVLGKL— and q is 7); $X^3$ is -Pro-Gly (i.e., —PG and r is 2); $L^1$ is —CH$_2$—; $L^2$ is —CH$_2$—; $R^1$ is —H; and $R^2$ is —H (denoted herein as compound 2G3-MMTE (SEQ ID NO:8)). The chirality of the carbon with substituent $R^1$ is mixed in d- and l-forms. The chirality of the carbon with the substituent $R^2$ is in the l-form.

$X^1$ is Gly-Pro- (i.e., GP— and p is 2); $X^2$ is -Leu-Gly-Val-Leu-Gly-Lys-Leu- (i.e., —LGVLGKL— and q is 7); $X^3$ is -Pro-Gly (i.e., —PG and r is 2); $L^1$ is —CH$_2$CH$_2$—; L is —CH$_2$—; $R^1$ is —H; and $R^2$ is —H (denoted herein as compound 2G3-EMTE (SEQ ID NO:9)). The chiralities of the carbons with substituents $R^1$ and $R^2$ are in the l-form.

$X^1$ is Gly-Pro- (i.e., GP— and p is 2); $X^2$ is -Leu-Gly-Val-Leu-Gly-Lys-Leu- (i.e., —LGVLGKL— and q is 7); $X^3$ is -Pro-Gly (i.e., —PG and r is 2); $L^1$ is —CH$_2$—; L is —CH$_2$CH$_2$—; $R^1$ is —H; and $R^2$ is —H (denoted herein as compound 2G3-METE (SEQ ID NO:10)). The chirality of the carbon with substituent $R^1$ is in the d- or l-form. The chirality of the carbon with the substituent $R^2$ is in the l-form.

$X^1$ is Gly-Pro- (i.e., GP— and p is 2); $X^2$ is -Leu-Gly-Val-Leu-Gly-Lys-Leu- (i.e., —LGVLGKL— and q is 7); $X^3$ is -Pro-Gly (i.e., —PG and r is 2); $L^1$ is —CH$_2$CH$_2$—; $L^2$ is —CH$_2$CH$_2$—; $R^1$ is —H; and $R^2$ is —H (denoted herein as compound 2G3-EETE (SEQ ID NO:11)). The chiralities of the carbons with substituents $R^1$ and $R^2$ are in the l-form.

Examples of preferred cyclic polypeptides of the present invention include those represented by formula (II) above which are thioether analogs of the disulfide polypeptide CLGVLGKLC (denoted G3 (SEQ ID NO:12)) and wherein:

$X^1$ is H— (i.e., p is 0); $X^2$ is —Leu-Gly-Val-Leu-Gly-Lys-Leu— (i.e., —LGVLGKL— and q is 7); $X^3$ is —NH$_2$ (i.e., r is 0); $L^1$ is —CH$_2$; $L^2$ is —CH$_2$—; $R^1$ is —H; and $R^2$ is —H (denoted herein as compound G3-MMTE (SEQ ID NO:13)). The chirality of the carbon with substituent $R^1$ is mixed in d- and l-forms. The chirality of the carbon with the substituent $R^2$ is in the l-form.

$X^1$ is H— (i.e., p is 0); $X^2$ is —Leu-Gly-Val-Leu-Gly-Lys-Leu— (i.e., —LGVLGKL— and q is 7); $X^3$ is —NH$_2$ (i.e., r is 0); $L^1$ is —CH$_2$CH$_2$—; $L^2$ is —CH$_2$—; $R^1$ is —H; and $R^2$ is —H (denoted herein as compound G3-EMTE (SEQ ID NO:14)). The chiralities of the carbons with substituents $R^1$ and $R^2$ are in the l-form.

$X^1$ is H— (i.e., p is 0); $X^2$ is —Leu-Gly-Val-Leu-Gly-Lys-Leu— (i.e., —LGVLGKL— and q is 7); $X^3$ is —NH$_2$ (i.e., r is 0); $L^1$ is —CH$_2$—; $L^2$ is —CH$_2$CH$_2$—; $R^1$ is —H; and $R^2$ is —H (denoted herein as compound G3-METE (SEQ ID NO:15)). The chiralities of the carbons with substituents $R^1$ and $R^2$ are in the l-form.

$X^1$ is H— (i.e., p is 0); $X^2$ is —Leu-Gly-Val-Leu-Gly-Lys-Leu— (i.e., —LGVLGKL— and q is 7); $X^3$ is —NH$_2$ (i.e., r is 0); $L^1$ is —CH$_2$CH$_2$—; $L^2$ is —CH$_2$CH$_2$—; $R^1$ is —H; and $R^2$ is —H (denoted herein as compound G3-EETE (SEQ ID NO:16)). The chiralities of the carbons with substituents $R^1$ and $R^2$ are in the l-form.

Examples of preferred cyclic polypeptides of the present invention include those represented by formula (II) above which are thioether analogs of the disulfide polypeptide CLGVLAKLC (denoted AG3 (SEQ ID NO:17)) and wherein:

$X^1$ is H— (i.e., p is 0); $X^2$ is —Leu-N$^\alpha$MeGly-d-Val-d-Leu-Ala-Lys-Leu— (i.e., —L(N$^\alpha$Me—G)(d-V)(d-L)AKL— and q is 7); $X^3$ is —NH$_2$ (i.e., r is 0); $L^1$ is —CH$_2$—; $L^2$ is —CH$_2$—; $R^1$ is —H; and $R^2$ is —H (denoted herein as compound AG3-MMTE (SEQ ID NO:18)). The chirality of the carbon with substituent $R^1$ is mixed in d- and l-forms. The chirality of the carbon with the substituent $R^2$ is in the l-form.

X$^1$ is H— (i.e., p is 0); X$^2$ is —Leu-N$^a$MeGly-d-Val-d-Leu-Ala-Lys-Leu— (i.e., —L(N$^a$Me—G)(d-V)(d-L)AKL— and q is 7); X$^3$ is —NH$_2$ (i.e., r is 0); L$^1$ is —CH$_2$CH$_2$—; L$^2$ is —CH$_2$—; R$^1$ is —H; and R$^2$ is —H (denoted herein as compound AG3-EMTE (SEQ ID NO:19)). The chiralities of the carbons with substituents R$^1$ and R$^2$ are in the l-form.

X$^1$ is H— (i.e., p is 0); X$^2$ is —Leu-N$^a$MeGly-d-Val-d-Leu-Ala-Lys-Leu— (i.e., —L(N$^a$Me—G)(d-V)(d-L)AKL— and q is 7); X$^3$ is —NH$_2$ (i.e., r is 0); L$^1$ is —CH$_2$—; L$^2$ is —CH$_2$CH$_2$—; R$^1$ is —H; and R$^2$ is —H (denoted herein as compound AG3-METE (SEQ ID NO:20)). The chiralities of the carbons with substituents R$^1$ and R$^2$ are in the l-form.

X$^1$ is H— (i.e., p is 0); X$^2$ is —Leu-N$^a$MeGly-d-Val-d-Leu-Ala-Lys-Leu— (i.e., —L(N$^a$Me—G)(d-V)(d-L)AKL— and q is 7); X$^3$ is —NH$_2$ (i.e., r is 0); L$^1$ is —CH$_2$CH$_2$—; L$^2$ is —CH$_2$CH$_2$—; R$^1$ is —H; and R$^2$ is —H (denoted herein as compound AG3-EETE (SEQ ID NO:21)). The chiralities of the carbons with substituents R$^1$ and R$^2$ are in the l-form.

Examples of preferred cyclic polypeptides of the present invention include those represented by formula (II) above which are thioether analogs of the disulfide polypeptide GPCLILAPDRC (denoted CB10 (SEQ ID NO:22)) and wherein:

X$^1$ is Gly-Pro- (i.e., GP— and p is 2); X$^2$ is —Leu-Ile-Leu-Ala-Pro-Asp-Arg— (i.e., —LILAPDR— and q is 7); X$^3$ is —NH$_2$ (i.e., r is 0); L$^1$ is —CH$_2$—; L$^2$ is —CH$_2$—; R$^1$ is —H; and R$^2$ is —H (denoted herein as compound CB10-MMTE (SEQ ID NO:23)). The chirality of the carbon with substituent R$^1$ is mixed in d- and l-forms. The chirality of the carbon with the substituent R$^2$ is in the l-form.

X$^1$ is Gly-Pro- (i.e., GP— and p is 2); X$^2$ is —Leu-Ile-Leu-Ala-Pro-Asp-Arg— (i.e., —LILAPDR— and q is 7); X$^3$ is —NH$_2$ (i.e., r is 0); L$^1$ is —CH$_2$CH$_2$—; L$^2$ is —CH$_2$—; R$^1$ is —H; and R$^2$ is —H (denoted herein as compound CB10-EMTE (SEQ ID NO:24). The chiralities of the carbons with substituents R$^1$ and R$^2$ are in the l-form.

X$^1$ is Gly-Pro- (i.e., GP— and p is 2); X$^2$ is —Leu-Ile-Leu-Ala-Pro-Asp-Arg— (i.e., —LILAPDR— and q is 7); X$^3$ is —NH$_2$ (i.e., r is 0); L$^1$ is —CH$_2$—; L$^2$ is —CH$_2$CH$_2$—; R$^1$ is —H; and R$^2$ is —H (denoted herein as compound CB10-METE (SEQ ID NO:25)). The chiralities of the carbons with substituents R$^1$ and R$^2$ are in the l-form.

X$^1$ is Gly-Pro- (i.e., GP— and p is 2); X$^2$ is —Leu-Ile-Leu-Ala-Pro-Asp-Arg— (i.e., —LILAPDR— and q is 7); X$^3$ is —NH$_2$ (i.e., r is 0); L$^1$ is —CH$_2$CH$_2$—; L$^2$ is —CH$_2$CH$_2$—; R$^1$ is —H; and R$^2$ is —H (denoted herein as compound CB10-EETE (SEQ ID NO:26)). The chiralities of the carbons with substituents R$^1$ and R$^2$ are in the l-form.

B. Halogenated Polypeptides

The present invention also pertains to halogenated polypeptides having at least one haloalanine-like amino acid, said haloalanine-like amino acid having a halo group. The halogenated polypeptides may be in free form (e.g., as a solid or in solution) or may be in a supported form (e.g., attached to a support material).

The term "haloalanine-like amino acid" is used herein to refer to alpha amino acids which may be represented by the formula HNR$^N$—CR$^H$R$^B$—COOH (as the free amino acid) or as —NR$^N$—CR$^H$R$^B$—C(=O)— (when part of a polypeptide chain), where R$^N$, R$^H$ and R$^B$ are substituents. The substituents R$^N$ and R$^B$ are as defined above for R$^{N1}$/R$^{N2}$ and R$^1$/R$^2$, respectively, and are independently —H or an organic substituent. Two or more of the substituents R$^N$, R$^H$ and R$^B$ may together form a single multivalent substituent. The substituent R$^H$ (or a single multivalent substituent incorporating R$^H$ and one or more of R$^N$ and R$^B$) is a halogen-containing group. The term "halogen-containing group" is used herein to refer to organic moieties which comprise a halo group (i.e., —X wherein X is Cl, Br, or I). The alpha carbon of the haloalanine-like amino acid may have chirality R or S.

In some preferred embodiments, R$^H$ is a halogen-containing alkyl group. The term "halogen-containing alkyl group" is used herein to refer to organic moieties which comprise a halo group (i.e., —X wherein X is Cl, Br, or I) and an alkyl moiety. Examples of preferred halo groups are the bromo group (i.e., —Br) and the chloro group (i.e., —Cl). The alkyl moiety preferably comprises from 1 to 10 carbon atoms, more preferably 1 to 5 carbon atoms, still more preferably 1 to 3 carbon atoms, most preferably 1 to 2 carbon atoms. The alkyl moiety may be linear, cyclic, or branched, but is preferably linear. Examples of preferred halo-containing alkyl groups include those of the general formula —(CH$_2$)$_z$X where z is a natural number from 1 to 10, more preferably 1 to 5, still more preferably 1 to 3, most preferably 1 to 2, and X is Cl, Br, or I. Examples of preferred halo-containing alkyl groups include —CH$_2$Cl, —CH$_2$Br, —CH$_2$CH$_2$Cl, and —CH$_2$CH$_2$Br. Examples of other preferred halo-containing alkyl groups include —CH(CH$_3$)Cl and —CH(CH$_3$)Br.

Many of the halogenated polypeptides of the present invention may conveniently be represented by the following formulae:

Y$^1$—AA$^H$—Y$^2$ (III)

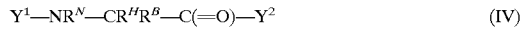

Y$^1$—NR$^N$—CR$^H$R$^B$—C(=O)—Y$^2$ (IV)

In the above formulae (III) and (IV), C, N, and O denote carbon, nitrogen, and oxygen atoms, respectively; AA$^H$ denotes a haloalanine-like amino acid as described above; and Y$^1$ and Y$^2$ denote peptide fragments. Y$^1$ and Y$^2$ may be conveniently represented by the formulae J$^N$—(AA)$_j$— and —(AA)$_k$—J$^C$, respectively, wherein AA denotes an amino acid; J$^N$ is an N-terminal group as defined above; J$^C$ is a C-terminal group as defined above; and j and k are independently whole numbers, preferably from 0 to about 50, more preferably from 0 to about 20, yet more preferably from 0 to about 10; with the proviso that j+k is not zero. The peptide fragments —(AA)$_j$— and —(AA)$_k$—, when present (i.e., when j and/or k are non-zero), may independently be linear, branched, or cyclic, but preferably are linear. In some preferred embodiments, the amino acids, AA, are alpha amino acids. The amino acids, AA, may be in a protected form or an unprotected form.

Examples of preferred halogenated polypeptides of the present invention include those represented by formula (IV) above which effectively comprise haloanalogs of the polypeptide AGPSLGVLGKLCPG (denoted X-3G3 (SEQ ID NO:27)) and wherein:

Y$^1$ is Ala-Gly-Pro- (i.e., AGP— and j is 3); Y$^2$ is —Leu-Gly-Val-Leu-Gly-Lys-Leu-Cys-Pro-Gly— (i.e., —LGVLGKLCPG— and k is 10); R$^H$ is —CH$_2$X, wherein X is Cl, Br, or I; and R$^B$ is —H (SEQ ID NO:28). The chirality of the carbon with substituents R$^H$ and R$^B$ is in the l-form.

Y¹ is Ala-Gly-Pro- (i.e., AGP— and j is 3); Y² is —Leu-Gly-Val-Leu-Gly-Lys-Leu-Cys-Pro-Gly— (i.e., —LGVLGKLCPG— and k is 10); $R^H$ is —CH$_2$CH$_2$X, wherein X is Cl, Br, or I; and $R^B$ is —H (SEQ ID NO:29). The chirality of the carbon with substituents $R^H$ and $R^B$ is in the l-form.

Y¹ is Ala-Gly-Pro- (i.e., AGP— and j is 3); Y² is —Leu-Gly-Val-Leu-Gly-Lys-Leu-homocysteine-Pro-Gly— (i.e., —LGVLGKLHcPG— and k is 10); $R^H$ is —CH$_2$X, wherein X is Cl, Br, or I; and $R^B$ is —H (SEQ ID NO:30). The chirality of the carbon with substituents $R^H$ and $R^b$ is in the l-form.

Y¹ is Ala-Gly-Pro- (i.e., AGP— and j is 3); Y² is —Leu-Gly-Val-Leu-Gly-Lys-Leu-homocysteine-Pro-Gly— (i.e., —LGVLGKLHcPG— and k is 10); $R^H$ is —CH$_2$CH$_2$X, wherein X is Cl, Br, or I; and $R^B$ is —H (SEQ ID NO:31). The chirality of the carbon with substituents $R^H$ and $R^B$ is in the l-form.

Examples of preferred halogenated polypeptides of the present invention include those represented by formula (IV) above which effectively comprise haloanalogs of the polypeptide GPSLGVLGKLCPG (denoted X-2G3 (SEQ ID NO:32)) and wherein:

Y¹ is Gly-Pro- (i.e., GP— and j is 2); Y² is —Leu-Gly-Val-Leu-Gly-Lys-Leu-Cys-Pro-Gly— (i.e., —LGVLGKLCPG— and k is 10); $R^H$ is —CH$_2$X, wherein X is Cl, Br, or I; and $R^B$ is —H (SEQ ID NO:33). The chirality of the carbon with substituents $R^H$ and $R^B$ is in the l-form.

Y¹ is Gly-Pro- (i.e., GP— and j is 2); Y² is —Leu-Gly-Val-Leu-Gly-Lys-Leu-Cys-Pro-Gly— (i.e., —LGVLGKLCPG— and k is 10); $R^H$ is —CH$_2$CH$_2$X, wherein X is Cl, Br, or I; and $R^B$ is —H (SEQ ID NO:34). The chirality of the carbon with substituents $R^H$ and $R^B$ is in the l-form.

Y¹ is Gly-Pro- (i.e., GP— and j is 2); Y² is —Leu-Gly-Val-Leu-Gly-Lys-Leu-homocysteine-Pro-Gly— (i.e., —LGVLGKLHcPG— and k is 10); $R^H$ is —CH$_2$X, wherein X is Cl, Br, or I; and $R^B$ is —H (SEQ ID NO:35). The chirality of the carbon with substituents $R^H$ and $R^B$ is in the l-form.

Y¹ is Gly-Pro- (i.e., GP— and j is 2); Y² is —Leu-Gly-Val-Leu-Gly-Lys-Leu-homocysteine-Pro-Gly— (i.e., —LGVLGKLHcPG— and k is 10); $R^H$ is —CH$_2$CH$_2$X, wherein X is Cl, Br, or I; and $R^B$ is —H (SEQ ID NO:36). The chirality of the carbon with substituents $R^H$ and $R^B$ is in the l-form.

Y¹ is Gly-Pro-Cys-Leu-Gly-Val-Leu-Gly-Lys-Leu- (i.e., GPCLGVLGKL— and j is 10); Y² is -Pro-Gly (i.e., —PG and k is 2); $R^H$ is —CH$_2$CH$_2$X, wherein X is Cl, Br, or I; and $R^B$ is —H (SEQ ID NO:37). The chirality of the carbon with substituents $R^H$ and $R^B$ is in the l-form.

Examples of preferred halogenated polypeptides of the present invention include those represented by formula (IV) above which effectively comprise haloanalogs of the polypeptide SLGVLGKLC (denoted X-G3 (SEQ ID NO:38)) and wherein:

Y¹ is H— (i.e., j is 0); Y² is —Leu-Gly-Val-Leu-Gly-Lys-Leu-Cys—NH$_2$ (i.e., —LGVLGKLC—NH$_2$ and k is 8); $R^H$ is —CH$_2$X, wherein X is Cl, Br, or I; and $R^B$ is —H (SEQ ID NO:40). The chirality of the carbon with substituents $R^H$ and $R^B$ is in the l-form.

Y¹ is H— (i.e., j is 0); Y² is —Leu-Gly-Val-Leu-Gly-Lys-Leu-Cys—NH$_2$ (i.e., —LGVLGKLC—NH$_2$ and k is 8); $R^H$ is —CH$_2$CH$_2$X, wherein X is Cl, Br, or I; and $R^B$ is —H (SEQ ID NO:40). The chirality of the carbon with substituents $R^H$ and $R^B$ is in the l-form.

Y¹ is H— (i.e., j is 0); Y² is —Leu-Gly-Val-Leu-Gly-Lys-Leu-homocysteine—NH$_2$ (i.e., —LGVLGKLHc—NH$_2$ and k is 8); $R^H$ is —CH$_2$X, wherein X is Cl, Br, or I; and $R^B$ is —H (SEQ ID NO:41). The chirality of the carbon with substituents $R^H$ and $R^B$ is in the l-form.

Y¹ is H— (i.e., j is 0); Y² is —Leu-Gly-Val-Leu-Gly-Lys-Leu-homocysteine—NH$_2$ (i.e., —LGVLGKLHc—NH$_2$ and k is 8); $R^H$ is —CH$_2$CH$_2$X, wherein X is Cl, Br, or I; and $R^B$ is —H (SEQ ID NO:42). The chirality of the carbon with substituents $R^H$ and $R^B$ is in the l-form.

Examples of preferred halogenated polypeptides of the present invention include those represented by formula (IV) above which effectively comprise haloanalogs of the polypeptide SLGVLAKLC (denoted X-AG3 (SEQ ID NO:43)) and wherein:

Y¹ is H— (i.e., j is 0); Y² is —Leu-N$^α$MeGly-d-Val-d-Leu-Ala-Lys-Leu-Cys—NH$_2$ (i.e., —L(N$^α$Me—G)(d-V)(d-L)AKLC and k is 8); $R^H$ is —CH$_2$X, wherein X is Cl, Br, or I; and $R^B$ is —H (SEQ ID NO:44). The chirality of the carbon with substituents $R^H$ and $R^B$ is in the l-form.

Y¹ is H— (i.e., j is 0); Y² is —Leu-N$^α$MeGly-d-Val-d-Leu-Ala-Lys-Leu-Cys—NH$_2$ (i.e., —L(N$^α$Me—G)(d-V)(d-L)AKLC and k is 8); $R^H$ is —CH$_2$CH$_2$X, wherein X is Cl, Br, or I; and $R^B$ is —H (SEQ ID NO:45). The chirality of the carbon with substituents $R^H$ and $R^B$ is in the l-form.

Y¹ is H— (i.e., j is 0); Y² is —Leu-N$^α$MeGly-d-Val-d-Leu-Ala-Lys-Leu-homocysteine—NH$_2$ (i.e., —L(N$^α$Me—G)(d-V)(d-L)AKLHc and k is 8); $R^H$ is —CH$_2$X, wherein X is Cl, Br, or I; and $R^B$ is —H (SEQ ID NO:46). The chirality of the carbon with substituents $R^H$ and $R^B$ is in the l-form.

Y¹ is H— (i.e., j is 0); Y² is —Leu-N$^α$MeGly-d-Val-d-Leu-Ala-Lys-Leu-homocysteine—NH$_2$ (i.e., —L(N$^α$Me—G)(d-V)(d-L)AKLHc and k is 8); $R^H$ is —CH$_2$CH$_2$X, wherein X is Cl, Br, or I; and $R^B$ is —H (SEQ ID NO:47). The chirality of the carbon with substituents $R^H$ and $R^B$ is in the l-form.

Examples of preferred halogenated polypeptides of the present invention include those represented by formula (IV) above which effectively comprise haloanalogs of the polypeptide GPSLILAPDRC (denoted X-CB10) and wherein:

Y¹ is Gly-Pro- (i.e., GP— and j is 2); Y² is —Leu-Ile-Leu-Ala-Pro-Asp-Arg-Cys—NH$_2$ (i.e., —LILAPDRC—NH$_2$ and k is 8); $R^H$ is —CH$_2$X, wherein X is Cl, Br, or I; and $R^B$ is —H (SEQ ID NO:49). The chirality of the carbon with substituents $R^H$ and $R^B$ is in the l-form.

Y¹ is Gly-Pro- (i.e., GP— and j is 2); Y² is —Leu-Gly-Val-Leu-Gly-Lys-Leu-Cys—NH$_2$ (i.e., —LILAPDRC—NH$_2$ and k is 8); $R^H$ is —CH$_2$CH$_2$X, wherein X is Cl, Br, or I; and $R^B$ is —H (SEQ ID NO:50). The chirality of the carbon with substituents $R^H$ and $R^B$ is in the l-form.

Y¹ is Gly-Pro- (i.e., GP— and j is 2); Y² is —Leu-Gly-Val-Leu-Gly-Lys-Leu-homocysteine—NH$_2$ (i.e., —LILAPDRHc—NH$_2$ and k is 8); $R^H$ is —CH$_2$X, wherein X is Cl, Br, or I; and $R^B$ is —H (SEQ ID NO:51). The chirality of the carbon with substituents $R^H$ and $R^B$ is in the l-form.

$Y^1$ is Gly-Pro- (i.e., GP— and j is 2); $Y^2$ is —Leu-Gly-Val-Leu-Gly-Lys-Leu-homocysteine—$NH_2$ (i.e., —LILAPDRHc—$NH_2$ and k is 8); $R^H$ is —$CH_2CH_2X$, wherein X is Cl, Br, or I; and $R^B$ is —H (SEQ ID NO:52). The chirality of the carbon with substituents $R^H$ and $R^B$ is in the l-form.

C. Preparation of Halogenated Polypeptides

The present invention also pertains methods for the preparation of halogenated polypeptides having at least one haloalanine-like amino acid, said haloalanine-like amino acid having a halo group (i.e., —X wherein X is Cl, Br, or I). More particularly, such halogenated polypeptides may be prepared from reactant polypeptides, said reactant polypeptides having at least one serine-like amino acid, said serine-like amino acid having an hydroxyl group (i.e., —OH). More specifically, the halogenated polypeptides of the present invention may be prepared by converting the hydroxyl group of a serine-like amino acid to a halo group with the aid of a phosphorus-based halogenation reagent, thus yielding a haloalanine-like amino acid (i.e., "halo-conversion").

The term "serine-like amino acid" is used herein to refer to alpha amino acids which may be represented by the formula $HNR^N$—$CR^OR^B$—COOH (as the free amino acid) or as —$NR^N$—$CR^OR^B$—C(=O)— (when part of a polypeptide chain), where $R^N$, $R^O$ and $R^B$ are substituents. The substituents $R^N$ and $R^B$ are as defined above for $R^{N1}/R^{N2}$ and $R^1/R^2$, respectively, and are independently —H or an organic substituent. Two or more of the substituents $R^N$, $R^O$ and $R^B$ may together form a single multivalent substituent. The substituent $R^O$ (or a single multivalent substituent incorporating $R^O$ and one or more of $R^N$ and $R^B$) is a hydroxyl-containing group. The term "hydroxyl-containing group" is used herein to refer to organic moieties which comprise an hydroxyl group (i.e., —OH). The alpha carbon of the serine-like amino acid may have chirality R or S.

In some preferred embodiments, $R^O$ is an hydroxyl-containing alkyl group. The term "hydroxyl-containing alkyl group" is used herein to refer to organic moieties which comprise an hydroxyl group (i.e., —OH) and an alkyl moiety. The alkyl moiety preferably comprises from 1 to 10 carbon atoms, more preferably 1 to 5 carbon atoms, still more preferably 1 to 3 carbon atoms, most preferably 1 to 2 carbon atoms. The alkyl moiety may be linear, cyclic, or branched, but is preferably linear. Examples of preferred hydroxyl-containing alkyl groups include those of the general formula —$(CH_2)_z$OH where z is a natural number from 1 to 10, more preferably 1 to 5, still more preferably 1 to 3, most preferably 1 to 2. Examples of more preferred hydroxyl-containing alkyl groups include —$CH_2OH$ (i.e., as in the case of serine) and —$CH_2CH_2OH$ (i.e., as in the case of homoserine). Another example of a preferred hydroxyl-containing alkyl group is —$CH(CH_3)OH$ (i.e., as in the case of threonine).

The hydroxyl group of the serine-like amino acid, which is to be converted to a halo group, may be in a suitably protected form, or in a free form (i.e., as —OH). Preferably, the hydroxyl group is in a protected form, as this may eliminate a deprotection step which may otherwise be necessary, for example, when the reactant polypeptide is obtained in a protected form. Thus, in preferred embodiments, the hydroxyl group of the serine-like amino acid is protected, more preferably with a TBDMS group (e.g., —$Si(CH_3)_2(C(CH_3)_3)$; as —OTBDMS). If it is desired to perform halo-conversion with the hydroxyl group of the serine-like amino acid in a free form (i.e., as —OH), the TBDMS group can be selectively removed with 3 equivalents of TBAF (i.e., tetrabutylammonium fluoride) in THF (i.e., tetrahydrofuran) in the presence of protecting groups other than base labile groups such as Fmoc. Similarly, a trityl-protected hydroxyl group (i.e., —OTr) may be conveniently deprotected to yield the free hydroxyl group (i.e., —OH) with 1% TFA (i.e., trifluoroacetic acid) in 1:1 DCM/MeOH (i.e., dichloromethane, methanol).

Halo-conversion is effected by reaction of the reactant polypeptide with a phosphorus-based halogenation reagent. As used herein, the term "phosphorus-based halogenation reagent" relates to trialkylphosphine-based or trialkylphosphite-based halogenation reagents. Examples of preferred halogenation reagents include those comprising triphenylphosphine dihalide (i.e., $(C_6H_5)_3PX_2$, wherein X is Cl, Br, or I; dihalotriphenylphosphorane); triphenylphosphite dihalide (i.e., $(C_6H_5O)_3PX_2$, wherein X is Cl, Br, or I); or a mixture of triphenylphosphine (i.e., $(C_6H_5)_3P$) or triphenylphosphite (i.e., $(C_6H_5O)_3P$) with halohydrocarbon compounds. Examples of halohydrocarbon compounds include carbon tetrahalide (i.e., $CX_4$, wherein X is Cl, Br, or I), hexahaloacetone (i.e., $CX_3C(=O)CX_3$, wherein X is independently Cl, Br, or I), and hexahaloethane (i.e., $C_2X_6$, wherein X is independently Cl, Br, or I). A preferred halogenation reagent comprises triphenylphosphine dichloride (i.e., $(C_6H_5)_3PCl_2$). Another preferred halogenation reagent comprises triphenylphosphine dibromide (i.e., $(C_6H_5)_3PBr_2$). Yet another preferred halogenation reagent comprises a mixture of triphenylphosphine (i.e., $(C_6H_5)_3P$) and carbon tetrachloride (i.e., $CCl_4$).

Halo-conversion may be performed using a dissolved reactant polypeptide (i.e., in solution) or using a supported reactant polypeptide (e.g., attached to a support material). For example, standard solid-phase polypeptide synthesis methods may be used to obtain a desired polypeptide which is attached to a solid support. Halo-conversion may then be performed using the supported polypeptide as the reactant polypeptide, or alternatively, the polypeptide may be cleaved from the support and the conversion reaction may then be performed using the dissolved polypeptide as the reactant polypeptide.

In a preferred embodiment, halo-conversion is performed using a supported polypeptide as the reactant polypeptide. A wide variety of solid supports are known in the art, including those in the form of resins, pins, or silicone chips. Preferably, the support is in the form of a resin. Examples of preferred resins include derivatized polystyrene resins, such as, WANG™ resin, MERRIFIELD™ resin, 4-methyl benzhydrylamine (i.e., MBHA) resin, RINK™ amide resin, RINK™ Amide MBHA resin, SIEBER™ resin, NOVASYN® TGR resin, and NOVASYN® TGA resin.

As discussed above, the hydroxyl group of the serine-like amino acid, which is to be converted to a halo group, may be in a suitably protected form (e.g., as —OTBDMS), or in a free form (i.e., as —OH). In embodiments where the reactant polypeptide comprises serine, homoserine, threonine, or other serine-like amino acids which are not to be converted to halo groups (i.e., not the subject of halo-conversion), the hydroxyl groups of these amino acids are suitably protected prior to halo-conversion, for example, with a tBu group (i.e., —$C(CH_3)_3$; as —$OC(CH_3)_3$).

Preferably, the thiol group (i.e., —SH) of any cysteine-like amino acids of the reactant polypeptide are suitably protected prior to halo-conversion. In preferred embodiments, such thiol groups are protected with a Tr group (i.e., —$C(C_6H_5)_3$; as —STr), or more preferably, with a tBuS group (i.e., —$SC(CH_3)_3$; as —$SSC(CH_3)_3$).

Preferably, halo-conversion is performed using a reactant polypeptide wherein the side-chain functional groups are suitably protected. For example, in embodiments where the polypeptide comprises arginine, the guanidino group of arginine is protected, for example, with a Pmc, Mts, or Mtr group. In embodiments where the polypeptide comprises asparagine and glutamine, the carboxamide groups of asparagine and glutamine are protected, for example, with a trityl (i.e., Tr) group. In embodiments where the polypeptide comprises aspartic and glutamic acid, the side chain carboxyl groups of aspartic and glutamic acid are protected, for example, with a tert-butyl (i.e., t-Bu) or cyclohexyl (i.e., cHx) group. In embodiments where the polypeptide comprises histidine, the imidazole group of histidine is protected, for example, with a trityl group. In embodiments where the polypeptide comprises lysine, the epsilon-amino group of lysine is protected, for example, with a Boc, CBZ or 2-Cl—CBZ group. In embodiments where the polypeptide comprises tryptophan, the indole nitrogen of tryptophan is protected, for example, with a trityl group. In embodiments where the polypeptide comprises tyrosine, the hydroxyl group of tyrosine is protected, for example, with a trityl group.

Halo-conversion may be performed using a reactant polypeptide where the terminal alpha-amino group is free (i.e., —$NH_2$ or —$NR^NH$) or suitably protected. In preferred embodiments, the terminal alpha-amino group is protected, for example, with a Fmoc, Boc, or CBZ group (e.g., as —NHFmoc, —NHBoc, —NHCBZ, respectively).

Preferably, halo-conversion is carried out using a molar excess of the phosphorus-based halogenation reagent. The molar excess may be conveniently calculated from the quantity of reactant polypeptide and the quantity of phosphorus-based halogenation reagent. For embodiments where the reactant polypeptide is a supported polypeptide, the quantity of reactant polypeptide is determined from the substitution of the resin (i.e., how much polypeptide is theoretically attached to the resin). In preferred embodiments which employ triphenylphosphine dihalide as the phosphorus-based halogenation reagent, halo-conversion is more preferably carried out using a three- to six-times molar excess of triphenylphosphine dihalide, or a concentration of about 100 mg/mL of triphenylphosphine dihalide reagent in a suitable solvent system.

Halo-conversion is carried out in a suitable solvent system, preferably at about room temperature. Suitable solvents are those which do not cause any undesired side reactions. For those embodiments which employ a resin-supported reactant polypeptide, suitable solvents also preferably give good solvation of the resin. Examples of suitable solvents include ACN (i.e., acetonitrile, $CH_3CN$) and DCM (i.e., dichloromethane, $CH_2Cl_2$).

For super acid-labile resins, such as SIEBER™ resin, halo-conversion is preferably carried out in the presence of a base, such as imidazole.

In those embodiments in which halo-conversion is performed using a supported polypeptide, it may be desirable to cleave the halogenated polypeptides from the solid support upon completion of haloconversion. The cleavage may be carried out using standard peptide synthesis methods. For example, the halogenated polypeptides may be detached from an MBHA resin using hydrogen fluoride with suitable scavangers, for example, ethylene dithiol. Under these conditions, many protecting groups, but not the Fmoc group (e.g., on the terminal alpha-amino group), may be removed from the polypeptides at the same time. Halo-polypeptides may be detached from a Wang resin using trifluoroacetic acid with suitable scavengers, for example, ethylene dithiol. Under these conditions, many protecting groups, but neither the Fmoc group (e.g., on the terminal alpha-amino group) nor the tBuS group (e.g., on the thiol group of a cysteine-like amino acid), may be removed from the polypeptides at the same time.

D. Preparation of Cyclic Polypeptides

The present invention also pertains to methods for the preparation of cyclic polypeptides, said cyclic polypeptides having at least one polypeptide loop, said loop comprising a thioether linkage. More particularly, such cyclic polypeptides may be prepared from halogenated polypeptides having (i) at least one haloalanine-like amino acid, said haloalanine-like amino acid having a halo group (i.e., —X where X is Cl, Br, or I); and (ii) at least one cysteine-like amino acid, said cysteine-like amino acid having a thiol group (i.e., —SH). Cyclic polypeptides may be prepared from such halogenated polypeptides by intramolecular alkylation of the thiol group of a cysteine-like amino acid by the halo group of a haloalanine-like amino acid under suitable basic conditions to form a thioether linkage (i.e., "cyclization").

The term "cysteine-like amino acid" is used herein to refer to alpha-amino acids which may be represented by the formula $HNR^N$—$CR^SR^B$—COOH (as the free amino acid) or as —NH—$CR^SR^B$—C(=O)— (when part of a polypeptide chain), wherein $R^N$, $R^S$ and $R^B$ are substituents. $R^B$ is —H or an organic substituent, for example, an alkyl group having 1 to 6 carbon atoms, but more preferably —$CH_3$ or —H; and $R^N$ is —H or an organic substituent, for example, an alkyl group having 1 to 6 carbon atoms, but more preferably —H. Two or more of the substituents $R^N$, $R^S$ and $R^B$ may together form a single multivalent substituent. The substituent $R^S$ (or a single multivalent substituent incorporating $R^S$ and one or more of $R^N$ and $R^B$) is a thiol-containing group. The term "thiol-containing group" is used herein to refer to organic moieties which comprise a thiol group (i.e., —SH). The alpha carbon of the cysteine-like amino acid may have chirality R or S.

In some preferred embodiments, $R^S$ is a thiol-containing alkyl group. The term "thiol-containing alkyl group" is used herein to refer to organic moieties which comprise a thiol group (i.e., —SH) and an alkyl moiety. The alkyl moiety preferably comprises from 1 to 10 carbon atoms, more preferably 1 to 5 carbon atoms, still more preferably 1 to 3 carbon atoms, most preferably 1 to 2 carbon atoms. The alkyl moiety may be linear, cyclic, or branched, but is preferably linear. Examples of preferred thiol-containing alkyl groups include those of the general formula —$(CH_2)_z$SH where z is a natural number from 1 to 10, more preferably 1 to 5, still more preferably 1 to 3, most preferably 1 to 2. Examples of more preferred thiol-containing alkyl groups include —$CH_2SH$ (i.e., as in the case of cysteine) and —$CH_2CH_2SH$ (i.e., as in the case of homocysteine). Other examples of preferred thiol-containing alkyl groups include —$CH(CH_3)SH$ and —$C(CH_3)_2SH$ (i.e., as in the case of penicillamine). Still other examples of cysteine-like amino acids include 4-mercaptoproline and 2-mercaptohistidine.

Different thioether linkages may be obtained by employing different halogenated polypeptides. For example, when the haloalanine-like amino acid is obtained by halo-conversion of serine ($R^H$ is —$CH_2$—X), and the cysteine-like amino acid is cysteine ($R^S$ is —$CH_2$—SH), the thioether linkage —$CH_2$—S—$CH_2$— (i.e., MMTE; methylene-methylene-thioether) is obtained. Similarly, when the haloalanine-like amino acid is obtained by halo-conversion of homoserine ($R^H$ is —$CH_2CH_2$—X), and the cysteine-like amino acid is homocysteine ($R^S$ is —$CH_2CH_2$—SH), the thioether linkage —CH$_2$CH$_2$—S—CH$_2$CH$_2$— (i.e., EETE, ethylene-ethylene-thioether) is obtained. When the haloalanine-like amino acid is obtained by halo-conversion of homoserine (R$^H$ is —CH$_2$CH$_2$—X), and the cysteine-like amino acid is cysteine (R$^S$ is —CH$_2$—SH), the thioether linkage —CH$_2$CH$_2$—S—CH$_2$— (i.e., EMTE, ethylene-methylene-thioether) or —CH$_2$—S—CH$_2$CH$_2$— (i.e., METE, methylene-ethylene-thioether) is obtained, according to the relative positions of the two amino acids. Similarly, when the haloalanine-like amino acid is obtained by halo-conversion of serine (R$^H$ is —CH$_2$X), and the cysteine-like amino acid is homocysteine (R$^S$ is —CH$_2$CH$_2$—SH), the thioether linkage —CH$_2$—S—CH$_2$CH$_2$— (i.e., METE, methylene-ethylene-thioether) or —CH$_2$CH$_2$—S—CH$_2$— (i.e., EMTE, ethylene-methylene-thioether) is obtained, according to the relative positions of the two amino acids.

Cyclization is effected by intramolecular alkylation of a thiol group by a halo group of a halogenated polypeptide having at least one haloalanine-like amino acid and at least one cysteine-like amino acid, in a suitable basic medium. For example, cyclization can be achieved by reaction of the halogenated polypeptide with sodium carbonate (i.e., Na$_2$CO$_3$) in a suitable solvent.

Cyclization may be performed using a dissolved halogenated polypeptide (i.e., in solution) or using a supported halogenated polypeptide (e.g., attached to a support material). For example, the halogenated polypeptide may be prepared, as describe above, by derivatizing a reactant polypeptide (i.e., halo-conversion) while attached to a solid support. Cyclization may then be performed using the supported halogenated polypeptide, or alternatively, the halogenated polypeptide may be cleaved from the support and cyclization performed using the dissolved halogenated polypeptide.

In those embodiments where cyclization is performed using a supported halogenated polypeptide wherein the thiol group of the cysteine-like amino acid is in a protected form, it may be deprotected under suitable conditions. For example, a thiol group protected with a tBuS group may be deprotected with tributyl phosphine (i.e., P(C$_4$H$_9$)$_3$). A thiol group protected with a trityl group may be conveniently deprotected with 1% TFA (i.e., trifluoroacetic acid) in DCM (i.e., dichloromethane) plus trimethylsilane (i.e., SiH(CH$_3$)$_3$). Under these conditions, many other types of protecting groups remain intact. The cyclization reaction can be effectively performed using a solvent mixture (1:1 v/v) of acetonitrile (i.e., CH$_3$CN) and water (i.e., H$_2$O) with about 10–20 mg/mL of sodium carbonate (i.e., Na$_2$CO$_3$). Examples of preferred supports for cyclization of a supported halogenated polypeptide include poly(ethylene glycerol) resins, such as, NOVASYN® TGA and NOVASYN® TGR resins.

In those embodiments where the cyclization step is performed using a dissolved halo-polypeptide (i.e., in solution), the thiol group of the cysteine-like amino acid may be deprotected (e.g., under the cleavage conditions). However, if necessary, it may be deprotected under suitable conditions. For example, a thiol group protected with a tBuS group may be deprotected with tributyl phosphine (i.e., P(C$_4$H$_9$)$_3$). To avoid intermolecular side reactions, high dilution of the halo-polypeptide in solution is necessary during cyclization. In solution, the cyclization reaction can be effectively performed using a diluted polypeptide solution (e.g., about 1 mg/mL) in a solvent mixture (1:1 v/v) of acetonitrile (i.e., CH$_3$CN) and water (i.e., H$_2$O) with about 1 mg/mL of sodium carbonate (i.e., Na$_2$CO$_3$).

Thus, the cyclic polypeptides of the present invention may be prepared from reactant polypeptides having at least one serine-like amino acid and at least one cysteine-like amino acid by halo-conversion, first, and cyclization, second, as described above. More specifically, the cyclic polypeptides of the present invention may be prepared from reactant polypeptides having (i) at least one serine-like amino acid, said serine-like amino acid having a hydroxyl group (i.e., —OH); and (ii) at least one cysteine-like amino acid, said cysteine-like amino acid having a thiol group (i.e., —SH) by (a) converting the hydroxyl group of said serine-like amino acid to a halo group (i.e., —X where X is Cl, Br, or I) with the aid of a phosphorus-based halogenation reagent, thus yielding a haloalanine-like amino acid (i.e., "halo-conversion"); followed by (b) intramolecular alkylation of the thiol group of a cysteine-like amino acid by the halo group of a haloalanine-like amino acid under suitable basic conditions to form a thioether linkage (i.e., "cyclization"). The halo-conversion and cyclization steps are described in detail above.

The halo-conversion step may be performed using a reactant polypeptide which is dissolved (i.e., in solution) or supported (e.g., attached to a support material), as described above. Similarly, the cyclization step may be performed using a halogenated polypeptide which is dissolved (i.e., in solution) or supported (e.g., attached to a support material), as described above. In those embodiments in which halo-conversion employs a supported polypeptide and in which the cyclization step is to be performed in solution, the halogenated polypeptides may be cleaved from the solid support upon completion of the halo-conversion using standard peptide synthesis methods. Preferably, the halo-conversion step is performed using a reactant polypeptide which is supported.

Many other modifications and variations of the invention as hereinbefore set forth can be made without departing from the spirit and scope thereof and therefore only such limitations should be imposed as are indicated by the appended claims.

E. Examples

Several of the halogenated polypeptides and cyclic polypeptides of the present invention, and methods for preparing them, are described in the following examples, which are offered by way of illustration and not by way of limitation.

For convenience, a number of chemical compounds are interchangeably referred to herein by their chemical name, chemical formula, and/or a suitable acronym. These include DCM (i.e., dichloromethane, CH$_2$Cl$_2$); DMF (i.e., dimethylformamide, (CH$_3$)$_2$NCHO); MeOH, (i.e., methanol, CH$_3$OH); EtOH (i.e., ethanol, CH$_3$CH$_2$OH); nPrOH (i.e., n-propanol, CH$_3$CH$_2$CH$_2$OH); TFA (i.e., trifluoroacetic acid, CF$_3$COOH); DMS (i.e., dimethyl sulfide, CH$_3$SCH$_3$); ACN (i.e., acetonitrile, CH$_3$CN); THF (i.e., tetrahydrofuran, C$_4$H$_8$O); water (i.e., H$_2$O); hydrogen fluoride (i.e., HF); anisole (i.e., C$_6$H$_5$OCH$_3$); para-thiocresol (i.e., CH$_3$—C$_6$H$_4$—SH); diethyl ether (i.e., C$_2$H$_5$OC$_2$H$_5$); sodium carbonate (i.e., Na$_2$CO$_3$); ethylene dithiol (i.e., HSCH$_2$CH$_2$SH); and tributylphosphine (i.e., P(C$_4$H$_9$)$_3$).

The general analytical methods and characterization techniques used in the present disclosure are identified below. $^1$H NMR spectra were recorded on a Bruker AC300 spectrometer at 300 MHz. Chemical shifts were recorded in parts per million (δ) relative to TMS (i.e., tetramethylsilane, δ=0.0 ppm). Analytical HPLC analyses were performed on a Hewlett Packard liquid chromatography HP 1090 instrument fitted with a Vydac C18 column (4.6×250 mm, 5 mm particle size). Preparative HPLC was performed on Dynamax SD 200 system with a Vydac C18 column (22×250 mm, 10 mm particle size). The purity of peptide products was analyzed using two HPLC solvent systems: a trifluoroacetic acid (TFA) system or a triethylamine phosphate (TEAP) system. In the TFA system, a gradient of 5–50% B over 20 min was used, where A was 0.1% (v/v) TFA/H$_2$O and B was 0.1% (v/v) TFA/ACN. In the TEAP system, a gradient of 5–60% B over 20 min was used, where A was 9:1 TEAP/ACN (v/v) and B was 4:6 TEAP/ACN (v/v). TEAP buffer was prepared by adding 11 mL of concentrated phosphoric acid (i.e., H$_3$PO$_4$, 85% w/v) to 900 mL of H$_2$O and adjusting the pH to 2.3 with triethylamine (i.e., N(C$_2$H$_5$)$_3$, about 10 mL) and then made up to a volume of 1000 mL with more H$_2$O.

All common amino acid derivatives were purchased from NovaBiochem or Advanced ChemTech. N$^\alpha$-(9-Fluorenylmethyoxycarbonyl)-O-t-butyldimethylsilyl-l-serine and N$^\alpha$-(9-fluorenylmethyoxycarbonyl)-O-t-butyldimethylsilyl-d-serine were obtained from Bachem Bioscience Inc. N$^\alpha$-(9-Fluorenylmethyoxycarbonyl)-O-t-butyldimethylsilyl-l-homoserine was prepared as described by Fisher (*Tetrahedron Lett.* (1992) 49:7605–7608). N$^\alpha$-(9-Fluorenylmethyoxycarbonyl)-S-t-butylthio-l-homocysteine was prepared according to the procedure of Wunsch et al. (*Hoppe-Seyler's Z. Physiol. Chem.* (1982), 363:1461–1464). Triphenylphosphine dichloride and triphenylphosphine dibromide were purchased from Aldrich Chemical Company; their purities were monitored by $^{31}$P NMR before use (Appel et al., *Chem. Ber.* (1976) 109:58–70). More preferably, triphenylphosphine dichloride was prepared fresh according to the procedure of Appel and Scholer (*Chem. Ber.* (1977) 110:2382–2384).

The polypeptides used in the preparation of the cyclic polypeptides of the present invention were prepared using standard solid phase synthesis methods. The experimental details of two specific methods, denotes Method A and Method B, which were used in the examples are described below.

In Method A, the polypeptides were synthesized manually using standard Fmoc solid phase chemistry (Stewart and Young, *Solid Phase Peptide Synthesis,* 2nd., Pierce Chemical Co,: Rockford, Ill., (1984); p 82; Fields and Noble, *Int. J. Pept. Protein Res.* (1990) 35:161–214). During each cycle, the Fmoc group was removed by treatment with 20% piperidine (i.e., NHC$_5$H$_{11}$) in DMF for 5 and 10 min. The peptide resin was then washed successively with DMF (twice), MeOH (twice), DMF (twice), and MeOH (twice). The amino acid was coupled to the resin using 3 equivalents of the Fmoc-protected amino acid, 3 equivalents of DIC (i.e., N,N'-diisopropylcarbodiimide), and 3 equivalents of HOBt (i.e., N-hydroxybenzotriazole) in DMF at 55° C. The coupling reaction was monitored by addition of indicator bromophenol blue (~5 mL of a 0.05M solution in DMF). Coupling continued until the disappearance of the blue color and formation of a yellow color. A typical single coupling required from 15 to 120 minutes, depending on the polypeptide sequence and the amino acid residue to be coupled. The polypeptide resin was washed successively with DMF (twice), MeOH (twice), DMF (twice), and MeOH (twice). The completion of the coupling was confirmed by a ninhydrin test (Kaiser et al., *Anal. Biochem.* (1970) 34:595–598) and double coupling was performed if required.

In Method B, the polypeptides were synthesized using solid phase chemistry in an automated fashion on an Advanced ChemTech 357 MPS automated synthesizer using Fmoc chemistry (Fields and Noble, *Int. J. Pept. Protein Res.* (1990) 35:161–214). A typical cycle for the coupling of an individual amino acid was as follows: (1) deprotection of the amino acid on the resin with 30% piperidine/DMF for 5 and 10 min; (2) washing successively with DMF, MeOH, DMF, and MeOH; (3) double couplings of the amino acid, each with 6 equivalents of the Fmoc-protected amino acid, 6 equivalents of DIC, and 6 equivalents of HOBt in DMF for 60 min at room temperature; (4) washing successively with DMF, MeOH, DMF, and MeOH. The resin was then transferred to the cleavage vessel and washed with DCM and dried under vacuum.

EXAMPLE 1

Figure 2:
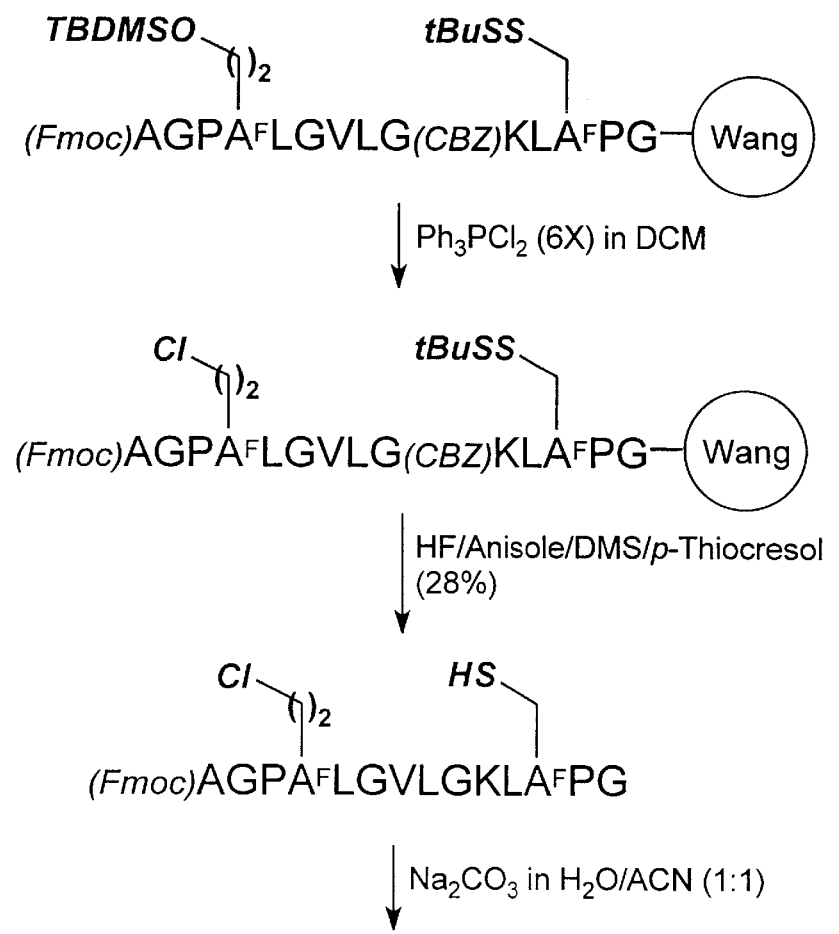
FIG. 2 is a reaction scheme illustrating the synthesis of $N^\alpha$-Fmoc-3G3-EMTE (SEQ ID NO:4) and 3G3-EMTE cyclic peptides as described in Example 1.
Figure 2:
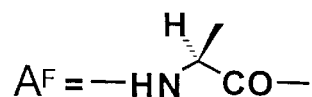

Cyclization of (Fmoc)AGPHsLGVLGKLCPG (SEQ ID NO:53) to form 3G3-EMTE and N$^\alpha$-Fmoc-3G3-EMTE A reaction scheme illustrating the synthesis in this example is shown in FIG. 2. The resin-bound fully protected peptide (Fmoc)AGP(TBDMS)HsLGVLG(CBZ)KL(tBuS)CPG(SEQ ID NO:53)-resin was prepared using Method A on (Fmoc)-Gly-Wang resin (NovaBiochem, 0.50 g, 0.67 mmol/g). Side chain functional groups were protected as follows: Cys (tBuS); Lys (CBZ); Hs (TBDMS). After completion of all couplings, the peptide resin was washed with DCM (twice) and subsequently dried in vacuo.

The TBDMS protected hydroxyl group (i.e., —OTBDMS) of homoserine residue, Hs, was converted to chloro group (i.e., —Cl) by treatment with 6 equivalents of triphenylphosphine dichloride (i.e., (C$_6$H$_5$)$_3$PCl$_2$) in DCM overnight at room temperature. The polypeptide resin was washed successively with DMF (twice), MeOH (twice), DMF (twice), and MeOH (twice) and then dried in vacuo. The dried polypeptide resin was then treated with a 10:1:1:0.2 (v/v) mixture of HF, anisole, DMS, and para-thiocresol for one hour at 0° C. After removal of HF in vacuo, the residue was washed three times with diethyl ether to remove scavengers and extracted three times with 0.1% TFA in 1:1 (v/v) H$_2$O/ACN. The combined filtrates were lyophilized and the crude polypeptide was purified by preparative HPLC eluted at 10 mL/min with a linear gradient from 40 to 70% B over 40 minutes where A was 0.1% (v/v) TFA in H$_2$O and B was 0.08% (v/v) TFA in ACN. The chloro-polypeptide was obtained as a white powder after further lyophilization (153.5 mg, 28% yield; Analytical RP-HPLC: TFA system with a gradient of 20–80% B over 20 min: $t_R$ 15.60 min; purity, 97.2%; MS (ESI): m/e (M+1) Calcd. for C$_{72}$H$_{109}$N$_{15}$O$_{17}$SCl: 1523, obsd.: 1523).

The chloro-polypeptide (48.0 mg) was dissolved in 50 mL of a sodium carbonate (i.e., Na$_2$CO$_3$, 1 mg/mL, pH ~10.5) solution in ACN/water (1:1) at room temperature, under argon, for 36 hours with stirring. The cyclization reaction was monitored by analytical HPLC. After the completion of cyclization, indicated by the disappearance of the starting material, the solution was neutralized with TFA and lyophilized. The crude cyclic polypeptide material was purified using preparative HPLC eluted at 10 mL/min with a linear gradient from 10 to 70% B over 40 minutes where A was 0.1% (v/v) TFA in H$_2$O and B was 0.08% (v/v) TFA in ACN. Two cyclic polypeptides, N$^\alpha$-Fmoc-3G3-EMTE and 3G3-EMTE, were obtained (N$^\alpha$-Fmoc-3G3-EMTE: 9.0 mg, 19% yield; Analytical RP-HPLC: TFA system with a gradient of 20–80% B over 20 min: $t_R$ 15.58 min; purity, 97.0%; TEAP system: $t_R$ 17.13 min; purity, 94.0%; MS (ESI): m/e (M+Cs$^+$) Calcd. for C$_{72}$H$_{107}$N$_{15}$O$_{17}$SCs: 1618.6744, obsd.: 1618.6763; 3G3-EMTE: 13.3 mg, 33% yield; Analytical RP-HPLC: TFA system: $t_R$ 15.16 min; purity, 100%; TEAP system: $t_R$ 12.85 min; purity, 100%; HRMS (ESI): m/e (M+Cs$^+$) Calcd. for C$_{57}$H$_{97}$N$_{15}$O$_{15}$SCs: 1396.6064, obsd.: 1396.6083).

EXAMPLE 2

Cyclization of AGPHsLGVLGKLCPG (SEQ ID NO:53) to form 3G3-EMTE

Figure 3:
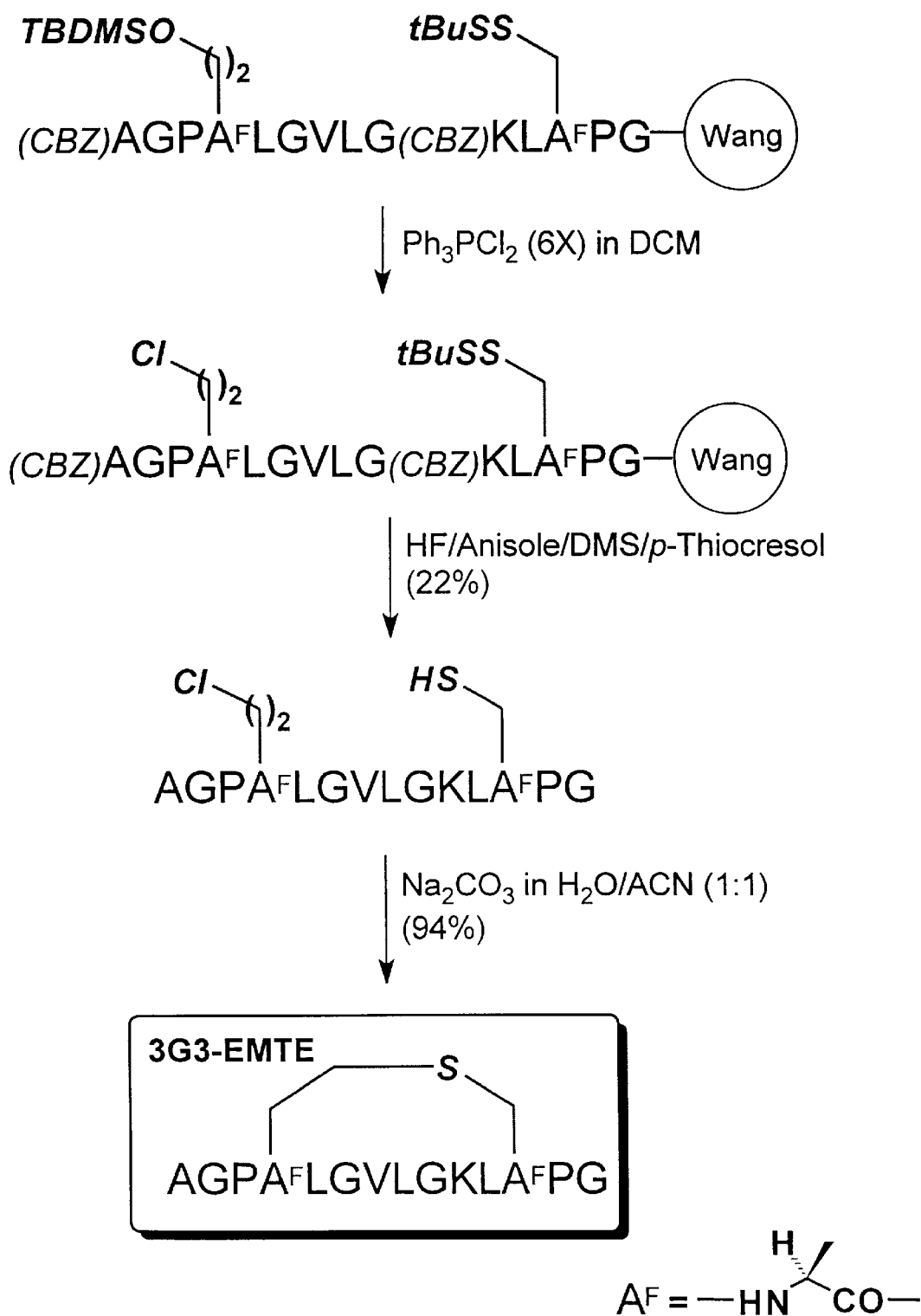
FIG. 3 is a reaction scheme illustrating the synthesis of the 3G3-EMTE (SEQ ID NO:4) cyclic peptide as described in Example 2.

A reaction scheme illustrating the synthesis in this example is shown in FIG. 3. The resin-bound fully protected peptide (CBZ)AGP(TBDMS)HsLGVLG(CBZ)KL(tBuS) CPG-resin was prepared by Method A on (Fmoc)-Gly-Wang resin (NovaBiochem, 0.50 g, 0.60 mmol/g). Side chain functional groups were protected as follows: Cys (tBuS); Lys (CBZ); Hs (TBDMS). The alpha-amino group of the polypeptide was protected with a CBZ group. After completion of all couplings, the peptide resin was washed with DCM (twice) and dried in vacuo.

The TBDMS protected hydroxyl group (i.e., —OTBDMS) of homoserine residue, Hs, was converted to chloro group (i.e., —Cl) by treatment with 6 equivalents of triphenylphosphine dichloride (i.e., $(C_6H_5)_3PCl_2$) in DCM overnight at room temperature. The polypeptide resin was washed successively with DMF (twice), MeOH (twice), DMF (twice), and MeOH (twice) and then dried in vacuo. The dried polypeptide resin was then treated with a 10:1:1:0.2 (v/v) mixture of HF, anisole, DMS, and para-thiocresol for one hour at 0° C. After removal of HF in vacuo, the residue was washed three times with diethyl ether to remove scavengers and extracted three times with 0.1% TFA in 1:1 (v/v) $H_2O$/ACN. The combined filtrates were lyophilized and the crude polypeptide was purified by preparative HPLC eluted at 10 mL/min with a linear gradient from 10 to 40% B over 40 minutes where A was 0.1% (v/v) TFA in $H_2O$ and B was 0.08% (v/v) TFA in ACN. The chloro-polypeptide was obtained as a white powder after further lyophilization (100.5 mg, 22% yield; Analytical RP-HPLC: TFA system: $t_R$ 16.48 min; purity, 95.1%; TEAP system: $t_R$ 14.69 min; purity, 93.7%; MS (ESI): m/e (M+1) Calcd. for $C_{57}H_{99}N_{15}O_{15}SCl$: 1301, obsd.: 1301).

The chloro-polypeptide (18.5 mg) was dissolved in 20 mL of a sodium carbonate (i.e., $Na_2CO_3$, 1 mg/mL, pH ~10.5) solution in ACN/water (1:1) at room temperature, under argon, for 24 hours with stirring. The cyclization reaction was monitored by analytical HPLC. After the completion of cyclization, indicated by the disappearance of the starting material, the solution was neutralized with TFA and lyophilized. The crude cyclic polypeptide material was purified using preparative HPLC eluted at 10 mL/min with a linear gradient from 10 to 40% B over 40 minutes where A was 0.1% (v/v) TFA in $H_2O$ and B was 0.08% (v/v) TFA in ACN. The cyclic polypeptides was obtained as a white powder after further lyophilization (17.0 mg, 94% yield; Analytical RP-HPLC:

TFA system: $t_R$ 15.16 min; purity, 100%; TEAP system: $t_R$ 12.85 min; purity, 100%; HRMS (ESI): m/e (M+Cs$^+$) Calcd. for $C_{57}H_{97}N_{15}O_{15}SCs$: 1396.6064, obsd.: 1396.6083).

EXAMPLE 3
Cyclization of AGPSLGVLGKLCPG to form 3G3-MMTE

Figure 4:
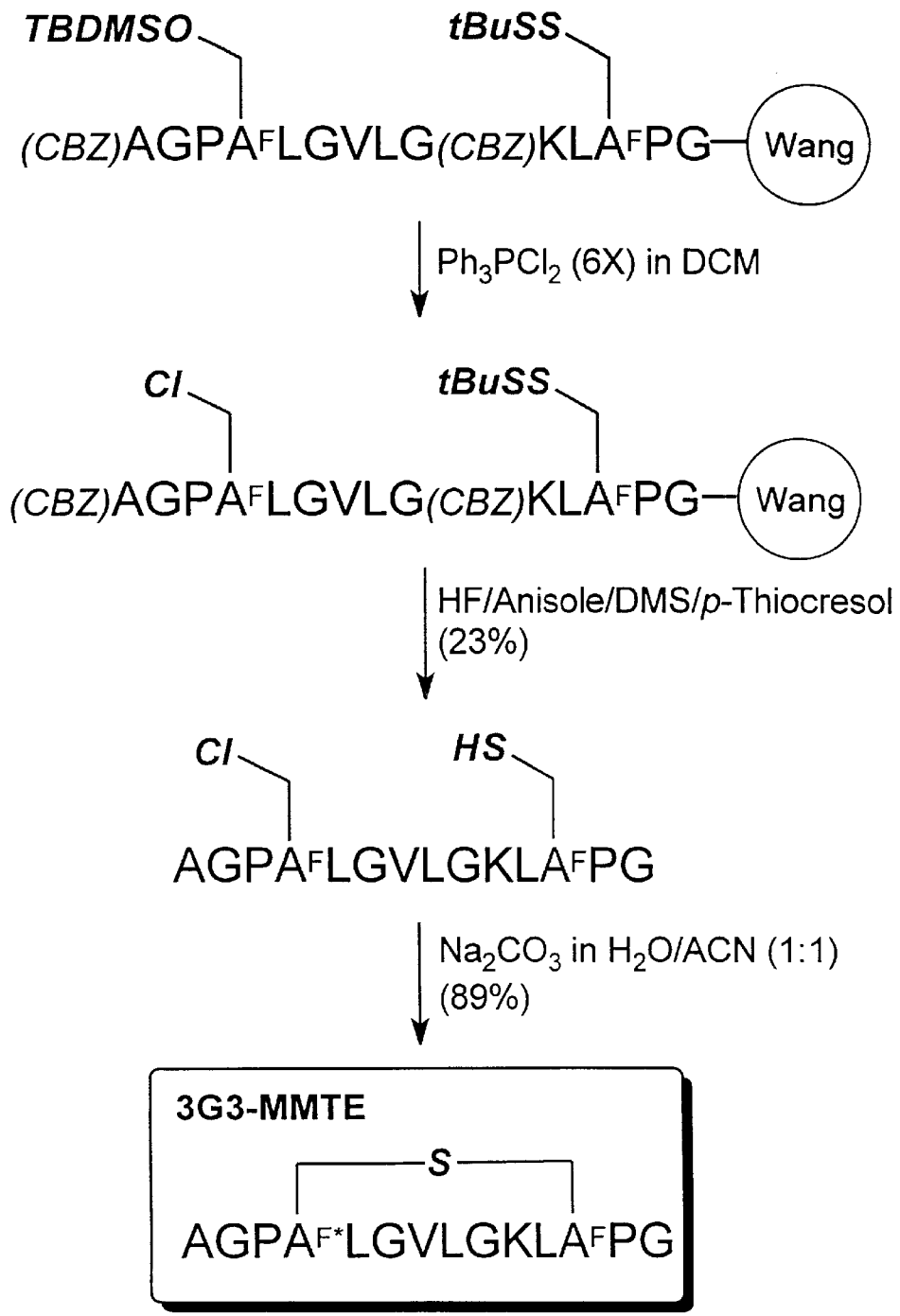
FIG. 4 is a reaction scheme illustrating the synthesis of the 3G3-MMTE (SEQ ID NO:3) cyclic peptides as described in Example 3.
Figure 4:

A reaction scheme illustrating the synthesis in this example is shown in FIG. 4. The methods for polypeptide synthesis, chlorination, and cyclization described in Example 2, above, were adapted in this example. The same protecting group scheme for the side chain functional groups and alpha-amino group was used in this example.

Using 0.50 g of (Fmoc)-Gly-Wang resin (NovaBiochem, 0.60 mmol/g) the chloro-polypeptide was obtained as a white powder after purification (105.5 mg, 23% yield; Analytical RP-HPLC: TFA system: $t_R$ 15.99 min; purity, 92.5%; TEAP system: $t_R$ 14.08 min; purity, 95.9%; MS (ESI): m/e (M+1) Calcd. for $C_{56}H_{97}N_{15}O_{15}SCl$: 1287, obsd.: 1287).

Using 50.0 mg of the chloro-polypeptide, the cyclic polypeptide was obtained as a mixture of two diastereomers (43.1 mg, 89% yield; Analytical RP-HPLC: TFA system: $t_R$ 14.78 min; purity, 100%; TEAP system: $t_R$ 11.98 min; purity, 100% with a shoulder; HRMS (ESI): m/e (M+Cs$^+$) Calcd. for $C_{56}H_{95}N_{15}O_{15}SCs$: 1382.5907, obsd.: 1382.5919).

EXAMPLE 4
Cyclization of GPHsLGVLGKLHcPG (SEQ ID NO:54) to form 2G3-EETE

The methods for polypeptide synthesis, chlorination, and cyclization described in Example 2, above, were adapted in this example. The same protecting group scheme for the side chain functional groups and alpha-amino group was used in this example.

Using 1.0 g of (Fmoc)-Gly-Wang resin (Advanced ChemTech, 0.34 mmol/g) the chloro-polypeptide was obtained as a white powder after purification (72.0 mg, 17% yield; Analytical RP-HPLC: TFA system: $t_R$ 16.89 min; purity, 100%; TEAP system: $t_R$ 14.84 min; purity, 100%; HRMS (ESI): m/e (M+1) Calcd. for $C_{55}H_{96}N_{14}O_{14}SCl$: 1243.6640, obsd.: 1243.6692).

Using 25.0 mg of the chloro-polypeptide, the cyclic polypeptide was obtained as a white powder (18.2 mg, 75% yield; Analytical RP-HPLC: TFA system: $t_R$ 15.63 min; purity, 100%; TEAP system: $t_R$ 13.81 min; purity, 100%; HRMS (ESI): m/e (M+1) Calcd. for $C_{55}H_{95}N_{14}O_{14}S$: 1207.6873, obsd.: 1207.6827).

EXAMPLE 5
Cyclization of GPHsLGVLGKLCPG (SEQ ID NO:55) to form 2G3-EMTE

Figure 5:
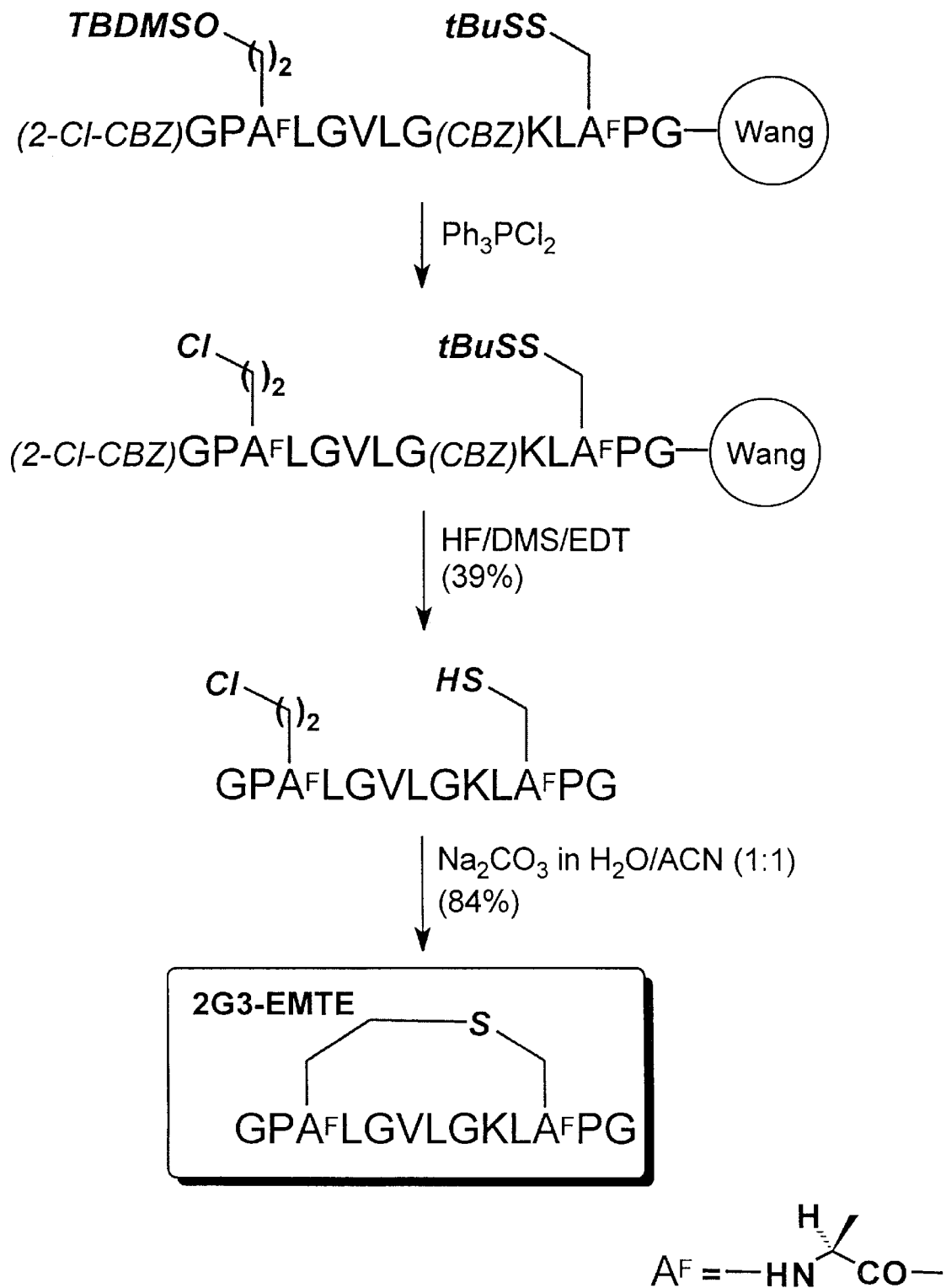
FIG. 5 is a reaction scheme illustrating the synthesis of the 2G3-EMTE (SEQ ID NO:9) cyclic peptide as described in Example 5.

A reaction scheme illustrating the synthesis in this example is shown in FIG. 5. The methods for polypeptide synthesis, chlorination, and cyclization described in Example 2, above, were adapted in this example. Side chain functional groups were protected as follows: Cys (tBuS); Lys (2-Cl—CBZ); Hs (TBDMS). The alpha-amino group of the peptide was protected with a CBZ group. The chlorination step was carried out using a solution of triphenylphosphine dichloride (i.e., $(C_6H_5)_3PCl_2$) in DCM (130 mg/mL). The dried polypeptide resin was treated with a 10:1:1 (v/v) mixture of HF, DMS, and ethylene dithiol for one hour at 0° C. The chloro-polypeptide was then purified using the methods of Example 2.

Using 0.5 g of (Fmoc)-Gly-Wang resin (Advanced ChemTech, 0.34 mmol/g) the chloro-polypeptide was obtained as a white powder after purification (82.6 mg, 39% yield; Analytical RP-HPLC: TFA system: $t_R$ 16.12 min; purity, 88.4%; TEAP system: $t_R$ 14.80 min; purity, 92.9%; MS (ESI): m/e (M+1) Calcd. for $C_{54}H_{94}N_{14}O_{14}SCl$: 1230, obsd.: 1230).

Using 36.5 mg of the chloro-polypeptide, the cyclic polypeptide was obtained as a white powder (29.7 mg, 84% yield; Analytical RP-HPLC: TFA system: $t_R$ 15.48 min; purity, 100%; TEAP system: $t_R$ 13.58 min; purity, 100%; HRMS (ESI): m/e (M+1) Calcd. for $C_{54}H_{93}N_{14}O_{14}S$: 1193.6717, obsd.: 1193.6674).

EXAMPLE 6
Cyclization of GPSLGVLGKLCPG (SEQ ID NO:32) to form 2G3-MMTE

The methods for polypeptide synthesis, chlorination, and cyclization described in Example 5, above, were adapted in this example. The same protecting group scheme for the side chain functional groups and alpha-amino group was used in this example.

Using 0.50 g of (Fmoc)-Gly-Wang resin (Advanced ChemTech, 0.34 mmol/g), the chloro-polypeptide was obtained as a white powder after purification (78.3 mg, 32% yield; Analytical RP-HPLC: TFA system: $t_R$ 15.88 min;

purity, 93.3%; TEAP system: $t_R$ 14.30 min; purity, 100%; MS (ESI): m/e (M+1) Calcd. for $C_{53}H_{92}N_{14}O_{14}SCl$: 1216, obsd.: 1216).

Using 34.2 mg of the chloro-polypeptide, the cyclic polypeptide was obtained as a mixture of two diastereomers (28.9 mg, 87% yield; Analytical RP-HPLC:TFA system: $t_R$ 14.90 min; purity, 100%; TEAP system: $t_R$ 11.93 min, purity, 58.8% and 12.17 min, purity, 41.%; HRMS (ESI): m/e (M+1) Calcd. for $C_{53}H_{91}N_{14}O_{14}S$: 1179.6560, obsd.: 1179.6610).

EXAMPLE 7

Cyclization of GPSLGVLGKLHcPG (SEQ ID NO:56) to form l-2G3-METE and d-2G3-METE

Figure 6:
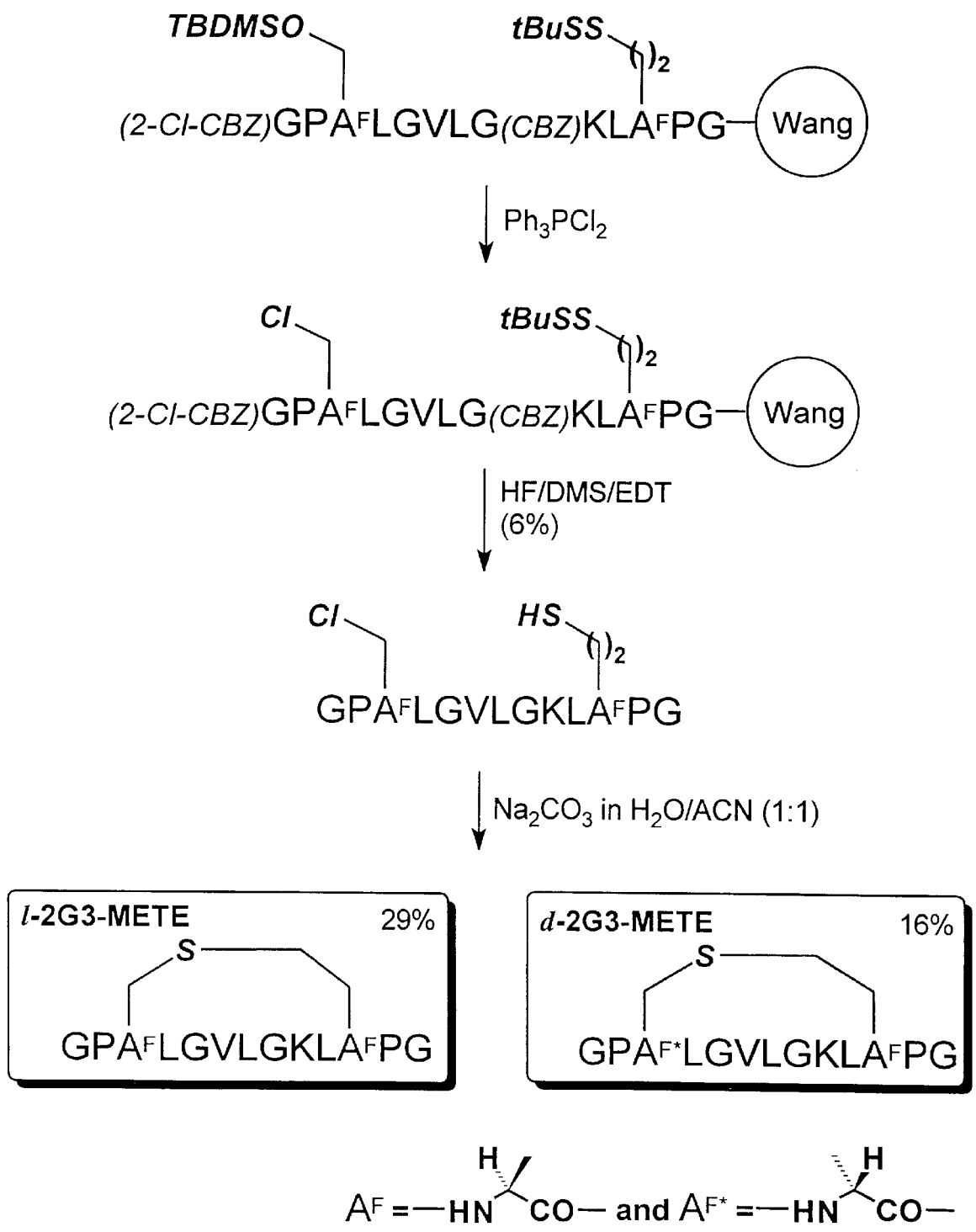
FIG. 6 is a reaction scheme illustrating the synthesis of the l-2G3-METE and d-2G3-METE (SEQ ID NO:10) cyclic peptides as described in Example 7.

A reaction scheme illustrating the synthesis in this example is shown in FIG. 6. The methods for polypeptide synthesis, chlorination, and cyclization described in Example 5, above, were adapted in this example. The same protecting group scheme for the side chain functional groups and alpha-amino group was used in this example.

Using 1.0 g of (Fmoc)-Gly-Wang resin (Advanced ChemTech, 0.34 mmol/g) the chloro-polypeptide was obtained as a white powder after purification (25.2 mg, 6% yield; Analytical RP-HPLC: TFA system: $t_R$ 16.29 min; purity, 100%; TEAP system: $t_R$ 14.06 min; purity, 92.0%; HRMS (ESI): m/e (M+1) Calcd. for $C_{54}H_{94}N_{14}O_{14}SCl$: 1230, obsd.: 1230).

Using 34.2 mg of the chloro-polypeptide, two cyclic polypeptides were obtained, the d-isomer and the l-isomer (d-isomer: 4.0 mg, 16% yield; Analytical RP-HPLC: TFA system: $t_R$ 15.04 min; purity, 98.4%; TEAP system: $t_R$ 12.66 min; purity, 91.6%; HRMS (ESI): m/e (M+Cs$^+$) Calcd. for $C_{54}H_{93}N_{14}O_{14}SCs$: 1325.5693, obsd.: 1325.5703; and l-isomer: 7.0 mg, 29% yield; Analytical RP-HPLC: TFA system: $t_R$ 15.39 min; purity, 85.3%; TEAP system: $t_R$ 13.09 min; purity, 84.4%; HRMS (ESI): m/e (M+Cs$^+$) Calcd. for $C_{54}H_{93}N_{14}O_{14}SCs$: 1325.5693, obsd.: 1325.5699).

EXAMPLE 8

Cyclization of GPCLGVLGKLHsPG (SEQ ID NO:57) to form 2G3-METE

Figure 7:
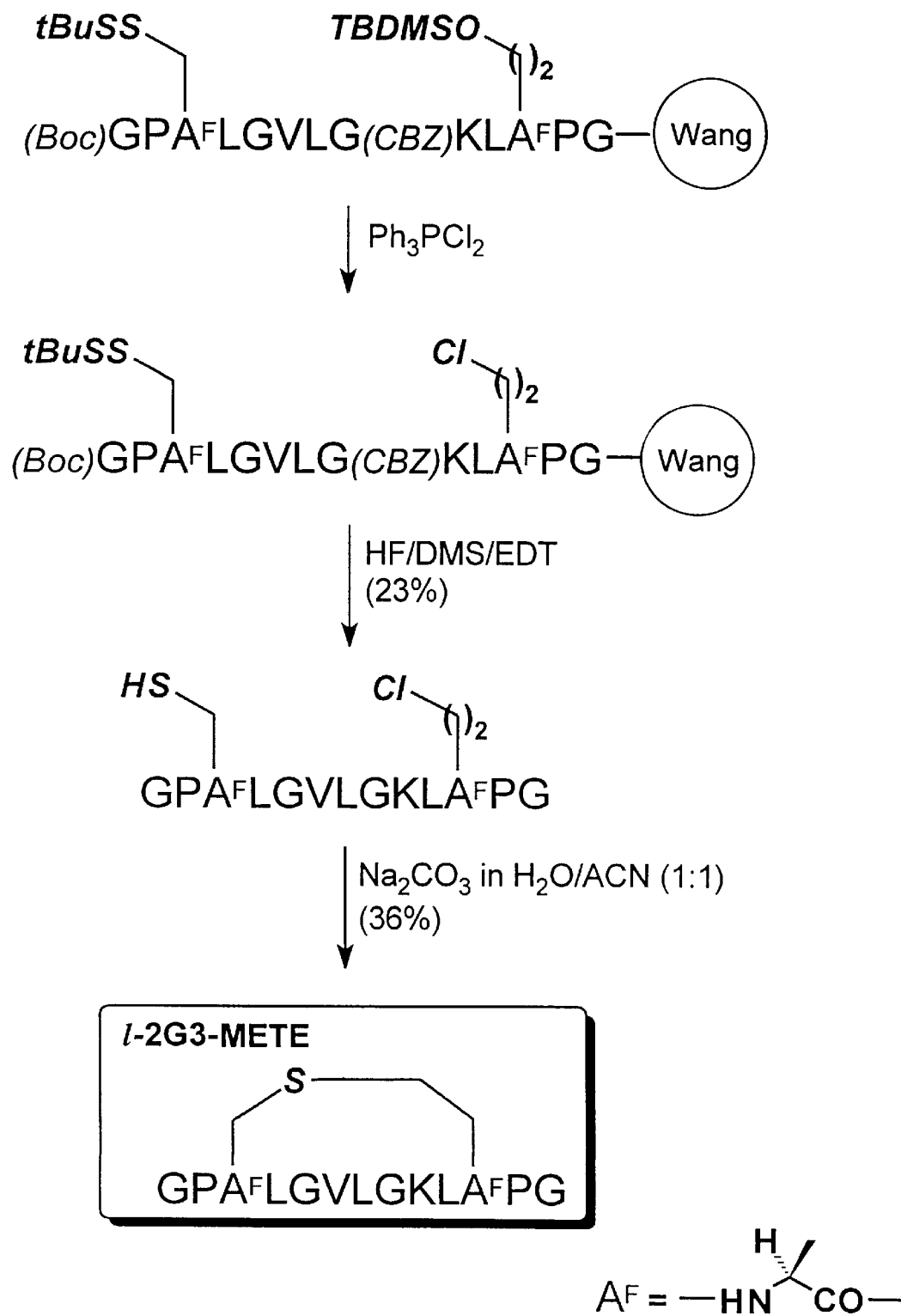
FIG. 7 is a reaction scheme illustrating the synthesis of the l-2G3-METE (SEQ ID NO:10) cyclic peptide as described in Example 8.

A reaction scheme illustrating the synthesis in this example is shown in FIG. 7. The methods for polypeptide synthesis, chlorination, and cyclization described in Example 5, above, were adapted in this example. The same protecting group scheme for the side chain functional groups was used in this example. The alpha-amino group of the peptide was protected with a Boc group.

Using 1.0 g of (Fmoc)-Gly-Wang resin (Advanced ChemTech, 0.34 mmol/g) the chloropolypeptide was obtained as a white powder after purification (114.3 mg, 23% yield; Analytical RP-HPLC: TFA system: $t_R$ 16.30 min; purity, 84.8%; TEAP system: $t_R$ 14.59 min; purity, 85.6%; MS (ESI): m/e (M+1) Calcd. for $C_{54}H_{94}N_{14}O_{14}SCl$: 1230, obsd.: 1230).

Using 17.9 mg of the chloro-polypeptide, the cyclic polypeptide was obtained as a white solid (6.3 mg, 36% yield; Analytical RP-HPLC: TFA system: $t_R$ 15.39 min; purity, 85.3%; TEAP system: $t_R$ 13.09 min; purity, 84.4%; HRMS (ESI): m/e (M+Cs$^+$) Calcd. for $C_{54}H_{93}N_{14}O_{14}SCs$: 1325.5693, obsd.: 1325.5699).

EXAMPLE 9

Cyclization of HsLGVLGKLC (SEQ ID NO:58) to form G3-EMTE

The methods for polypeptide synthesis, chlorination, and cyclization described in Example 8, above, were adapted in this example. The same protecting group scheme for the side chain functional groups and the alpha-amino group of the peptide was used in this example.

Using 0.45 g of MBHA resin (NovaBiochem, 0.42 mmol/g) the chloropolypeptide was obtained as a white powder after purification (158.2 mg, 73% yield; Analytical RP-HPLC: TFA system: $t_R$ 15.83 min; purity, 100%; TEAP system: $t_R$ 13.77 min; purity, 93.8%; MS (ESI): m/e (M+1) Calcd. for $C_{40}H_{75}N_{11}O_9SCl$: 920, obsd.: 920).

Using 50.0 mg of the chloro-polypeptide, the cyclic polypeptide was obtained as a white solid (24.7 mg, 51% yield; Analytical RP-HPLC: TFA system: $t_R$ 15.43 min; purity, 92.8%; TEAP system: $t_R$ 12.94 min; purity, 94.4%; HRMS (ESI): m/e (M+1) Calcd. for $C_{40}H_{74}N_{11}O_9S$: 885.5470, obsd.: 885.5491).

EXAMPLE 10

Cyclization of SLGVLGKLC (SEQ ID NO:38) to form G3-MMTE

The methods for polypeptide synthesis, chlorination, and cyclization described in Example 8, above, were adapted in this example. The same protecting group scheme for the side chain functional groups and the alpha-amino group of the peptide was used in this example.

Using 0.50 g of MBHA resin (NovaBiochem, 0.42 mmol/g) the chloropolypeptide was obtained as a white powder after purification (151.8 mg, 64% yield; Analytical RP-HPLC: TFA system: $t_R$ 15.33 min; purity, 98.2%; TEAP system: $t_R$ 13.40 min; purity, 98.4%; MS (ESI): m/e (M+1) Calcd. for $C_{39}H_{73}N_{11}O_9SCl$: 906, obsd.: 906).

Using 50.0 mg of the chloro-polypeptide, the cyclic polypeptide was obtained as a white solid (23.9 mg, 49% yield; Analytical RP-HPLC: TFA system: $t_R$ 15.13 min; purity, 97.1%; TEAP system: $t_R$ 12.27 min; purity, 97.6%; HRMS (ESI): m/e (M+1) Calcd. for $C_{39}H_{72}N_{11}O_9S$: 871.5313, obsd.: 871.5332).

EXAMPLE 11

Cyclization of HsLGVLGKLHc (SEQ ID NO:59) to form G3-EETE

Figure 8:
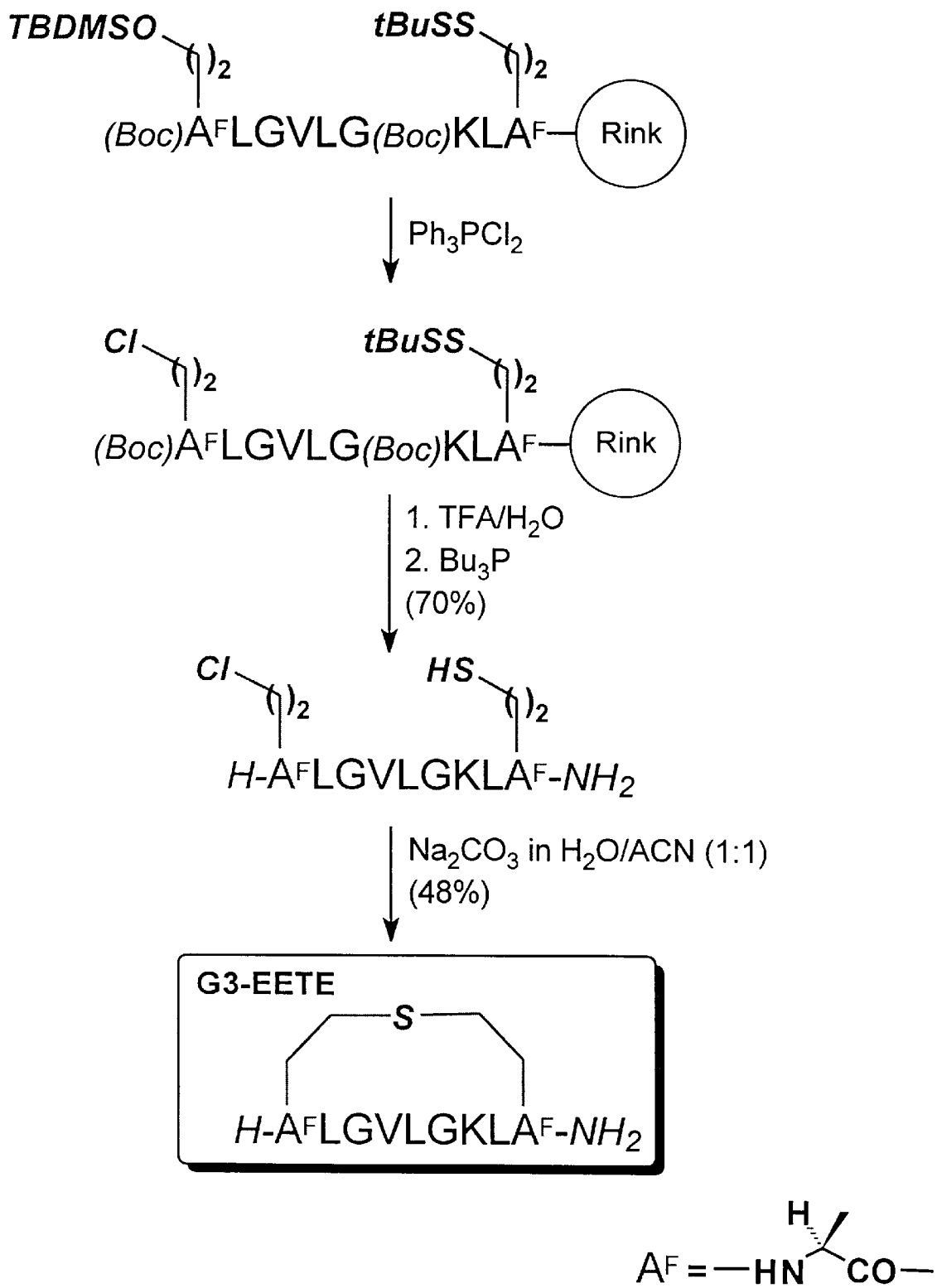
FIG. 8 is a reaction scheme illustrating the synthesis of the G3-EETE (SEQ ID NO:16) cyclic peptide as described in Example 11.

A reaction scheme illustrating the synthesis in this example is shown in FIG. 8. The resin-bound fully protected peptide (Boc)(TBDMS)HsLGVLG(Boc)KL(tBuS)Hc-resin was prepared by Method B on Rink amide MBHA resin (NovaBiochem, 0.5 g, 0.5 mmol/g). Side chain functional groups were protected as follows: Hc (tBuS); Lys (Boc); Hs (TBDMS). The alpha-amino group was protected with a Boc group. After completion of all couplings, the peptide resin was transferred from the reaction vessel to the cleavage vessels. The resin was washed with DCM (twice) and dried in vacuo.

The chlorination of the polypeptide was carried out using a solution of triphenylphosphine dichloride (i.e., $P(C_6H_5)_3Cl_2$) in DCM (200 mg/mL). The polypeptide resin was washed successively with DMF (twice), MeOH (twice), DMF (twice), and MeOH (twice) and then dried in vacuo. The dried polypeptide resin was treated with 95% TFA aqueous solution for one hour at room temperature. After removal of TFA and water under a stream of argon, the residue was washed three times with diethyl ether and then dissolved in 30 mL of 0.1% TFA in 1:1 (v/v) $H_2O$/ACN. To remove the tBuS protecting group of homocysteine residue, 0.75 mL tributylphosphine (i.e., $P(C_4H_9)_3$) was added to the crude polypeptide solution and stirred overnight at room temperature. The reaction mixture was lyophilized and the crude polypeptide was purified by preparative HPLC eluted at 10 mL/min with a linear gradient from 10 to 40% B over 40 minutes where A was 0.1% (v/v) TFA in $H_2O$ and B was 0.08% (v/v) TFA in ACN. The chloro-polypeptide was obtained as a white powder after lyophilization (162.5 mg, 70% yield; Analytical RP-HPLC: TFA system: $t_R$ 16.36 min; purity, 100%; TEAP system: $t_R$ 14.74 min; purity, 88.1%; HRMS (ESI): m/e (M+1) Calcd. for $C_{41}H_{77}N_{11}O_9SCl$: 934.5315, obsd.: 934.5361).

The cyclization was carried out according to the method in Example 2. Using 53.0 mg of the chloro-polypeptide, the cyclic polypeptide was obtained as a white solid (24.2 mg, 48% yield; Analytical RP-HPLC: TFA system: $t_R$ 15.61 min; purity, 97.1%; TEAP system: $t_R$ 13.23 min; purity, 98.0%; HRMS (ESI): m/e (M+1) Calcd. for $C_{41}H_{76}N_{11}O_9S$: 899.5626, obsd.: 899.5646).

EXAMPLE 12

Cyclization of SLGVLGKLHc (SEQ ID NO:60) to form G3-METE

The methods for polypeptide synthesis, chlorination, and cyclization described in Example 11, above, were adapted in this example. The same protecting group scheme for the side chain functional groups and the alpha-amino group of the peptide was used in this example.

Using 0.50 g of Rink amide MBHA resin (NovaBiochem, 0.50 mmol/g) the chloropolypeptide was obtained as a white powder after purification (57.5 mg, 25% yield; Analytical RP-HPLC: TFA system: $t_R$ 15.93 min; purity, 97.4%; TEAP system: $t_R$ 13.81 min; purity, 95.4%; HSMS (ESI): m/e (M+1) Calcd. for $C_{40}H_{75}N_{11}O_9SCl$: 920.5158, obsd.: 920.5206).

Using 17.3 mg of the chloro-polypeptide, the cyclic polypeptide was obtained as a white solid (8.5 mg, 52% yield; Analytical RP-HPLC: TFA system: $t_R$ 15.65 min; purity, 94.8%; TEAP system: $t_R$ 13.15 min; purity, 93.4%; HRMS (ESI): m/e (M+1) Calcd. for $C_{40}H_{74}N_{11}O_9S$: 885.5470, obsd.: 885.5488).

EXAMPLE 13

Cyclization of GPSLILAPDRC (SEQ ID NO:48) to form CB10-MMTE

The resin-bound fully protected peptide (Boc)GP(Tr)SLILAP(tBu)D(Pmc)R(tBuS)C-resin was synthesized using Method A on MBHA resin (NovaBiochem, 2.0 g, 0.6 mmol/g). Before the first coupling, the MBHA resin was neutralized with 20% piperidine (~5 mL/g) in DMF for 5 min and then washed successively with DMF (twice), MeOH (twice), DMF (twice), and MeOH (twice). Side chain functional groups were protected as follows: Arg (Pmc); Asp (tBu); Cys (tBuS); Lys (CBZ); and Ser (Tr). After completion of the polypeptide synthesis, the trityl protecting group of the serine residue was selectively removed by treatment five times with 1% TFA in DCM/MeOH (1:1 v/v) each for 30 minutes. The peptide resin was washed with DCM (twice) and subsequently dried in vacuo to yield 3.38 g of the resin-bound polypeptide.

The free hydroxyl group (i.e., —OH) of the serine residue, S, was converted to bromo group (i.e., —Br) by treatment of the resin-bound polypeptide (0.5 g, 0.044 mmol) with triphenylphosphine dibromide (i.e., $(C_6H_5)_3PBr_2$, 172 mg, 0.407 mmol) and DIEA (i.e., $((CH_3)_2CH)_2NCH_2CH_3$, diisopropylethylamine, 25 µl, 0.138 mmol) in 4 mL ACN overnight at room temperature. The polypeptide resin was washed successively with DMF (twice), MeOH (twice), DMF (twice), and MeOH (twice) and subsequently dried in vacuo. The dried polypeptide resin was then cleaved/deprotected with a 10:1:1:0.2 (v/v) mixture of HF, anisole, DMS, and para-thiocresol for one hour at 0° C. After removal of HF in vacuo, the residue was washed three times with diethyl ether to remove scavengers and extracted three times with 0.1% TFA in 1:1 (v/v) $H_2O$/ACN. The combined filtrates were lyophilized and the crude polypeptide was purified by preparative HPLC eluted at 10 mL/min with a linear gradient from 10 to 40% B over 40 minutes where A was 0.1% (v/v) TFA in $H_2O$ and B was 0.08% (v/v) TFA in ACN. The bromo-polypeptide was obtained as a white powder after further lyophilization (12.7 mg, 24% yield; MS (ESI): m/e (M+1) Calcd. for $C_{49}H_{85}N_{15}O_{13}SBr$: 1203, 1205, obsd. 1203, 1205).

The bromo-polypeptide (12.7 mg) was dissolved in 70 mL of an aqueous solution of sodium carbonate (i.e., $Na_2CO_3$) of pH ~10.5 for two days under argon. The cyclization reaction was monitored by analytical HPLC. After the completion of cyclization, indicated by the disappearance of the starting material, the solution was neutralized with TFA and lyophilized. The crude peptide was purified by preparative HPLC eluted at 10 mL/min with a linear gradient from 10 to 40% B over 40 minutes where A was 0.1% (v/v) TFA in $H_2O$ and B was 0.08% (v/v) TFA in ACN. The cyclic polypeptide was obtained as a white powder after further lyophilization (3.2 mg, 27% yield; MS (ESI): m/e (M+1) Calcd. for $C_{49}H_{84}N_{15}O_{13}S$: 1123, obsd. 1123).

EXAMPLE 14

Cyclization of HsL($N^a$MeGly)(d-V)(d-L)AKLC (SEQ ID NO:62) to form AG3-EMTE

Figure 9:
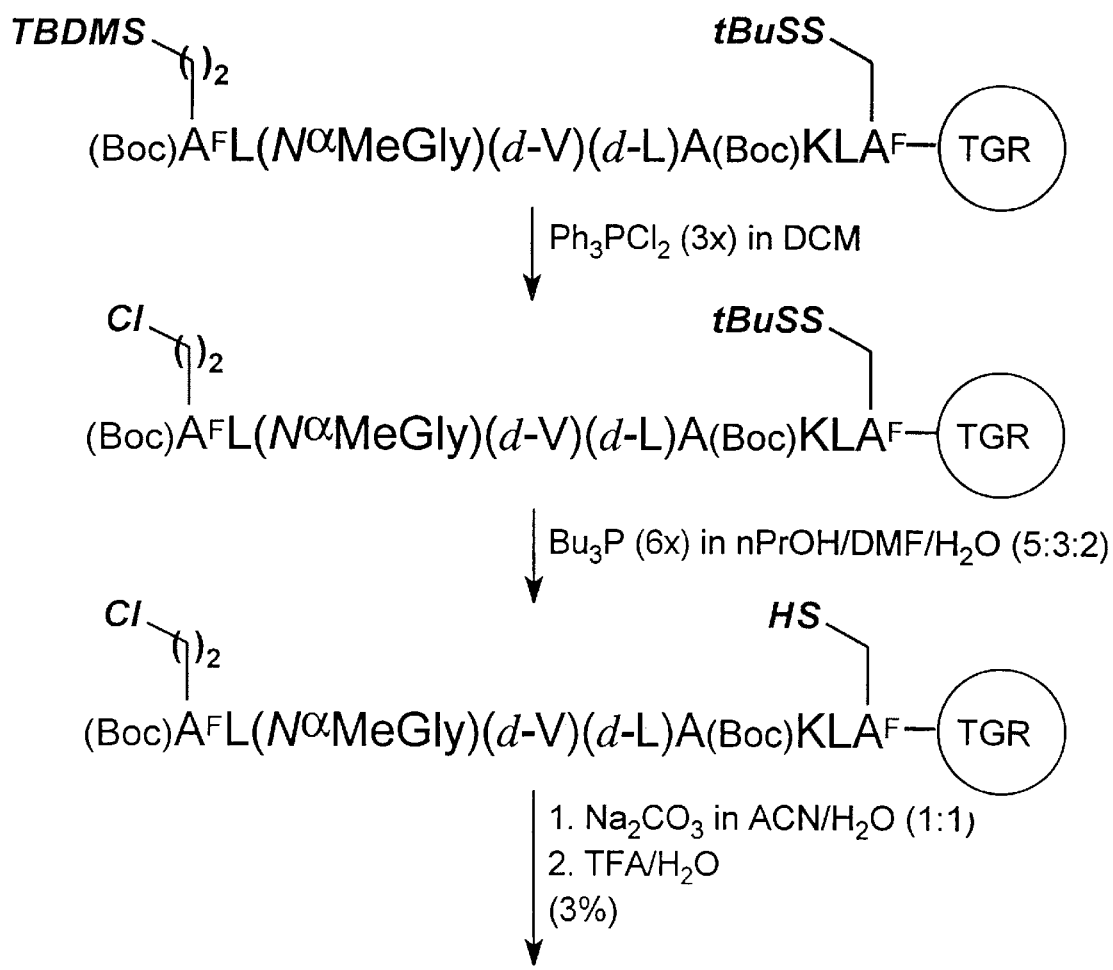
FIG. 9 is a reaction scheme illustrating the synthesis of the AG3-EMTE (SEQ ID NO:19) cyclic peptide as described in Example 14.
Figure 9:
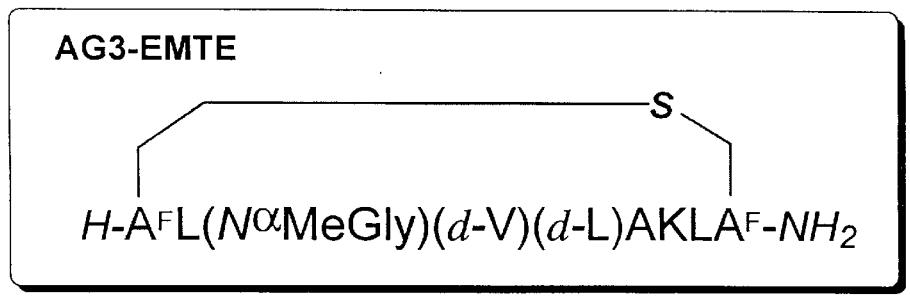
Figure 9:
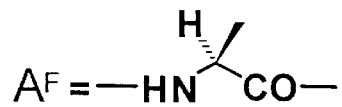

A reaction scheme illustrating the synthesis in this example is shown in FIG. 9. The resin-bound fully protected peptide (Boc)(TBDMS)HsL($N^a$MeGly)(d-V)(d-L)A(Boc)KL(tBuS)C-resin was prepared by Method B on NOVASYN® TGR resin (NovaBiochem, 1.0 g, 0.2 mmol/g). The notations d-V and d-L refer to d-valine and d-leucine, respectively. Side chain functional groups were protected as follows: Hs(TBDMS); Lys (Boc); Cys (tBuS). The alpha-amino group was protected with a Boc group. After completion of all couplings, the peptide resin was transferred from the reaction vessel to the cleavage vessels, and the resin washed with DCM (twice) and dried in vacuo.

The chlorination of the supported polypeptide was carried out using 6 equivalents of triphenylphosphine dichloride (i.e., $P(C_6H_5)_3Cl_2$) in DCM. The chlorination was completed after two hours as determined by cleaving a small portion of the peptide resin with 95% TFA aqueous solution for one hour at room temperature and analyzing the cleaved peptide by HPLC. The polypeptide resin was washed successively with DMF (twice), MeOH (twice), DMF (twice), MeOH (twice), and DCM (twice).

The tBuS protecting group on the cysteine residue was removed by treatment of the supported chlorinated polypeptide with 299 µl of tributylphosphine (i.e., $P(C_4H_9)_3$) in 10 mL of nPrOH/DMF/$H_2O$ (5:3:2) for one hour at room temperature. Afterward, the resin was washed successively with DMF (twice), MeOH (twice), DMF (twice), and MeOH (twice).

The on-resin cyclization was carried out in 10 mL of sodium carbonate solution (i.e., $Na_2CO_3$, 20 mg/mL) in ACN/$H_2O$ (1:1) for 48 hours at room temperature. After the completion of the cyclization, indicated by the absence of yellow color in the Ellman test (see, Ellman, *Arch. Biochem, Biophys.* (1959) 82:70), the resin was washed successively with DMF (twice), MeOH (twice), and DCM (twice), and subsequently dried in vacuo. The supported cyclic polypeptide was cleaved from the dried polypeptide resin by treatment with 95% TFA aqueous solution for one hour at room temperature. After removal of TFA and water in vacuo, the crude cyclic polypeptide was purified using preparative HPLC eluted at 10 mL/min with a linear gradient from 10 to 40% B in A over 40 minutes where A was 0.1% (v/v) TFA in H$_2$O and B was 0.08% (v/v) TFA in ACN. The cyclic polypeptide was obtained as a white powder after lyophilization (5.7 mg, 3% yield; Analytical RP-HPLC: TFA system: t$_R$ 14.54 min; purity 84.9%; TEAP system: t$_R$ 10.50 min; purity 86.9%; HRMS (ESI): m/e (M+Cs$^+$) Calcd. for C$_{42}$H$_{78}$N$_{11}$O$_9$SCs: 1044.4681, obsd. 1044.4653).

Examples 15 through 18 demonstrate the haloconversion of the serine-like amino acid, homoserine, when present in a polypeptide containing various other naturally occurring amino acids.

EXAMPLE 15
Chlorination of HsLRSLGEMC (SEQ ID NO:62)

The method for polypeptide synthesis in Example 14, above, was adapted in this example. Side chain functional groups were protected as follows: Hs (TBDMS); Arg (Pmc); Ser (tBu); Cys (tBuS). The alpha-amino group of the peptide was protected with a Boc group.

The chlorination of the polypeptide was carried out using 3 equivalents of freshly prepared triphenylphosphine dichloride (i.e., P(C$_6$H$_5$)$_3$Cl$_2$) in DCM for one hour. The polypeptide resin was washed successively with DMF (twice), MeOH (twice), and DCM (twice) and subsequently dried in vacuo. The chloropolypeptide was cleaved from the resin by treatment with 95% TFA aqueous solution at room temperature for one hour. After removal of the solvents in vacuo, the purity of the crude product was analyzed by RF-HPLC on a C-18 column eluted at 1 mL/min with a linear gradient from 20 to 80% B in A over 20 minutes where A was 0.1% (v/v) TFA in H$_2$O and B was 0.08% (v/v) TFA in ACN. The crude chloropeptide has two major components: the starting material (t$_R$ 8.84 min, 25.2%; MS (ESI): m/e (M+1) Calcd. for C$_{44}$H$_{82}$N$_{13}$O$_{13}$S$_3$: 1906, obsd.: 1096) and the chloropeptide (t$_R$ 9.26 min, 34.8%; MS (ESI): m/e (M+1) Calcd. for C$_{44}$H$_{81}$N$_{13}$O$_{12}$S$_3$Cl: 1114, obsd.: 1114).

EXAMPLE 16
Chlorination of HsLWFLGDLC (SEQ ID NO:63)

The methods for polypeptide synthesis and chlorination in Example 15, above, were adapted in this example. Side chain functional groups were protected as follows: Hs (TBDMS); Trp (Boc); Asp (tBu); Cys (tBuS). The alpha-amino group of the peptide was protected with a Boc group.

After the chlorination and the cleavage, the crude chloropeptide was analyzed by RF-HPLC and only one major peak was observed (t$_R$ 14.40 min, 80.6%, MS (ESI): m/e (M+1) Calcd. for C$_{55}$H$_{83}$N$_{11}$O$_{11}$S$_2$Cl: 1172, obsd.: 1172).

EXAMPLE 17
Chlorination of HsHNLGQLC (SEQ ID NO:64)

The methods for polypeptide synthesis and chlorination in Example 15, above, were adapted in this example. Side chain functional groups were protected as follows: Hs (TBDMS); His (Tr); Asn (Tr); Gln (Tr); Cys (tBuS). The alpha-amino group of the peptide was protected with a Boc group.

After the chlorination and the cleavage, the purity of the crude product was determined by analytical RF-HPLC and two major components were observed: the starting material (t$_R$ 8.91 min, 32.5%; MS (ESI): m/e (M+1) Calcd. for C$_{46}$H$_{81}$N$_{14}$O$_{12}$S$_2$: 1085, obsd.: 1085) and the chloropeptide (t$_R$ 9.33 min, 57.2%; MS (ESI): m/e (M+1) Calcd. for C$_{46}$H$_{80}$N$_{14}$O$_{11}$S$_2$Cl: 1103, obsd.: 1103).

EXAMPLE 18
Chlorination of HsYGTLGKLC (SEQ ID NO:65)

The methods for polypeptide synthesis and chlorination in Example 15, above, were adapted in this example. Side chain functional groups were protected as follows: Hs (TBDMS); Tyr (tBu); Thr (tBu); Lys (Boc); Cys (tBuS). The alpha-amino group of the peptide was protected with a Boc group.

After the chlorination and the cleavage, the purity of the crude product was determined by analytical RF-HPLC and one major components was observed: the chloropeptide (t$_R$ 9.35 min, 71.6%; MS (ESI): m/e (M+1) Calcd. for C$_{46}$H$_{79}$N$_{11}$O$_{11}$S$_2$Cl: 1060, obsd.: 1060).

EXAMPLE 19
Determination of Binding Affinity of Thioether Cyclic Polypeptide to Anticardiolipin Antibody The binding affinities of a number of the thioether cyclic polypeptides of the present invention to anticardiolipin antibody were determined by a competitive ELISA (i.e., enzyme-linked immunosorbent assay) and compared with binding affinities of the corresponding disulfide cyclic polypeptides (e.g., 3G3, 2G3, and G3).

Of 96 wells of a flat-bottom Immulon I microtiter plate (Dynatech Labs, Alexandria, Va.), 94 wells were coated with 50 mg cardiolipin per well in 30 mL of ethanol. The remaining two wells were used as controls and each received 30 mL of ethanol. After overnight evaporation at 4° C., the plate was blocked for 2 hours at room temperature with 200 mL of 5% (w/v) fish gelatin in phosphate buffered saline (i.e., PBS, 0.15M NaCl and 0.01M Na$_2$HPO$_4$ at pH 7.2). The plate was washed five times in Tris buffered saline (i.e., TBS, 0.15M NaCl and 0.05M Tris-HCl at pH 8.5). Then, β$_2$-glycoprotein I (i.e., β$_2$-GPI) was added as 100 mL/well of 2.3% (v/v) IgG-depleted human serum (Sigma Chemical Co.) and incubated for 2 hours at room temperature.

During this incubation, peptide solutions (around 2 mg/mL) were prepared by dissolving thioether cyclic peptides in 3% fish gelatin in TBS. The serums of patient ACA-6501, who has a GPL (i.e., IgG Phospholipid) score of 1500, and patient ACA-6701, who has a GPL score of 102, were diluted about 40-fold in 3% fish gelatin in TBS-PBS (1:1). Variable amounts of each of peptides were combined with 22 mL of each of the diluted human serums and then made up to the final volume of 220 mL with 3% fish gelatin in TBS-PBS (1:1). For each peptide, at least four peptide concentrations were employed and each data point was determined in duplicate.

After 5 washes with TBS, 100 mL of the peptide/human serum solution was added and the microplate was agitated at 40 rpm in an orbital shaker (American Scientific, Rotator V) for one hour at room temperature. The plate was washed extensively with TBS (5 times) and 100 mL of diluted (1/1000) alkaline phosphatase-conjugated goat anti-human IgG (Zymed, South San Francisco, Calif.) in 0.5% (w/v) BSA-TBS was added to each well (i.e., bovine serum albumin, BSA). The plate was then incubated for one hour at room temperature followed by addition of 100 mL/well of PPMP solution (3 g/L phenolphthalein monophosphate plus 26.7 g/L 2-amino-2-methyl-1-propanol in water). The plate was allowed to develop at room temperature for 21 min and the reaction was stopped by adding 50 mL of 0.2M $Na_2HPO_4$ (Mallinckrodt) to each well. Blanks consisted of protein-coated wells that received similar treatment except human serum was not added to these wells. The plate was read at 550 nm using a microplate reader (Bio-Tek Instruments, Model EL 311).

Absorbance vs. amount of peptide added was plotted using Graph Pad Prism (Graph Pad Software, Inc.). The amount of peptide that inhibited the human serum's binding by 50%, known as $IC_{50}$, was calculated from the graph at the intersection of half-maximal absorbance with amount of peptide added.

The results are shown in Table 1. In general, the thioether analogs have similar biological activities in comparison with the corresponding disulfide cyclic peptides. Interestingly, one of the thioester cyclic peptides in the series of G3 peptides, G3-EMTE, is more active than the disulfide peptide G3. In the case of the patient ACA-6501, G3-EMTE is about twice as active as G3.

TABLE 1

| | $IC_{50}$ ($\mu M$) | |
|---|---|---|
| Cyclic Polypeptide | ACA-6501 | ACA-6701 |
| 3G3 | 857 | 491 |
| 3G3-EMTE | ~1119 | not det'd. |
| 3G3-MMTE | ~1051 | ~1051 |
| 2G3 | 190 | 165 |
| 2G3-EETE | ~704 | 480 |
| 2G3-EMTE | 461 | 377 |
| d-2G3-METE | 100 | 436 |
| l-2G3-METE | 209 | 486 |
| 2G3-MMTE | >>678 | >>678 |
| G3 | 111 | 44 |
| G3-EETE | 89 | 40 |
| G3-EMTE | 52 | 34 |
| G3-METE | 104 | 36 |
| G3-MMTE | 126 | 57 |

I claim:

1. A method for the preparation of a cyclic polypeptide, said cyclic polypeptide having a polypeptide loop, said loop comprising a thioether linkage;

from a reactant polypeptide, said reactant polypeptide having a cysteine-like amino acid, said cysteine-like amino acid having a thiol group, and a serine-like amino acid, said serine-like amino acid having an hydroxyl group;

said method comprising the steps of:

(a) converting said hydroxyl group of said serine-like amino acid to a halo group with the aid of a phosphorus-based halogenation reagent to yield a haloalanine-like amino acid, and thus form a halogenated polypeptide; and (b) intramolecularly reacting said halo group of said haloalanine-like amino acid of said halogenated polypeptide with said thiol group of said cysteine-like amino acid of said halogenated polypeptide under basic conditions to form said thioether linkage.

2. The method of claim 1, wherein said phosphorus-based halogenation reagent comprises a reagent selected from the group consisting of triphenylphosphine dihalide, triphenylphosphite dihalide, mixtures of triphenylphosphine and a halohydrocarbon compound, and mixtures of triphenylphosphite and a halohydrocarbon compound.

3. The method of claim 1, wherein said basic conditions are provided by the addition of sodium carbonate.

4. The method of claim 1, wherein said reactant polypeptide is provided in a dissolved form.

5. The method of claim 1, wherein said reactant polypeptide is provided in a supported form; said conversion step (a) is performed using said supported reactant polypeptide; said halogenated polypeptide produced in step (a) is cleaved from its support to yield a dissolved halogenated polypeptide, prior to carrying out step (b); and said reaction step (b) is performed using said dissolved halogenated polypeptide.

6. The method of claim 1, wherein said reactant polypeptide is provided in a supported form; said conversion step (a) is performed using said supported reactant polypeptide to yield a supported halogenated polypeptide; and said reaction step (b) is performed using said supported halogenated polypeptide.

7. The method of claim 1, wherein said phosphorus-based halogenation reagent comprises triphenylphosphine dichloride.

8. The method of claim 1, wherein said phosphorus-based halogenation reagent comprises triphenylphosphine dibromide.

9. The method of claim 1, wherein said phosphorus-based halogenation reagent comprises a mixture of triphenylphosphine and carbon tetrachloride.

10. The method of claim 1, wherein a molar excess of said phosphorus-based halogenation reagent, in relation to said reactant polypeptide, is employed.

11. The method of claim 1, wherein said hydroxyl group of said serine-like amino acid is in a protected form.

12. The method of claim 1, wherein said hydroxyl group of said serine-like amino acid is in a protected form as a tert-butyldimethylsilyl ether group.

13. The method of claim 1, wherein said reactant polypeptide is in a supported form.

14. A method for the preparation of a halogenated polypeptide, said halogenated polypeptide having a haloalanine-like amino acid, said haloalanine-like amino acid having a halo group —X wherein X is Cl, Br, or I;

from a reactant polypeptide, said reactant polypeptide having a serine-like amino acid, said serine-like amino acid having an hydroxyl group;

said method comprising the step:

(a) converting said hydroxyl group of said serine-like amino acid to a halo group with the aid of a phosphorus-based halogenation reagent to yield a haloalanine-like amino acid.

15. The method of claim 14, wherein said phosphorus-based halogenation reagent comprises a reagent selected from the group consisting of triphenylphosphine dihalide, triphenylphosphite dihalide, mixtures of triphenylphosphine and a halohydrocarbon compound, and mixtures of triphenylphosphite and a halohydrocarbon compound.

16. The method of claim 14, wherein said phosphorus-based halogenation reagent comprises triphenylphosphine dichloride.

17. The method of claim 14, wherein said phosphorus-based halogenation reagent comprises triphenylphosphine dibromide.

18. The method of claim 14, wherein said phosphorus-based halogenation reagent comprises a mixture of triphenylphosphine and carbon tetrachloride.

19. The method of claim 14, wherein a molar excess of said phosphorus-based halogenation reagent, in relation to said reactant polypeptide, is employed.

20. The method of claim 14, wherein said hydroxyl group of said serine-like amino acid is in a protected form.

21. The method of claim 14, wherein said hydroxyl group of said serine-like amino acid is in a protected form as a tert-butyldimethylsilyl ether group.

22. The method of claim 14, wherein said reactant polypeptide is in a dissolved form.

23. The method of claim 14, wherein said reactant polypeptide is in a supported form.

* * * * *

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Cross-links
        ( B ) LOCATION: 2..4
        ( D ) OTHER INFORMATION: /note= "thioether linkage to form cyclic polypeptide"

( x i ) SEQUENCE DESCRIPTION: SEQ ID NO:1:

Xaa  Xaa  Xaa  Xaa  Xaa
    1                           5

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i x ) FEATURE:
        ( A ) NAME/KEY: Disulfide-bond
        ( B ) LOCATION: 4..12

( x i ) SEQUENCE DESCRIPTION: SEQ ID NO:2:

Ala  Gly  Pro  Cys  Leu  Gly  Val  Leu  Gly  Lys  Leu  Cys  Pro  Gly
    1                  5                                10

( 2 ) INFORMATION FOR SEQ ID NO:3:

( i ) SEQUENCE CHARACTERISTICS:

(A) LENGTH: 14 amino acids
(B) TYPE: amino acid
(C) STRANDEDNESS: single
(D) TOPOLOGY: linear (ix) FEATURE:
(A) NAME/KEY: Cross-links
(B) LOCATION: 4..12
(D) OTHER INFORMATION: /note= "methyl-methyl thioether bridge"

(xi) SEQUENCE DESCRIPTION: SEQ ID NO:3:

| Ala | Gly | Pro | Xaa | Leu | Gly | Val | Leu | Gly | Lys | Leu | Xaa | Pro | Gly |
|-----|-----|-----|-----|-----|-----|-----|-----|-----|-----|-----|-----|-----|-----|
| 1   |     |     |     | 5   |     |     |     |     | 10  |     |     |     |     |

(2) INFORMATION FOR SEQ ID NO:4:

(i) SEQUENCE CHARACTERISTICS:
(A) LENGTH: 14 amino acids
(B) TYPE: amino acid
(C) STRANDEDNESS: single
(D) TOPOLOGY: linear (ix) FEATURE:
(A) NAME/KEY: Cross-links
(B) LOCATION: 4..12
(D) OTHER INFORMATION: /note= "ethyl-methyl thioether bridge"

(xi) SEQUENCE DESCRIPTION: SEQ ID NO:4:

| Ala | Gly | Pro | Xaa | Leu | Gly | Val | Leu | Gly | Lys | Leu | Xaa | Pro | Gly |
|-----|-----|-----|-----|-----|-----|-----|-----|-----|-----|-----|-----|-----|-----|
| 1   |     |     |     | 5   |     |     |     |     | 10  |     |     |     |     |

(2) INFORMATION FOR SEQ ID NO:5:

(i) SEQUENCE CHARACTERISTICS:
(A) LENGTH: 14 amino acids
(B) TYPE: amino acid
(C) STRANDEDNESS: single
(D) TOPOLOGY: linear (ix) FEATURE:
(A) NAME/KEY: Cross-links
(B) LOCATION: 4..12
(D) OTHER INFORMATION: /note= "methyl-ethyl thioether bridge"

(xi) SEQUENCE DESCRIPTION: SEQ ID NO:5:

| Ala | Gly | Pro | Xaa | Leu | Gly | Val | Leu | Gly | Lys | Leu | Xaa | Pro | Gly |
|-----|-----|-----|-----|-----|-----|-----|-----|-----|-----|-----|-----|-----|-----|
| 1   |     |     |     | 5   |     |     |     |     | 10  |     |     |     |     |

(2) INFORMATION FOR SEQ ID NO:6:

(i) SEQUENCE CHARACTERISTICS:
(A) LENGTH: 14 amino acids
(B) TYPE: amino acid
(C) STRANDEDNESS: single
(D) TOPOLOGY: linear (ix) FEATURE:
(A) NAME/KEY: Cross-links
(B) LOCATION: 4..12
(D) OTHER INFORMATION: /note= "ethyl-ethyl thioether bridge"

(xi) SEQUENCE DESCRIPTION: SEQ ID NO:6:

| Ala | Gly | Pro | Xaa | Leu | Gly | Val | Leu | Gly | Lys | Leu | Xaa | Pro | Gly |
|-----|-----|-----|-----|-----|-----|-----|-----|-----|-----|-----|-----|-----|-----|
| 1   |     |     |     | 5   |     |     |     |     | 10  |     |     |     |     |

(2) INFORMATION FOR SEQ ID NO:7:

(i) SEQUENCE CHARACTERISTICS:

(A) LENGTH: 13 amino acids
                (B) TYPE: amino acid
                (C) STRANDEDNESS: single
                (D) TOPOLOGY: linear (ix) FEATURE:
                (A) NAME/KEY: Disulfide-bond
                (B) LOCATION: 3..11

(xi) SEQUENCE DESCRIPTION: SEQ ID NO:7:

Gly  Pro  Cys  Leu  Gly  Val  Leu  Gly  Lys  Leu  Cys  Pro  Gly
    1                  5                        10

(2) INFORMATION FOR SEQ ID NO:8:

(i) SEQUENCE CHARACTERISTICS:
                (A) LENGTH: 13 amino acids
                (B) TYPE: amino acid
                (C) STRANDEDNESS: single
                (D) TOPOLOGY: linear (ix) FEATURE:
                (A) NAME/KEY: Cross-links
                (B) LOCATION: 3..11
                (D) OTHER INFORMATION: /note= "methyl-methyl thioeither
                        bridge"

(xi) SEQUENCE DESCRIPTION: SEQ ID NO:8:

Gly  Pro  Xaa  Leu  Gly  Val  Leu  Gly  Lys  Leu  Xaa  Pro  Gly
    1                  5                        10

(2) INFORMATION FOR SEQ ID NO:9:

(i) SEQUENCE CHARACTERISTICS:
                (A) LENGTH: 13 amino acids
                (B) TYPE: amino acid
                (C) STRANDEDNESS: single
                (D) TOPOLOGY: linear (ix) FEATURE:
                (A) NAME/KEY: Cross-links
                (B) LOCATION: 3..11
                (D) OTHER INFORMATION: /note= "ethyl-methyl thioeither
                        bridge"

(xi) SEQUENCE DESCRIPTION: SEQ ID NO:9:

Gly  Pro  Xaa  Leu  Gly  Val  Leu  Gly  Lys  Leu  Xaa  Pro  Gly
    1                  5                        10

(2) INFORMATION FOR SEQ ID NO:10:

(i) SEQUENCE CHARACTERISTICS:
                (A) LENGTH: 13 amino acids
                (B) TYPE: amino acid
                (C) STRANDEDNESS: single
                (D) TOPOLOGY: linear (ix) FEATURE:
                (A) NAME/KEY: Cross-links
                (B) LOCATION: 3..11
                (D) OTHER INFORMATION: /note= "methyl-ethyl thioeither
                        bridge"

(xi) SEQUENCE DESCRIPTION: SEQ ID NO:10:

Gly  Pro  Xaa  Leu  Gly  Val  Leu  Gly  Lys  Leu  Xaa  Pro  Gly
    1                  5                        10

(2) INFORMATION FOR SEQ ID NO:11:

(i) SEQUENCE CHARACTERISTICS:
                (A) LENGTH: 13 amino acids
                (B) TYPE: amino acid ( C ) STRANDEDNESS: single
( D ) TOPOLOGY: linear ( i x ) FEATURE:
( A ) NAME/KEY: Cross-links
( B ) LOCATION: 3..11
( D ) OTHER INFORMATION: /note= "ethyl-ethyl thioeither
bridge"

( x i ) SEQUENCE DESCRIPTION: SEQ ID NO:11:

Gly Pro Xaa Leu Gly Val Leu Gly Lys Leu Xaa Pro Gly
1               5                       10

( 2 ) INFORMATION FOR SEQ ID NO:12:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i x ) FEATURE:
( A ) NAME/KEY: Disulfide-bond
( B ) LOCATION: 1..9

( x i ) SEQUENCE DESCRIPTION: SEQ ID NO:12:

Cys Leu Gly Val Leu Gly Lys Leu Cys
1               5

( 2 ) INFORMATION FOR SEQ ID NO:13:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i x ) FEATURE:
( A ) NAME/KEY: Cross-links
( B ) LOCATION: 1..9
( D ) OTHER INFORMATION: /note= "methyl-methyl thioether
bridge"

( i x ) FEATURE:
( A ) NAME/KEY: Modified-site
( B ) LOCATION: 9
( D ) OTHER INFORMATION: /label= - NH2
/ note= "carboxy protecting group (amide)"

( x i ) SEQUENCE DESCRIPTION: SEQ ID NO:13:

Xaa Leu Gly Val Leu Gly Lys Leu Xaa
1               5

( 2 ) INFORMATION FOR SEQ ID NO:14:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i x ) FEATURE:
( A ) NAME/KEY: Cross-links
( B ) LOCATION: 1..9
( D ) OTHER INFORMATION: /note= "ethyl-methyl thioether
bridge"

( i x ) FEATURE:
( A ) NAME/KEY: Modified-site
( B ) LOCATION: 9
( D ) OTHER INFORMATION: /label= - NH2
/ note= "carboxyl protecting group (amide)"

( x i ) SEQUENCE DESCRIPTION: SEQ ID NO:14:

```
Xaa  Leu  Gly  Val  Leu  Gly  Lys  Leu  Xaa
1                  5
```

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Cross-links
        ( B ) LOCATION: 1..9
        ( D ) OTHER INFORMATION: /note= "methyl-ethyl thioether
            bridge"

( i x ) FEATURE:
        ( A ) NAME/KEY: Modified-site
        ( B ) LOCATION: 9
        ( D ) OTHER INFORMATION: /label= - NH2
            / note= "carboxyl protecting group (amide)"

( x i ) SEQUENCE DESCRIPTION: SEQ ID NO:15:

```
Xaa  Leu  Gly  Val  Leu  Gly  Lys  Leu  Xaa
1                  5
```

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Cross-links
        ( B ) LOCATION: 1..9
        ( D ) OTHER INFORMATION: /note= "ethyl-ethyl thioether
            bridge"

( i x ) FEATURE:
        ( A ) NAME/KEY: Modified-site
        ( B ) LOCATION: 9
        ( D ) OTHER INFORMATION: /label= - NH2
            / note= "carboxyl protecting group (amide)"

( x i ) SEQUENCE DESCRIPTION: SEQ ID NO:16:

```
Xaa  Leu  Gly  Val  Leu  Gly  Lys  Leu  Xaa
1                  5
```

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Disulfide-bond
        ( B ) LOCATION: 1..9

( x i ) SEQUENCE DESCRIPTION: SEQ ID NO:17:

```
Cys  Leu  Gly  Val  Leu  Ala  Lys  Leu  Cys
1                  5
```

( 2 ) INFORMATION FOR SEQ ID NO:18:

( i ) SEQUENCE CHARACTERISTICS:
        ( A ) LENGTH: 9 amino acids
        ( B ) TYPE: amino acid ( C ) STRANDEDNESS: single
( D ) TOPOLOGY: linear ( i x ) FEATURE:
  ( A ) NAME/KEY: Cross-links
  ( B ) LOCATION: 1..9
  ( D ) OTHER INFORMATION: /note= "methyl-methyl thioether
    bridge"

( i x ) FEATURE:
  ( A ) NAME/KEY: Modified-site
  ( B ) LOCATION: 9
  ( D ) OTHER INFORMATION: /label= - NH2
    / note= "carboxyl protecting group (amide)"

( x i ) SEQUENCE DESCRIPTION: SEQ ID NO:18:

Xaa Leu Gly Val Leu Ala Lys Leu Xaa
1       5

( 2 ) INFORMATION FOR SEQ ID NO:19:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i x ) FEATURE:
  ( A ) NAME/KEY: Cross-links
  ( B ) LOCATION: 1..9
  ( D ) OTHER INFORMATION: /note= "ethyl-methyl thioether
    bridge"

( i x ) FEATURE:
  ( A ) NAME/KEY: Modified-site
  ( B ) LOCATION: 9
  ( D ) OTHER INFORMATION: /label= - NH2
    / note= "carboxyl protecting group (amide)"

( x i ) SEQUENCE DESCRIPTION: SEQ ID NO:19:

Xaa Leu Gly Val Leu Ala Lys Leu Xaa
1       5

( 2 ) INFORMATION FOR SEQ ID NO:20:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i x ) FEATURE:
  ( A ) NAME/KEY: Cross-links
  ( B ) LOCATION: 1..9
  ( D ) OTHER INFORMATION: /note= "methyl-ethyl thioether
    bridge"

( i x ) FEATURE:
  ( A ) NAME/KEY: Modified-site
  ( B ) LOCATION: 9
  ( D ) OTHER INFORMATION: /label= - NH2
    / note= "carboxyl protecting group (amide)"

( x i ) SEQUENCE DESCRIPTION: SEQ ID NO:20:

Xaa Leu Gly Val Leu Ala Lys Leu Xaa
1       5

( 2 ) INFORMATION FOR SEQ ID NO:21:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear (ix) FEATURE:
    (A) NAME/KEY: Cross-links
    (B) LOCATION: 1..9
    (D) OTHER INFORMATION: /note= "ethyl-ethyl thioether
        bridge"

(ix) FEATURE:
    (A) NAME/KEY: Modified-site
    (B) LOCATION: 9
    (D) OTHER INFORMATION: /label= - NH2
        / note= "carboxyl protecting group (amide)"

(xi) SEQUENCE DESCRIPTION: SEQ ID NO:21:

```
Xaa  Leu  Gly  Val  Leu  Ala  Lys  Leu  Xaa
1                  5
```

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
        (A) NAME/KEY: Disulfide-bond
        (B) LOCATION: 3..11

(xi) SEQUENCE DESCRIPTION: SEQ ID NO:22:

```
Gly  Pro  Cys  Leu  Ile  Leu  Ala  Pro  Asp  Arg  Cys
1                  5                        10
```

(2) INFORMATION FOR SEQ ID NO:23:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
        (A) NAME/KEY: Cross-links
        (B) LOCATION: 3..11
        (D) OTHER INFORMATION: /note= "methyl-methyl thioether
            bridge"

(ix) FEATURE:
        (A) NAME/KEY: Modified-site
        (B) LOCATION: 11
        (D) OTHER INFORMATION: /label= - NH2
            / note= "carboxyl protecting group (amide)"

(xi) SEQUENCE DESCRIPTION: SEQ ID NO:23:

```
Gly  Pro  Xaa  Leu  Ile  Leu  Ala  Pro  Asp  Arg  Xaa
1                  5                        10
```

(2) INFORMATION FOR SEQ ID NO:24:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
        (A) NAME/KEY: Cross-links
        (B) LOCATION: 3..11
        (D) OTHER INFORMATION: /note= "ethyl-methyl thioether
            bridge"

(ix) FEATURE:
        (A) NAME/KEY: Modified-site
        (B) LOCATION: 11

( D ) OTHER INFORMATION: /label= - NH2
/ note= "carboxyl protecting group (amide)"

( x i ) SEQUENCE DESCRIPTION: SEQ ID NO:24:

Gly Pro Xaa Leu Ile Leu Ala Pro Asp Arg Xaa
1               5                   10

( 2 ) INFORMATION FOR SEQ ID NO:25:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i x ) FEATURE:
( A ) NAME/KEY: Cross-links
( B ) LOCATION: 3..11
( D ) OTHER INFORMATION: /note= "methyl-ethyl thioether
bridge"

( i x ) FEATURE:
( A ) NAME/KEY: Modified-site
( B ) LOCATION: 11
( D ) OTHER INFORMATION: /label= - NH2
/ note= "carboxyl protecting group (amide)"

( x i ) SEQUENCE DESCRIPTION: SEQ ID NO:25:

Gly Pro Xaa Leu Ile Leu Ala Pro Asp Arg Xaa
1               5                   10

( 2 ) INFORMATION FOR SEQ ID NO:26:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i x ) FEATURE:
( A ) NAME/KEY: Cross-links
( B ) LOCATION: 3..11
( D ) OTHER INFORMATION: /note= "ethyl-ethyl thioether
bridge"

( i x ) FEATURE:
( A ) NAME/KEY: Modified-site
( B ) LOCATION: 11
( D ) OTHER INFORMATION: /label= - NH2
/ note= "carboxyl protecting group (amide)"

( x i ) SEQUENCE DESCRIPTION: SEQ ID NO:26:

Gly Pro Xaa Leu Ile Leu Ala Pro Asp Arg Xaa
1               5                   10

( 2 ) INFORMATION FOR SEQ ID NO:27:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( x i ) SEQUENCE DESCRIPTION: SEQ ID NO:27:

Ala Gly Pro Ser Leu Gly Val Leu Gly Lys Leu Cys Pro Gly
1               5                   10

( 2 ) INFORMATION FOR SEQ ID NO:28:

( i ) SEQUENCE CHARACTERISTICS:
( A ) LENGTH: 14 amino acids
( B ) TYPE: amino acid (C) STRANDEDNESS: single
(D) TOPOLOGY: linear (ix) FEATURE:
(A) NAME/KEY: Modified-site
(B) LOCATION: 4
(D) OTHER INFORMATION: /product="OTHER"
    / label= -CH2X
    / note= "methyl halide"

(xi) SEQUENCE DESCRIPTION: SEQ ID NO:28:

Ala Gly Pro Xaa Leu Gly Val Leu Gly Lys Leu Cys Pro Gly
1               5                   10

(2) INFORMATION FOR SEQ ID NO:29:

(i) SEQUENCE CHARACTERISTICS:
(A) LENGTH: 14 amino acids
(B) TYPE: amino acid
(C) STRANDEDNESS: single
(D) TOPOLOGY: linear (ix) FEATURE:
(A) NAME/KEY: Modified-site
(B) LOCATION: 4
(D) OTHER INFORMATION: /product="OTHER"
    / label= -CH2CH2X
    / note= "ethyl halide"

(xi) SEQUENCE DESCRIPTION: SEQ ID NO:29:

Ala Gly Pro Xaa Leu Gly Val Leu Gly Lys Leu Cys Pro Gly
1               5                   10

(2) INFORMATION FOR SEQ ID NO:30:

(i) SEQUENCE CHARACTERISTICS:
(A) LENGTH: 14 amino acids
(B) TYPE: amino acid
(C) STRANDEDNESS: single
(D) TOPOLOGY: linear (ix) FEATURE:
(A) NAME/KEY: Modified-site
(B) LOCATION: 4
(D) OTHER INFORMATION: /product="OTHER"
    / label= -CH2X
    / note= "methyl halide"

(ix) FEATURE:
(A) NAME/KEY: Modified-site
(B) LOCATION: 12
(D) OTHER INFORMATION: /product="OTHER"
    / label= Hc
    / note= "homocysteine"

(xi) SEQUENCE DESCRIPTION: SEQ ID NO:30:

Ala Gly Pro Xaa Leu Gly Val Leu Gly Lys Leu Xaa Pro Gly
1               5                   10

(2) INFORMATION FOR SEQ ID NO:31:

(i) SEQUENCE CHARACTERISTICS:
(A) LENGTH: 14 amino acids
(B) TYPE: amino acid
(C) STRANDEDNESS: single
(D) TOPOLOGY: linear (ix) FEATURE:
(A) NAME/KEY: Modified-site
(B) LOCATION: 4
(D) OTHER INFORMATION: /product="OTHER"
    / label= -CH2CH2X
    / note= "ethyl halide"

( i x ) FEATURE:
  ( A ) NAME/KEY: Modified-site
  ( B ) LOCATION: 12
  ( D ) OTHER INFORMATION: /product="OTHER"
    / label= Hc
    / note= "homocysteine"

( x i ) SEQUENCE DESCRIPTION: SEQ ID NO:31:

```
Ala Gly Pro Xaa Leu Gly Val Leu Gly Lys Leu Cys Pro Gly
1               5                   10
```

( 2 ) INFORMATION FOR SEQ ID NO:32:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( x i ) SEQUENCE DESCRIPTION: SEQ ID NO:32:

```
Gly Pro Ser Leu Gly Val Leu Gly Lys Leu Cys Pro Gly
1               5                   10
```

( 2 ) INFORMATION FOR SEQ ID NO:33:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 3
  ( D ) OTHER INFORMATION: /product="OTHER"
    / label= -CH2X
    / note= "methyl halide"

( x i ) SEQUENCE DESCRIPTION: SEQ ID NO:33:

```
Gly Pro Xaa Leu Gly Val Leu Gly Lys Leu Cys Pro Gly
1               5                   10
```

( 2 ) INFORMATION FOR SEQ ID NO:34:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 3
  ( D ) OTHER INFORMATION: /product="OTHER"
    / label= -CH2CH2X
    / note= "ethyl halide"

( x i ) SEQUENCE DESCRIPTION: SEQ ID NO:34:

```
Gly Pro Xaa Leu Gly Val Leu Gly Lys Leu Cys Pro Gly
1               5                   10
```

( 2 ) INFORMATION FOR SEQ ID NO:35:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 3

(D) OTHER INFORMATION: /product="OTHER"
            / label= -CH2X
            / note= "methyl halide"

(ix) FEATURE:
        (A) NAME/KEY: Modified-site
        (B) LOCATION: 11
        (D) OTHER INFORMATION: /product="OTHER"
            / label= Hc
            / note= "homocysteine"

(xi) SEQUENCE DESCRIPTION: SEQ ID NO:35:

Gly Pro Xaa Leu Gly Val Leu Gly Lys Leu Xaa Pro Gly
1               5                   10

(2) INFORMATION FOR SEQ ID NO:36:

(i) SEQUENCE CHARACTERISTICS:
        (A) LENGTH: 13 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 3
        (D) OTHER INFORMATION: /product="OTHER"
            / label= -CH2CH2X
            / note= "ethyl halide"

(ix) FEATURE:
        (A) NAME/KEY: Modified-site
        (B) LOCATION: 11
        (D) OTHER INFORMATION: /product="OTHER"
            / label= Hc
            / note= "homocysteine"

(xi) SEQUENCE DESCRIPTION: SEQ ID NO:36:

Gly Pro Xaa Leu Gly Val Leu Gly Lys Leu Xaa Pro Gly
1               5                   10

(2) INFORMATION FOR SEQ ID NO:37:

(i) SEQUENCE CHARACTERISTICS:
        (A) LENGTH: 13 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 11
        (D) OTHER INFORMATION: /product="OTHER"
            / label= -CH2CH2X
            / note= "ethyl halide"

(xi) SEQUENCE DESCRIPTION: SEQ ID NO:37:

Gly Pro Cys Leu Gly Val Leu Gly Lys Leu Xaa Pro Gly
1               5                   10

(2) INFORMATION FOR SEQ ID NO:38:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:38:

Ser Leu Gly Val Leu Gly Lys Leu Cys
1               5

( 2 ) INFORMATION FOR SEQ ID NO:39:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / label= -CH2X
            / note= "methyl halide"

( i x ) FEATURE:
        ( A ) NAME/KEY: Modified-site
        ( B ) LOCATION: 9
        ( D ) OTHER INFORMATION: /label= - NH2
            / note= "carboxyl protecting group (amide)"

( x i ) SEQUENCE DESCRIPTION: SEQ ID NO:39:

Xaa  Leu  Gly  Val  Leu  Gly  Lys  Leu  Cys
    1                            5

( 2 ) INFORMATION FOR SEQ ID NO:40:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / label= -CH2CH2X
            / note= "ethyl halide"

( i x ) FEATURE:
        ( A ) NAME/KEY: Modified-site
        ( B ) LOCATION: 9
        ( D ) OTHER INFORMATION: /label= - NH2
            / note= "carboxyl protecting group (amide)"

( x i ) SEQUENCE DESCRIPTION: SEQ ID NO:40:

Xaa  Leu  Gly  Val  Leu  Gly  Lys  Leu  Cys
    1                            5

( 2 ) INFORMATION FOR SEQ ID NO:41:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / label= -CH2X
            / note= "methyl halide"

( i x ) FEATURE:
        ( A ) NAME/KEY: Modified-site
        ( B ) LOCATION: 9
        ( D ) OTHER INFORMATION: /product="OTHER"
            / label= Hc-NH2
            / note= "homocysteine with carboxyl protecting group (amid ( x i ) SEQUENCE DESCRIPTION: SEQ ID NO:41:

Xaa  Leu  Gly  Val  Leu  Gly  Lys  Leu  Xaa
    1                            5

( 2 ) INFORMATION FOR SEQ ID NO:42:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / label= -CH2CH2X
            / note= "ethyl halide"

( i x ) FEATURE:
        ( A ) NAME/KEY: Modified-site
        ( B ) LOCATION: 9
        ( D ) OTHER INFORMATION: /product="OTHER"
            / label= Hc-NH2
            / note= "homocysteine with carboxyl protecting group
                    ( a m i d e )"

( x i ) SEQUENCE DESCRIPTION: SEQ ID NO:42:

Xaa  Leu  Gly  Val  Leu  Gly  Lys  Leu  Xaa
    1                          5

( 2 ) INFORMATION FOR SEQ ID NO:43:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:43:

Ser  Leu  Gly  Val  Leu  Ala  Lys  Leu  Cys
    1                          5

( 2 ) INFORMATION FOR SEQ ID NO:44:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /label= - CH2X
            / note= "methyl halide"

( i x ) FEATURE:
        ( A ) NAME/KEY: Modified-site
        ( B ) LOCATION: 3
        ( D ) OTHER INFORMATION: /product="MeGly"

( i x ) FEATURE:
        ( A ) NAME/KEY: Modified-site
        ( B ) LOCATION: 4
        ( D ) OTHER INFORMATION: /product="OTHER"
            / note= "D-Val"

( i x ) FEATURE:
        ( A ) NAME/KEY: Modified-site
        ( B ) LOCATION: 5
        ( D ) OTHER INFORMATION: /product="OTHER"
            / note= "D-Leu"

( i x ) FEATURE:
        ( A ) NAME/KEY: Modified-site
        ( B ) LOCATION: 9
        ( D ) OTHER INFORMATION: /label= - NH2

/ note= "carboxyl protecting group (amide)"

(x i) SEQUENCE DESCRIPTION: SEQ ID NO:44:

Xaa Leu Xaa Xaa Xaa Ala Lys Leu Cys
1               5

(2) INFORMATION FOR SEQ ID NO:45:

(i) SEQUENCE CHARACTERISTICS:
      (A) LENGTH: 9 amino acids
      (B) TYPE: amino acid
      (C) STRANDEDNESS: single
      (D) TOPOLOGY: linear (i x) FEATURE:
      (A) NAME/KEY: Modified-site
      (B) LOCATION: 1
      (D) OTHER INFORMATION: /label= - CH2CH2X
          / note= "ethyl halide"

(i x) FEATURE:
      (A) NAME/KEY: Modified-site
      (B) LOCATION: 3
      (D) OTHER INFORMATION: /product="MeGly"

(i x) FEATURE:
      (A) NAME/KEY: Modified-site
      (B) LOCATION: 4
      (D) OTHER INFORMATION: /product="OTHER"
          / note= "D-Val"

(i x) FEATURE:
      (A) NAME/KEY: Modified-site
      (B) LOCATION: 5
      (D) OTHER INFORMATION: /product="OTHER"
          / note= "D-Leu"

(i x) FEATURE:
      (A) NAME/KEY: Modified-site
      (B) LOCATION: 9
      (D) OTHER INFORMATION: /label= - NH2
          / note= "carboxyl protecting group (amide)"

(x i) SEQUENCE DESCRIPTION: SEQ ID NO:45:

Xaa Leu Xaa Xaa Xaa Ala Lys Leu Cys
1               5

(2) INFORMATION FOR SEQ ID NO:46:

(i) SEQUENCE CHARACTERISTICS:
      (A) LENGTH: 9 amino acids
      (B) TYPE: amino acid
      (C) STRANDEDNESS: single
      (D) TOPOLOGY: linear (i x) FEATURE:
      (A) NAME/KEY: Modified-site
      (B) LOCATION: 1
      (D) OTHER INFORMATION: /label= - CH2X
          / note= "methyl halide"

(i x) FEATURE:
      (A) NAME/KEY: Modified-site
      (B) LOCATION: 3
      (D) OTHER INFORMATION: /product="MeGly"

(i x) FEATURE:
      (A) NAME/KEY: Modified-site
      (B) LOCATION: 4
      (D) OTHER INFORMATION: /product="OTHER"
          / note= "D-Val"

(i x) FEATURE:
      (A) NAME/KEY: Modified-site
      (B) LOCATION: 5
      (D) OTHER INFORMATION: /product="OTHER"

/ note= "D-Leu"

( i x ) FEATURE:
    ( A ) NAME/KEY: Modified-site
    ( B ) LOCATION: 9
    ( D ) OTHER INFORMATION: /product="OTHER"
        / label= Hc-NH2
        / note= "homocysteine with carboxyl protecting group (amide)"

( x i ) SEQUENCE DESCRIPTION: SEQ ID NO:46:

Xaa Leu Xaa Xaa Xaa Ala Lys Leu Xaa
1                         5

( 2 ) INFORMATION FOR SEQ ID NO:47:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /label= - CH2CH2X
            / note= "ethyl halide"

( i x ) FEATURE:
        ( A ) NAME/KEY: Modified-site
        ( B ) LOCATION: 3
        ( D ) OTHER INFORMATION: /product="MeGly"

( i x ) FEATURE:
        ( A ) NAME/KEY: Modified-site
        ( B ) LOCATION: 4
        ( D ) OTHER INFORMATION: /product="OTHER"
            / note= "D-Val"

( i x ) FEATURE:
        ( A ) NAME/KEY: Modified-site
        ( B ) LOCATION: 5
        ( D ) OTHER INFORMATION: /product="OTHER"
            / note= "D-Leu"

( i x ) FEATURE:
        ( A ) NAME/KEY: Modified-site
        ( B ) LOCATION: 9
        ( D ) OTHER INFORMATION: /product="OTHER"
            / label= Hc-NH2
            / note= "homocysteine with carboxyl protecting group (amide)"

( x i ) SEQUENCE DESCRIPTION: SEQ ID NO:47:

Xaa Leu Xaa Xaa Xaa Ala Lys Leu Xaa
1                         5

( 2 ) INFORMATION FOR SEQ ID NO:48:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:48:

Gly Pro Ser Leu Ile Leu Ala Pro Asp Arg Cys
1                         5                         10

( 2 ) INFORMATION FOR SEQ ID NO:49:

( i ) SEQUENCE CHARACTERISTICS:
        ( A ) LENGTH: 11 amino acids
        ( B ) TYPE: amino acid (C) STRANDEDNESS: single
(D) TOPOLOGY: linear (ix) FEATURE:
    (A) NAME/KEY: Modified-site
    (B) LOCATION: 3
    (D) OTHER INFORMATION: /label= - CH2X
    / note= "methyl halide"

(ix) FEATURE:
    (A) NAME/KEY: Modified-site
    (B) LOCATION: 11
    (D) OTHER INFORMATION: /label= - NH2
    / note= "carboxyl protecting group"

(xi) SEQUENCE DESCRIPTION: SEQ ID NO:49:

Gly Pro Xaa Leu Ile Leu Ala Pro Asp Arg Cys
1               5                   10

(2) INFORMATION FOR SEQ ID NO:50:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
    (A) NAME/KEY: Modified-site
    (B) LOCATION: 3
    (D) OTHER INFORMATION: /label= - CH2CH2X
    / note= "ethyl halide"

(ix) FEATURE:
    (A) NAME/KEY: Modified-site
    (B) LOCATION: 11
    (D) OTHER INFORMATION: /label= - NH2
    / note= "carboxyl protecting group"

(xi) SEQUENCE DESCRIPTION: SEQ ID NO:50:

Gly Pro Xaa Leu Ile Leu Ala Pro Asp Arg Cys
1               5                   10

(2) INFORMATION FOR SEQ ID NO:51:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
    (A) NAME/KEY: Modified-site
    (B) LOCATION: 3
    (D) OTHER INFORMATION: /label= - CH2X
    / note= "methyl halide"

(ix) FEATURE:
    (A) NAME/KEY: Modified-site
    (B) LOCATION: 11
    (D) OTHER INFORMATION: /product="OTHER"
    / label= Hc-NH2
    / note= "homocysteine with carboxyl protecting group"

(xi) SEQUENCE DESCRIPTION: SEQ ID NO:51:

Gly Pro Xaa Leu Ile Leu Ala Pro Asp Arg Xaa
1               5                   10

(2) INFORMATION FOR SEQ ID NO:52:

(i) SEQUENCE CHARACTERISTICS:
        (A) LENGTH: 11 amino acids
        (B) TYPE: amino acid
        (C) STRANDEDNESS: single ( D ) TOPOLOGY: linear ( i x ) FEATURE:
        ( A ) NAME/KEY: Modified-site
        ( B ) LOCATION: 3
        ( D ) OTHER INFORMATION: /label= - CH2CH2X
            / note= "ethyl halide"

( i x ) FEATURE:
        ( A ) NAME/KEY: Modified-site
        ( B ) LOCATION: 11
        ( D ) OTHER INFORMATION: /product="OTHER"
            / label= Hc-NH2
            / note= "homocysteine with carboxyl protecting group"

( x i ) SEQUENCE DESCRIPTION: SEQ ID NO:52:

Gly Pro Xaa Leu Ile Leu Ala Pro Asp Arg Xaa
1               5                   10

( 2 ) INFORMATION FOR SEQ ID NO:53:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 4
        ( D ) OTHER INFORMATION: /product="OTHER"
            / label= Hs
            / note= "homoserine"

( x i ) SEQUENCE DESCRIPTION: SEQ ID NO:53:

Ala Gly Pro Xaa Leu Gly Val Leu Gly Lys Leu Cys Pro Gly
1               5                   10

( 2 ) INFORMATION FOR SEQ ID NO:54:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3
        ( D ) OTHER INFORMATION: /product="OTHER"
            / label= Hs
            / note= "homoserine"

( i x ) FEATURE:
        ( A ) NAME/KEY: Modified-site
        ( B ) LOCATION: 11
        ( D ) OTHER INFORMATION: /product="OTHER"
            / label= Hc
            / note= "homocysteine"

( x i ) SEQUENCE DESCRIPTION: SEQ ID NO:54:

Gly Pro Xaa Leu Gly Val Leu Gly Lys Leu Xaa Pro Gly
1               5                   10

( 2 ) INFORMATION FOR SEQ ID NO:55:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i x ) FEATURE:
        ( A ) NAME/KEY: Modified-site (B) LOCATION: 3
(D) OTHER INFORMATION: /product="OTHER"
/ label= Hs
/ note= "homoserine"

(xi) SEQUENCE DESCRIPTION: SEQ ID NO:55:

Gly Pro Xaa Leu Gly Val Leu Gly Lys Leu Cys Pro Gly
1               5                   10

(2) INFORMATION FOR SEQ ID NO:56:

(i) SEQUENCE CHARACTERISTICS:
(A) LENGTH: 13 amino acids
(B) TYPE: amino acid
(C) STRANDEDNESS: single
(D) TOPOLOGY: linear (ix) FEATURE:
(A) NAME/KEY: Modified-site
(B) LOCATION: 11
(D) OTHER INFORMATION: /product="OTHER"
/ label= Hc
/ note= "homocysteine"

(xi) SEQUENCE DESCRIPTION: SEQ ID NO:56:

Gly Pro Ser Leu Gly Val Leu Gly Lys Leu Xaa Pro Gly
1               5                   10

(2) INFORMATION FOR SEQ ID NO:57:

(i) SEQUENCE CHARACTERISTICS:
(A) LENGTH: 13 amino acids
(B) TYPE: amino acid
(C) STRANDEDNESS: single
(D) TOPOLOGY: linear (ix) FEATURE:
(A) NAME/KEY: Modified-site
(B) LOCATION: 11
(D) OTHER INFORMATION: /product="OTHER"
/ label= Hs
/ note= "homoserine"

(xi) SEQUENCE DESCRIPTION: SEQ ID NO:57:

Gly Pro Cys Leu Gly Val Leu Gly Lys Leu Xaa Pro Gly
1               5                   10

(2) INFORMATION FOR SEQ ID NO:58:

(i) SEQUENCE CHARACTERISTICS:
(A) LENGTH: 9 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /product="OTHER"
/ label= Hs
/ note= "homoserine"

(xi) SEQUENCE DESCRIPTION: SEQ ID NO:58:

Xaa Leu Gly Val Leu Gly Lys Leu Cys
1               5

(2) INFORMATION FOR SEQ ID NO:59:

(i) SEQUENCE CHARACTERISTICS:
(A) LENGTH: 9 amino acids
(B) TYPE: amino acid
(C) STRANDEDNESS: single ( D ) TOPOLOGY: linear ( i x ) FEATURE:
    ( A ) NAME/KEY: Modified-site
    ( B ) LOCATION: 1
    ( D ) OTHER INFORMATION: /product="OTHER"
        / label= Hs
        / note= "homoserine"

( i x ) FEATURE:
    ( A ) NAME/KEY: Modified-site
    ( B ) LOCATION: 9
    ( D ) OTHER INFORMATION: /product="OTHER"
        / label= Hc
        / note= "homocysteine"

( x i ) SEQUENCE DESCRIPTION: SEQ ID NO:59:

Xaa Leu Gly Val Leu Gly Lys Leu Xaa
1                    5

( 2 ) INFORMATION FOR SEQ ID NO:60:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
    ( A ) NAME/KEY: Modified-site
    ( B ) LOCATION: 9
    ( D ) OTHER INFORMATION: /product="OTHER"
        / label= Hc
        / note= "homocysteine"

( x i ) SEQUENCE DESCRIPTION: SEQ ID NO:60:

Ser Leu Gly Val Leu Gly Lys Leu Xaa
1                    5

( 2 ) INFORMATION FOR SEQ ID NO:61:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
    ( A ) NAME/KEY: Modified-site
    ( B ) LOCATION: 1
    ( D ) OTHER INFORMATION: /product="OTHER"
        / label= Hs
        / note= "homoserine"

( i x ) FEATURE:
    ( A ) NAME/KEY: Modified-site
    ( B ) LOCATION: 3
    ( D ) OTHER INFORMATION: /product="MeGly"

( i x ) FEATURE:
    ( A ) NAME/KEY: Modified-site
    ( B ) LOCATION: 4
    ( D ) OTHER INFORMATION: /product="OTHER"
        / note= "D-Val"

( i x ) FEATURE:
    ( A ) NAME/KEY: Modified-site
    ( B ) LOCATION: 5
    ( D ) OTHER INFORMATION: /product="OTHER"
        / note= "D-Leu"

( x i ) SEQUENCE DESCRIPTION: SEQ ID NO:61:

Xaa Leu Xaa Xaa Xaa Ala Lys Leu Cys
1                    5

( 2 ) INFORMATION FOR SEQ ID NO:62:

( i ) SEQUENCE CHARACTERISTICS:
          ( A ) LENGTH: 9 amino acids
          ( B ) TYPE: amino acid
          ( C ) STRANDEDNESS: single
          ( D ) TOPOLOGY: linear ( i x ) FEATURE:
          ( A ) NAME/KEY: Modified-site
          ( B ) LOCATION: 1
          ( D ) OTHER INFORMATION: /product="OTHER"
                  / label= Hs
                  / note= "homoserine"

( x i ) SEQUENCE DESCRIPTION: SEQ ID NO:62:

Xaa   Leu   Arg   Ser   Leu   Gly   Glu   Met   Cys
   1                       5

( 2 ) INFORMATION FOR SEQ ID NO:63:

( i ) SEQUENCE CHARACTERISTICS:
          ( A ) LENGTH: 9 amino acids
          ( B ) TYPE: amino acid
          ( C ) STRANDEDNESS: single
          ( D ) TOPOLOGY: linear ( i x ) FEATURE:
          ( A ) NAME/KEY: Modified-site
          ( B ) LOCATION: 1
          ( D ) OTHER INFORMATION: /product="OTHER"
                  / label= Hs
                  / note= "homoserine"

( x i ) SEQUENCE DESCRIPTION: SEQ ID NO:63:

Xaa   Leu   Trp   Phe   Leu   Gly   Asp   Leu   Cys
   1                       5

( 2 ) INFORMATION FOR SEQ ID NO:64:

( i ) SEQUENCE CHARACTERISTICS:
          ( A ) LENGTH: 8 amino acids
          ( B ) TYPE: amino acid
          ( C ) STRANDEDNESS: single
          ( D ) TOPOLOGY: linear ( i x ) FEATURE:
          ( A ) NAME/KEY: Modified-site
          ( B ) LOCATION: 1
          ( D ) OTHER INFORMATION: /product="OTHER"
                  / label= Hs
                  / note= "homoserine"

( x i ) SEQUENCE DESCRIPTION: SEQ ID NO:64:

Xaa   His   Asn   Leu   Gly   Gln   Leu   Cys
   1                       5

( 2 ) INFORMATION FOR SEQ ID NO:65:

( i ) SEQUENCE CHARACTERISTICS:
          ( A ) LENGTH: 9 amino acids
          ( B ) TYPE: amino acid
          ( C ) STRANDEDNESS: single
          ( D ) TOPOLOGY: linear ( i x ) FEATURE:
          ( A ) NAME/KEY: Modified-site
          ( B ) LOCATION: 1
          ( D ) OTHER INFORMATION: /product="OTHER"
                  / label= Hs
                  / note= "homoserine"

( x i ) SEQUENCE DESCRIPTION: SEQ ID NO:65:

-continued

```
Xaa  Tyr  Gly  Thr  Leu  Gly  Lys  Leu  Cys
 1                    5
```